United States Patent
Vander Horn et al.

(10) Patent No.: US 7,560,260 B2
(45) Date of Patent: Jul. 14, 2009

(54) COMPOSITIONS WITH POLYMERASE ACTIVITY

(75) Inventors: Peter B. Vander Horn, Foster City, CA (US); Yan Wang, San Francisco, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 173 days.

(21) Appl. No.: 10/627,582

(22) Filed: Jul. 25, 2003

(65) Prior Publication Data

US 2004/0219558 A1 Nov. 4, 2004

Related U.S. Application Data

(60) Provisional application No. 60/483,287, filed on Jun. 27, 2003, provisional application No. 60/398,687, filed on Jul. 25, 2002.

(51) Int. Cl.
*C12N 9/12* (2006.01)
*C12P 19/34* (2006.01)

(52) U.S. Cl. ............... 435/194; 435/183; 435/91.1; 435/91.2

(58) Field of Classification Search .............. None
See application file for complete search history.

(56) References Cited

U.S. PATENT DOCUMENTS

| | | |
|---|---|---|
| 5,093,257 A | 3/1992 | Gray |
| 5,489,523 A | 2/1996 | Mathur |
| 5,834,285 A | 11/1998 | Comb et al. |
| 5,948,663 A | 9/1999 | Mathur |
| 6,132,970 A | 10/2000 | Stemmer |

FOREIGN PATENT DOCUMENTS

| | | |
|---|---|---|
| WO | WO 97/07202 A1 | 2/1997 |
| WO | WO 97/07205 A1 | 2/1997 |
| WO | WO 01/27632 A2 | 4/2001 |
| WO | WO 01/61015 A2 | 8/2001 |
| WO | WO 01/92501 A1 | 12/2001 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*
Altamirano, M., et al., "Directed evolution of new catalytic activity using the α/β-barrel scaffold," *Nature*, (Feb. 10, 2000) 403: 617-622.
Farinas, E., et al., "Directed enzyme evolution," *Curr. Opin. Biotechnol.*, (2001) 12(6): 545-551.
Van Kampen, M., et al., "Substrate Specificity of *Staphylococcus hyicus* Lipase and *Staphylococcus aureus* Lipase as studied by in vivo chimeragenesis," *Biochemistry*, (1998) 37:3459-3466.
Biles, Benjamin D. et al.; "Low-fidelity *Pyrococcus furiosus* DNA polymerase mutants useful in error-prone PCR"; 2004, *Nucleic Acids Research*, vol. 32, No. 22, 7 pages.
Evans, Steven J. et al.; "Improving dideoxynucleotide-triphosphate utilization by the hyper-thermophilic DNA polymerase from the archaeon *Pyrococcus furiosus*"; 2000, *Nucleic Acids Research*, vol. 28, No. 5, pp. 1059-1066.
Perler, Francine B. et al.; "Thermostable DNA Polymerases"; 1996, *Advances in Protein Chemistry*, vol. 48, pp. 377-435.
"DNA polymerase (Fragment). Egkiitrgle Ivrrdwseia Ketqakvlea Ilkhgnveea Vkivkevtek Lsnyeipvek"; 2001, *EBI accession No. UNIPROT: Q9HH98, Database accession No. Q9HH98*, 1 page abstract.

* cited by examiner

*Primary Examiner*—Richard G Hutson
(74) *Attorney, Agent, or Firm*—Townsend and Townsend and Crew LLP

(57) ABSTRACT

The invention provides novel compositions with polymerase activity and methods of using the compositions.

2 Claims, 13 Drawing Sheets

```
                        430                    500                    510                    520                    530                    540
Pfu             D Y R Q K A I K L L A N S F Y G Y Y Y G Y A K A R W Y C K E C A E S V T A W G R K Y I E L V W K E L E E K F G F K V L Y I
DeepVent        D Y R Q R A I K I L A N S Y Y G Y Y Y G Y A K A R W Y C K E C A E S V T A W G R E Y I E F V R K E E K F G F K V L Y I
Hybrid_design   D Y R Q X A I K X L A N S X Y G Y Y Y G Y A K A R W Y C K E C A E S V T A W G R X Y I E X V X K E L E E K F G F K V L Y I 550                    560                    570                    580                    590                    600
Pfu             D T D G L Y A T I P G G E S E E I K K K A L E F V K Y I N S K L P G L L E L E Y E G F Y K R G F F V T K K K R Y A V I D E
DeepVent        D T D G L Y A T I P G A K P E E I K K K A L E F V D Y I N A K L P G L L E L E Y E G F Y V R G F F V T K K K Y A L I D E
Hybrid_design   D T D G L Y A T I P G X X X E E I K K K A L E F V K Y I N X K L P G L L E L E Y E G F Y X R G F F V T K K X Y A X I D E 610                    620                    630                    640                    650                    660
Pfu             E G K V I T R G L E I V R R D W S E I A K E T Q A R V L E T I L K H G D V E E A V R I V K E V I Q K L A N Y E I P P E K
DeepVent        E G K I I T R G L E I V R R D W S E I A K E T Q A K V L E A I L K H G N V E E A V K I V K E V T E K L S K Y E I P P E K
Hybrid_design   E G K X I T R G L E I V R R D W S E I A K E T Q A X V L E X I L K H G X V E E A V X I V K E V X X I K L X X Y E I P P E K 670                    680                    690                    700                    710                    720
Pfu             L A I Y E Q I T R P L H E Y K A I G P H V A V A K K L A A K G V K I K P G M V I G Y I V L R G D G P I S N R A I L A E E
DeepVent        L V I Y E Q I T R P L H E Y K A I G P H V A V A K R L A A R G V K I V R P G M V I G Y I V L R G D G P I S K R A I L A E E
Hybrid_design   L X I Y E Q I T R P L H E Y K A I G P H V A V A K X L A A X G V K X X P G M V I G Y I V L R G D G P I S X R A I L A E E 730                    740                    750                    760                    770                    780
Pfu             Y D P K K H K Y D A E Y Y I E N Q V L P A V L R I L E G F G Y R K E D L R Y Q K T R Q V G L T S W L N I K K S
DeepVent        F D L R K H K Y D A E Y Y I E N Q V L P A V L R I L E A F G Y R K E D L R W Q K T K Q T G L T A W L N I K K K
Hybrid_design   X D X X K H K Y D A E Y Y I E N Q V L P A V L R I L E X F G Y R K E D L R X Q K T X Q X G L T X W L N I K K S G T H N C 790                    800                    810                    820                    830                    840
Pfu             
DeepVent        
Hybrid_design   N H D
```

Figure 2. Assembly of the oligonucleotides into library fragments.

Figure 3. A comparison of the polymerase to 3' to 5' exonuclease activity

COMPOSITIONS WITH POLYMERASE ACTIVITY

CROSS-REFERENCES TO RELATED APPLICATIONS

This application claims the benefit of U.S. Provisional Application No. 60/398,687, filed Jul. 25, 2002; and U.S. Provisional Application 60/483,287, filed Jun. 27, 2003, each of which applications is herein incorporated by reference.

FIELD OF THE INVENTION

The present invention provides novel compositions with polymerase activity and methods of using those compositions

BACKGROUND OF THE INVENTION

Polymerases catalyze the formation of biological polymers. Polymerases are useful for the synthesis of DNA from deoxyribonucleoside triphosphates in the presence of a nucleic acid template and a nucleic acid primer; the synthesis of RNA from ribonucleotides and a DNA or RNA template; DNA replication and repair; and in vitro DNA or RNA amplification.

The 3' to 5' exonuclease activity, commonly referred to as "proofreading" activity, is an important characteristic of some DNA polymerases and is present in *Pyrococcus* species family B polymerases such as *Pyrococcus furiosus* PolI (referred to herein as "Pfu" and described in U.S. Pat. No. 5,948,663; commercially available from Stratagene, San Diego, Calif.) and *Pyrococcus* strain GB-D PolI (referred to herein as "Deep Vent®" and described U.S. Pat. No. 5,834,285; commercially available from New England Biolabs, Beverly Mass.). The essential function of the 3' to 5' exonuclease is to recognize and cleave a non-base-paired terminus. Enzymes with high exonuclease activity, however, are not commonly used in reactions relying on polymerase activity because they have poor processivity. For example, if used in PCR, it is often in combination with *Thermus aquaticus* DNA PolI, (Taq), an enzyme with higher processivity but no 3' to 5' exonuclease activity, in order to improve the fidelity of the PCR reaction. Improved processivity in polymerases with high 3' to 5' exonuclease activity would greatly increase the reliability of reactions relying on the use of polymerases and would eliminate, in some cases, the need for Taq polymerase. Accordingly, a need exists for creating improved polymerases with 3' to 5' exonuclease activity.

This invention addresses this and other needs by providing novel compositions with polymerase activity.

BRIEF SUMMARY OF THE INVENTION

The invention provides hybrid polymerase polypeptides having residues from multiple parent polymerases. The invention also provides nucleic acids encoding such proteins. Thus, in one aspect, the invention provides a hybrid polymerase having polymerase activity, wherein the polymerase comprises SEQ ID NO:23 and is at least 80% identical over 700 contiguous amino acids of the *Pyrococcus furiosus* (Pfu) sequence set forth in SEQ ID NO: 24 or at least 80% identical over 700 contiguous amino acids of the Deep Vent® sequence set forth in SEQ ID NO:25, with the proviso that (a) when the polymerase is at least 85% identical to SEQ ID NO:24, the sequence comprises at least one hybrid position that is mutated from the native Pfu residue to the residue that occurs at the corresponding position of SEQ ID NO:25, wherein the hybrid position is one of the residues designated as "X" in SEQ ID NO:26; or (b) when the polymerase is at least 85% identical to SEQ ID NO:25, the sequence comprises at least one hybrid position that is mutated from the native Deep Vent® residue to the residue that occurs at the corresponding position of SEQ ID NO:24, wherein the hybrid position is one of the residues designated as "X" in SEQ ID NO:26. In some embodiments, the polymerase is at least 90% identical over 700 contiguous amino acids of the Pfu sequence set forth in SEQ ID NO:24 or at least 90% identical over 700 contiguous amino acids of the Deep Vent® sequence set forth in SEQ ID NO:25.

In some embodiments, the hybrid polymerase comprises at least ten hybrid positions, typically at least twenty hybrid positions, or at least thirty hybrid positions, or at least forty hybrid positions, or at least fifty or more hybrid positions, that are mutated from the native reside of SEQ ID NO:24 or SEQ ID NO:25 to the corresponding residue of SEQ ID NO:25 or SEQ ID NO:24, respectively.

In other embodiments, the hybrid polymerase comprises an anino acid sequence of SEQ ID NO:2, SEQ ID NO:12, SEQ ID NO:16, or SEQ ID NO:18; or the polymerase region of SEQ ID NO:4, SEQ ID NO:6, SEQ ID NO:8, SEQ ID NO:10, SEQ ID NO:14, or SEQ ID NO:20

The invention also includes embodiments in which the hybrid polymerase further comprises a DNA binding domain, often Sso7d, Sac7d, and Sac7e. Often, the DNA binding domain is conjugated to the polymerase. In some embodiments, the polymerase DNA binding domain conjugate comprises an amino acid sequence of SEQ ID NO:4, SEQ ID NO:6, SEQ ID NO:8, SEQ ID NO:10, SEQ ID NO:14, or SEQ ID NO:20.

The invention also provides isolated nucleic acids encoding the hybrid polymerases, and conjugates comprising the hybrid polymerase linked to a DNA binding domain; and expression vectors and host cells comprising the nucleic acids.

In another aspect, the invention provides an isolated nucleic acid encoding a polypeptide comprising an amino acid sequence at least 94% identical to SEQ ID NO:2, wherein the polypeptide exhibits polymerase activity. In typical embodiments, the polypeptide comprises SEQ ID NO:2. In some embodiments, the isolated nucleic acid comprises SEQ ID NO:1.

The invention also provides embodiments, wherein the polypeptide encoded by the nucleic acid further comprises a DNA binding domain, which is often selected from the group consisting of Sso7d, Sac7d, and Sac7e. The nucleic acid can encode a polypeptide comprising SEQ ID NO:4. In one embodiment, the nucleic acid comprises SEQ ID NO:3.

In other aspects, the invention provides expression vectors and host cells comprising the nucleic acids.

In another aspect, the invention provides an isolated polypeptide comprising an amino acid sequence at least 94% identical to SEQ ID NO:2, wherein the polypeptide has polymerase activity. In one embodiment, the polypeptide comprises SEQ ID NO:2.

In some embodiments, the polypeptide further comprises a DNA-binding domain, e.g., Sso7d, Sac7d, or Sac7e. The DNA-binding domain can be fused to the carboxy-terminus of the polypeptide. In one embodiment, the polypeptide comprises SEQ ID NO:4.

In another aspect, the invention provides an isolated nucleic acid encoding a polypeptide comprising an amino acid sequence at least 94% identical to SEQ ID NO:12, SEQ ID NO:16, or SEQ ID NO:18; or the polymerase region of SEQ ID NO:6, SEQ ID NO:8, SEQ ID NO:10, SEQ ID NO:14, or SEQ ID NO:20, wherein the polypeptide exhibits polymerase activity. In typical embodiments, the polypeptide comprises SEQ ID NO:12, SEQ ID NO:16, or SEQ ID NO:18; or the polymerase region of SEQ ID NO:6, SEQ ID NO:8, SEQ ID NO:10, SEQ ID NO:14, or SEQ ID NO:20. In some embodiments, the isolated nucleic acid comprises SEQ ID NO:11, SEQ ID NO:15, or SEQ ID NO:17; or the polymerase region of SEQ ID NO:5, SEQ ID NO:7, SEQ ID NO:9, SEQ ID NO:13, or SEQ ID NO:19.

The invention also provides embodiments, wherein the polypeptide encoded by the nucleic acid further comprises a DNA binding domain, which is often selected from the group consisting of Sso7d, Sac7d, and Sac7e. The nucleic acid can encode a polypeptide comprising SEQ ID NO:6, SEQ ID NO:8, SEQ ID NO:10, SEQ ID NO:14, or SEQ ID NO:20. In one embodiment, the nucleic acid comprises SEQ ID NO:5, SEQ ID NO:7, SEQ ID NO:9, SEQ ID NO:13, or SEQ ID NO:1.

In other aspects, the invention provides expression vectors and host cells comprising the nucleic acids.

In another aspect, the invention provides an isolated polypeptide comprising an amino acid sequence at least 94% identical to SEQ ID NO:12, SEQ ID NO:16, or SEQ ID NO:18; or the polymerase region of SEQ ID NO:6, SEQ ID NO:8, SEQ ID NO:10, SEQ ID NO:14, or SEQ ID NO:20, wherein the polypeptide has polymerase activity. In one embodiment, the polypeptide comprises SEQ ID NO:12, SEQ ID NO:16, or SEQ ID NO:18; or the polymerase region of SEQ ID NO:6, SEQ ID NO:8, SEQ ID NO:10, SEQ ID NO:14, or SEQ ID NO:20.

In some embodiments, the further comprising a DNA binding domain, e.g., Sso7d, Sac7d, or Sac7e. The DNA binding domain can be fused to the carboxy-terminus of the polypeptide. In one embodiment, the polypeptide comprises SEQ ID NO:6, SEQ ID NO:8, SEQ ID NO:10, SEQ ID NO:14, or SEQ ID NO:20.

BRIEF DESCRIPTION OF THE DRAWINGS

FIG. 1 shows an alignment of the parent Pfu (SEQ ID NO:24) and Deep Vent® (SEQ ID NO:25) polymerase sequences. The hybrid protein design polymerase sequence (SEQ ID NO:27 shows the positions that vary, between the two parent sequences, which are designated by an X. "Corresponding residues" in the sequences are those residues that occur in the same position as shown in the alignment.

DETAILED DESCRIPTION OF THE INVENTION

Definitions

Figure 2:
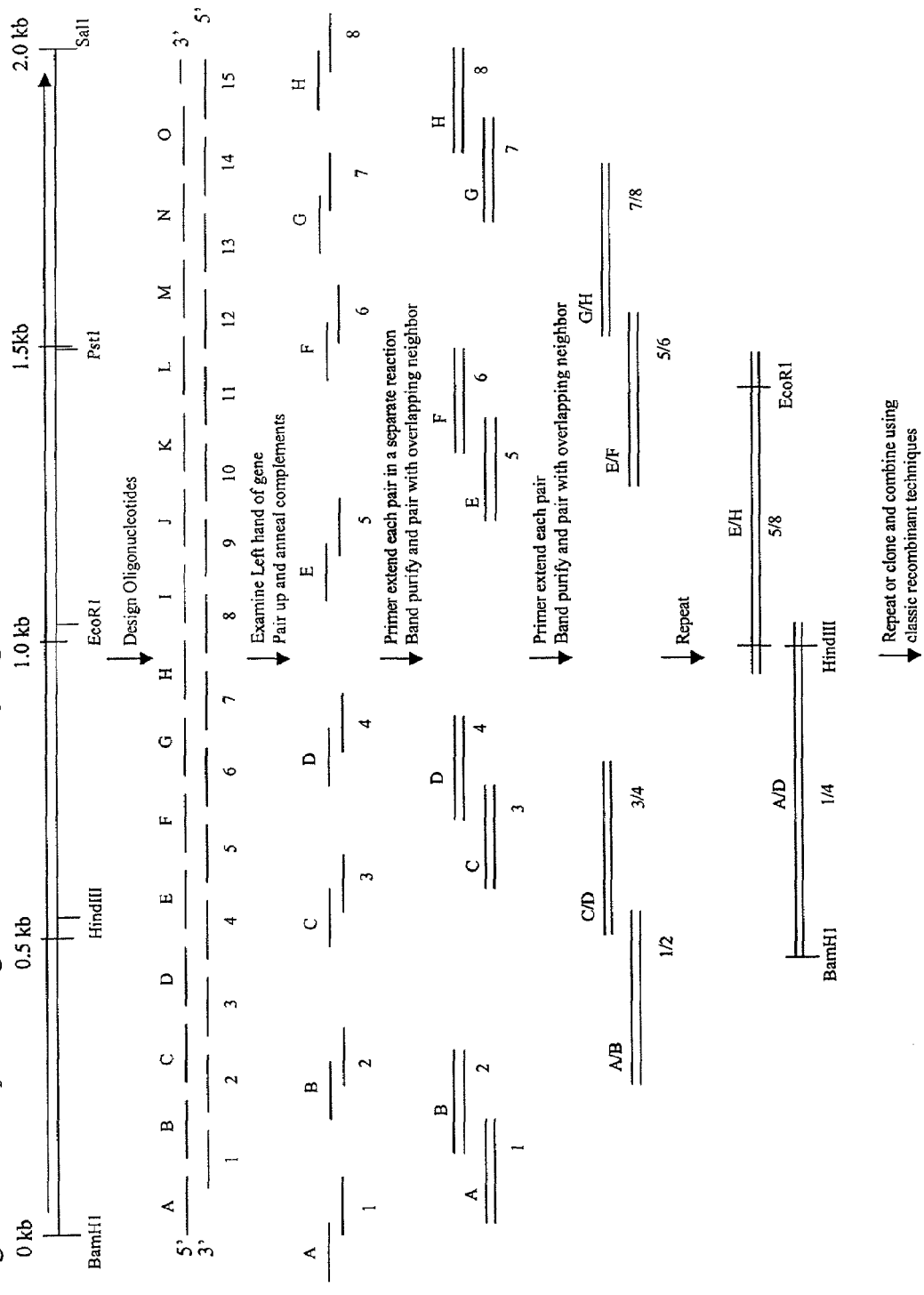
FIG. 2 shows assembly PCR of sequences encoding hybrid polymerases. In this example, 100 base pair degenerate oligonucleotides are subjected to rounds of annealing and primer extension until fragments of approximately 500 base pairs are obtained. These fragment libraries are sufficiently large in size to be easily manipulated and assembled into full length clones or libraries of full length clones by conventional molecular cloning techniques.

The term "hybrid polymerase" is used herein to describe a polymerase that comprises amino acid residues from multiple parent sequences.

The term "hybrid position" refers to a position that differs between parent polymerase sequences, or subsequences.

A "wild type polymerase" refers to a naturally occurring polymerase. A "wild type polymerase amino acid sequence" refers to the naturally occurring amino acid sequence.

A "native" polymerase sequence refers to a parent polymerase sequence, typically a "wildtype" sequence.

A "parent polymerase sequence" indicates a starting or reference amino acid or nucleic acid sequence prior to a manipulation of the invention. The term is used interchangeably with "starting sequence". Parent sequences may be wild-type proteins, proteins containing mutations, or other engineered proteins. Parent sequences can also be full-length proteins, protein subunits, protein domains, amino acid motifs, protein active sites, or any polymerase sequence or subset of polymerase sequences, whether continuous or interrupted by other polypeptide sequences.

The term "DNA binding domain" refers to a protein domain which binds with significant affinity to DNA, for which there is no known nucleic acid which binds to the protein domain with more than 100-fold more affinity than another nucleic acid with the same nucleotide composition but a different nucleotide sequence.

The term "Sso7d" or "Sso7d DNA binding domain" or "Sso7d-like DNA binding domain" or "Sso7d binding protein" refers to nucleic acid and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 15, 25, 35, 50, or more amino acids, to an Sso7d sequence of SEQ ID NO:22; (2) bind to antibodies, e.g., polyclonal antibodies, raised against an immunogen comprising an amino acid sequence of SEQ ID NO:22 and conservatively modified variants thereof; (3) specifically hybridize under stringent hybridization conditions to a Sso7d nucleic acid sequence of SEQ ID NO:21 and conservatively modified variants thereof; or (4) have a nucleic acid sequence that has greater than about 90%, preferably greater than about 96%, 97%, 98%, 99%, or higher nucleotide sequence identity, preferably over a region of at least about 50, 100, 150, or more nucleotides, to SEQ ID NO:21. The term includes both full-length Sso7d polypeptides and fragments of the polypeptides that have sequence non-specific double-stranded binding activity. Sso7d-like proteins include Sac7d and Sac7e.

"Domain" refers to a unit of a protein or protein complex, comprising a polypeptide subsequence, a complete polypeptide sequence, or a plurality of polypeptide sequences where that unit has a defined function. The function is understood to be broadly defined and can be ligand binding, catalytic activity or can have a stabilizing effect on the structure of the protein.

An "Sso7d polymerase conjugate" refers to a modified polymerase comprising at least one Sso7D DNA binding domain joined to a polymerase domain, or a catalytic subunit of the polymerase domain.

"Efficiency" in the context of a polymerase of this invention refers to the ability of the enzyme to perform its catalytic function under specific reaction conditions. Typically, "efficiency" as defined herein is indicated by the amount of product generated under given reaction conditions.

"Enhances" in the context of an enzyme refers to improving the activity of the enzyme, i.e., increasing the amount of product per unit enzyme per unit time.

"Fused" refers to linkage by covalent bonding.

"Heterologous", when used with reference to portions of a protein, indicates that the protein comprises two or more domains that are not found in the same relationship to each other in nature. Such a protein, e.g., a fusion protein, contains two or more domains from unrelated proteins arranged to make a new functional protein.

"Join" refers to any method known in the art for functionally connecting protein domains, including without limitation recombinant fusion with or without intervening domains, intein-mediated fusion, non-covalent association, and covalent bonding, including disulfide bonding; hydrogen bonding; electrostatic bonding; and conformational bonding, e.g., antibody-antigen, and biotin-avidin associations.

"Polymerase" refers to an enzyme that performs template-directed synthesis of polynucleotides. The term encompasses both the full length polypeptide and a domain that has polymerase activity.

"Processivity" refers to the ability of a polymerase to remain bound to the template or substrate and perform polynucleotide synthesis. Processivity is measured by the number of catalytic events that take place per binding event.

"Thermally stable polymerase" as used herein refers to any enzyme that catalyzes polynucleotide synthesis by addition of nucleotide units to a nucleotide chain using DNA or RNA as a template and has an optimal activity at a temperature above 45° C.

"*Thermus* polymerase" refers to a family A DNA polymerase isolated from any *Thermus* species, including without limitation *Thermus aquaticus, Thermus brockianus*, and *Thermus thermophilus*; any recombinant polymerases deriving from *Thermus* species, and any functional derivatives thereof, whether derived by genetic modification or chemical modification or other methods known in the art.

The term "amplification reaction" refers to any in vitro means for multiplying the copies of a target sequence of nucleic acid. Such methods include but are not limited to polymerase chain reaction (PCR), DNA ligase chain reaction (see U.S. Pat. Nos. 4,683,195 and 4,683,202; PCR Protocols: A Guide to Methods and Applications (Innis et al., eds, 1990)), (LCR), QBeta RNA replicase, and RNA transcription-based (such as TAS and 3SR) amplification reactions as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

"Long PCR" refers to the amplification of a DNA fragment of 5 kb or more in length. Long PCR is typically performed using specially-adapted polymerases or polymerase mixtures (see, e.g., U.S. Pat. Nos. 5,436,149 and 5,512,462) that are distinct from the polymerases conventionally used to amplify shorter products.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra.

A "temperature profile" refers to the temperature and lengths of time of the denaturation, annealing and/or extension steps of a PCR or cycle sequencing reaction. A temperature profile for a PCR or cycle sequencing reaction typically consists of 10 to 60 repetitions of similar or identical shorter temperature profiles; each of these shorter profiles may typically define a two step or three-step cycle. Selection of a temperature profile is based on various considerations known to those of skill in the art, see, e.g., Innis et al., supra. In a long PCR reaction as described herein, the extension time required to obtain an amplification product of 5 kb or greater in length is reduced compared to conventional polymerase mixtures.

PCR "sensitivity" refers to the ability to amplify a target nucleic acid that is present in low copy number. "Low copy number" refers to $10^5$, often $10^4$, $10^3$, $10^2$, $10^1$ or fewer, copies of the target sequence in the nucleic acid sample to be amplified.

The term "polymerase primer/template binding specificity" as used herein refers to the ability of a polymerase to discriminate between correctly matched primer/templates and mismatched primer templates. An "increase in polymerase primer/template binding specificity" in this context refers to an increased ability of a polymerase of the invention to discriminate between matched primer/template in comparison to a wild type polymerase protein.

A "template" refers to a double stranded polynucleotide sequence that comprises the polynucleotide to be amplified, flanked by primer hybridization sites. Thus, a "target template" comprises the target polynucleotide sequence flanked by hybridization sites for a 5' primer and a 3' primer.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

For example, substitutions may be made wherein an aliphatic amino acid (G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, E or D, may be substituted with its uncharged counterpart, Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins (1984)).

The term "encoding" refers to a polynucleotide sequence encoding one or more amino acids. The term does not require a start or stop codon. An amino acid sequence can be encoded in any one of six different reading frames provided by a polynucleotide sequence.

The term "promoter" refers to regions or sequence located upstream and/or downstream from the start of transcription and which are involved in recognition and binding of RNA polymerase and other proteins to initiate transcription.

A "vector" refers to a polynucleotide, which when independent of the host chromosome, is capable replication in a host organism. Preferred vectors include plasmids and typically have an origin of replication. Vectors can comprise, e.g., transcription and translation terminators, transcription and translation initiation sequences, and promoters useful for regulation of the expression of the particular nucleic acid.

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)) of an isolated nucleic acid comprising the expression cassette. In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

A "polymerase nucleic acid" or "polymerase polynucleotide" is a polynucleotide sequence or subsequence encoding a polymerase. Exemplary polymerase nucleic acids of the invention are identical or substantially identical to a polymerase sequence set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19; which encodes a polymerase polypeptide identical or substantially identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20.

A "polymerase polypeptide" of the present invention is a protein comprising a polymerase domain. The polymerase polypeptide may also comprise additional domains including a DNA binding domain, e.g., Sso7D. DNA polymerases are well-known to those skilled in the art, e.g., *Pyrococcus furiosus, Thermococcus litoralis*, and *Thermotoga maritima*. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

Exemplary embodiments of polymerases of the present invention include a polymerase identical or substantially identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20. A skilled practitioner will understand that specific amino acid residues within the polymerases can be modified, e.g., conservatively modified, without significantly affecting the improved polymerase ability. On average, there are at least 6 amino acids per 100 that can be modified. They include, for example, replacing glycine at position 12 with alanine, methionine at position 1 with valine, isoleucine at position 2 with leucine, isoleucine at position 8 with valine, or threonine at position 33 with serine. (Positions are indicated with reference to SEQ ID NO:26.)

The polymerases of the present invention may be identified by their ability to bind to antibodies, e.g., polyclonal antibodies, raised against an immunogen comprising an amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 and conservatively modified variants thereof.

Polypeptide polymerases of the present invention have polymerase activity. Using the assays described herein, the activity of the polypeptides of the present invention can be measured. Some polymerase polypeptides of the invention exhibit improved polymerase activity as compared to wild type polymerases in the assays described herein.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection.

When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988) e.g., as implemented in the program PC/GENE (Intelligenetics, Mountain View, Calif., USA).

The term "substantial identity" of polynucleotide sequences means that a polynucleotide comprises a sequence that has at least 70% sequence identity. More preferred embodiments include at least: 75%, 80%, 85%, 90%, 94%, 95%, 96%, 97%, 98%, or 99% compared to a reference sequence using the programs described herein; preferably BLAST using standard parameters, as described below. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 94%. More preferred embodiments include at least 94%, 95%, 96%, 97%, 98% or 99%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine. The term "at least 94% identical" refers to a sequence that is at least 94%, possibly 95%, 96%, 97%, 98%, 99% or 100% identical to a reference sequence.

One of skill in the art will recognize that two polypeptides can also be "substantially identical" if the two polypeptides are immunologically similar. Thus, overall protein structure may be similar while the primary structure of the two polypeptides display significant variation. Therefore a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl Math*. 2:482 (1981), by the homology alignment algorithm of Needleman & Wunsch, *J. Mol. Biol*. 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol*. 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol*. 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5-10° C. lower than the thermal melting point ($T_m$) for the specific sequence at a defined ionic strength pH. Low stringency conditions are generally selected to be about 15-30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Hybridization conditions are typically those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions"

include a hybridization in a buffer of 40% formamide, 1 M NaCl, 1% SDS at 37° C., and a wash in 1×SSC at 45° C. Exemplary "stringent hybridization conditions" include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

Introduction

The present invention provides novel polymerase polypeptide and nucleic cid sequences. In some embodiments, the polypeptides further comprise a DNA binding domain, e.g., an Archaeal small basic protein, such as an Sso7d, Sac7d, or Sac7e DNA binding domain, which is fused to the polypeptide. The DNA binding domain typically increases the binding affinity of the enzyme to nucleic acid and can enhance the processivity of the polymerases.

A polymerase of the invention includes polymerases identical or substantially identical to the polymerase sequences disclosed in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20.

Polymerases of the invention exhibit the same or altered polymerase activity compared to that of wild type polymerase, e.g., Pfu or Deep Vent® polymerase, in accordance with the activity assays described herein.

Generation of Nucleic Acids Encoding polymerases

Polymerases of the present invention can be produced by methods known to those of skill in the art. For example, the nucleic acid sequences encoding a Phy1 or PhS1 polymerase of the invention are provided as SEQ ID NO:1 and SEQ ID NO:3 and the amino acid sequences of a Phy1 or PhS1 polymerase are provided as SEQ ID NO:2 and SEQ ID NO:4. Polymerases, or subsequences thereof, may be synthesized using recombinant DNA methodology. Generally this involves creating a DNA sequence that encodes the polypeptide, modified as desired, placing the DNA in an expression cassette under the control of a particular promoter, expressing the protein in a host, isolating the expressed protein and, if required, renaturing the protein.

Polynucleotides may also be synthesized by well-known techniques as described in the technical literature. See, e.g., Carruthers et al., *Cold Spring Harbor Symp. Quant. Biol.* 47:411-418 (1982), and Adams et al., *J. Am. Chem. Soc.* 105:661 (1983). Double stranded DNA fragments may then be obtained either by synthesizing the complementary strand and annealing the strands together under appropriate conditions, or by synthesizing the complementary strand using DNA polymerase with an appropriate primer sequence. Polymerases may also be ordered from a variety of commercial sources known to persons of skill.

Assembly PCR can be used, in a process that involves the assembly of a PCR product from a mixture of small DNA fragments. A large number of different PCR reactions can occur in parallel in the same reaction mixture, with the products of one reaction priming the products of another reaction. Alternatively, the skilled practitioner, using assembly PCR, can completely synthesize the claimed nucleotide sequences.

B. Generation of a Polymerase Nucleic Acid by Modification of Wild Type

Wild type polymerase nucleic acids may be isolated from naturally occurring sources to be used as starting material to generate novel polymerases. Generally, the nomenclature and the laboratory procedures in recombinant DNA technology described below are those well known and commonly employed in the art. Standard techniques for cloning, DNA and RNA isolation, amplification and purification are known. Generally enzymatic reactions involving DNA ligase, DNA polymerase, restriction endonucleases are the like are performed according to the manufacturer's specifications. These techniques and various other techniques are generally performed according to Sambrook & Russell, Molecular Cloning—A Laboratory Manual, Cold Spring Harbor Laboratory, Cold Spring Harbor, N.Y., (1989) or Current Protocols in Molecular Biology Volumes 1-3, John Wiley & Sons, Inc. (1994-1998) ("Ausubel et al.").

The isolation of polymerase nucleic acids may be accomplished by a variety of techniques. For instance, genes encoding Pfu or Deep Vents® can be constructed as described in U.S. Pat. Nos. 5,948,663 and 5,834,285.

The polymerase nucleic acids of the present invention can be generated from the wild type sequences. The wild type sequences are altered to create modified sequences. Wild type polymerases can be readily modified to create the polymerases claimed in the present application using methods that are well known in the art. Exemplary modification methods are site-directed mutagenesis, point mismatch repair, or oligonucleotide-directed mutagenesis. Polymerase polynucleotides of the invention, e.g., SEQ ID NO:1 or SEQ ID NO:3, can also be readily altered using these modification methods.

While distinctions and classifications are made in the course of the ensuing discussion for clarity, it will be appreciated that many modification techniques exist and are often not mutually exclusive. Indeed, the various methods can be used singly or in combination, in parallel or in series, to access polymerases of the present invention.

The result of any of the modification procedures described herein can be the generation of one or more nucleic acids, which can be selected or screened for nucleic acids that encode proteins with polymerase activity. Following modification of a polymerase, e.g., a wild type polymerase, or hybrid polymerase such as SEQ ID NO:2 or SEQ ID NO:4, by one or more of the methods herein, or otherwise available to one of skill, any nucleic acids that are produced can be selected for a desired activity or property, e.g. polymerase activity. This can include identifying any activity that can be detected by any of the assays known in the art for determining polymerase activity.

Site directed mutagenesis is well known in the art and is described in the following references, e.g., (Ling et al. (1997) "Approaches to DNA mutagenesis: an overview" *Anal Biochem.* 254(2): 157-178; Dale et al. (1996) "Oligonucleotide-directed random mutagenesis using the phosphorothioate method" *Methods Mol. Biol.* 57:369-374; Smith (1985) "In vitro mutagenesis" *Ann. Rev. Genet.* 19:423-462; Botstein & Shortle (1985) "Strategies and applications of in vitro mutagenesis" *Science* 229:1193-1201; Carter (1986) "Site-directed mutagenesis" *Biochem. J.* 237:1-7; and Kunkel (1987) "The efficiency of oligonucleotide directed mutagenesis" in *Nucleic Acids & Molecular Biology* (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" *Proc. Natl. Acad. Sci. USA* 82:488-492; Kunkel et al. (1987) "Rapid and efficient site-specific mutagenesis without phenotypic selection" *Methods in Enzymol.* 154, 367-382; and Bass et al. (1988) "Mutant Trp repressors with new DNA-binding specificities" Science 242:240-245); oligonucleotide-directed mutagenesis (*Methods in Enzymol.* 100: 468-

500 (1983); *Methods in Enzymol* 154: 329-350 (1987); Zoller & Smith (1982) "Oligonucleotide-directed mutagenesis using M13-derived vectors: an efficient and general procedure for the production of point mutations in any DNA fragment" *Nucleic Acids Res*. 10:6487-6500; Zoller & Smith (1983) "Oligonucleotide-directed mutagenesis of DNA fragments cloned into M13 vectors" *Methods in Enzymol*. 100: 468-500; and Zoller & Smith (1987) "Oligonucleotide-directed mutagenesis: a simple method using two oligonucleotide primers and a single-stranded DNA template" *Methods in Enzymol*. 154:329-350); phosphorothioate-modified DNA mutagenesis (Taylor et al. (1985) "The use of phosphorothioate-modified DNA in restriction enzyme reactions to prepare nicked DNA" *Nucl. Acids Res*. 13: 8749-8764; Taylor et al. (1985) "The rapid generation of oligo-nucleotide-directed mutations at high frequency using phosphorothioate-modified DNA" *Nucl. Acids Res*. 13: 8765-8787 (1985); Nakamaye & Eckstein (1986) "Inhibition of restriction endonuclease Nci I cleavage by phosphorothioate groups and its application to oligonucleotide-directed mutagenesis" *Nucl. Acids Res*. 14: 9679-9698; Sayers et al. (1988) "Y-T Exonucleases in phosphorothioate-based oligo-nucleotide-directed mutagenesis" *Nucl. Acids Res*. 16:791-802; and Sayers et al. (1988) "Strand specific cleavage of phosphorothioate-containing DNA by reaction with restriction endonucleases in the presence of ethidium bromide" *Nucl. Acids Res*. 16: 803-814); mutagenesis using gapped duplex DNA (Kramer et al. (1984) "The gapped duplex DNA approach to oligonucleotide-directed mutation construction" *Nucl. Acids Res*. 12: 9441-9456; Kramer & Fritz (1987) *Methods in Enzymol*. "Oligonucleotide-directed construction of mutations via gapped duplex DNA" 154:350-367; Kramer et al. (1988) "Improved enzymatic in vitro reactions in the gapped duplex DNA approach to oligonucleotide-directed construction of mutations" *Nucl. Acids Res*. 16: 7207; and Fritz et al. (1988) "Oligonucleotide-directed construction of mutations: a gapped duplex DNA procedure without enzymatic reactions in vitro" *Nucl. Acids Res*. 16: 6987-6999).

An additional modification method well known in the art is point mismatch repair, e.g., (Kramer et al. (1984) "Point Mismatch Repair" *Cell* 38:879-887), mutagenesis using repair-deficient host strains (Carter et al. (1985) "Improved oligonucleotide site-directed mutagenesis using M13 vectors" *Nucl. Acids Res*. 13: 4431-4443; and Carter (1987) "Improved oligonucleotide-directed mutagenesis using M13 vectors" *Methods in Enzymol*. 154: 382-403), deletion mutagenesis (Eghtedarzadeh & Henikoff (1986) "Use of oligonucleotides to generate large deletions" *Nucl. Acids Res*. 14: 5115), restriction-selection and restriction-selection and restriction-purification (Wells et al. (1986) "Importance of hydrogen-bond formation in stabilizing the transition state of subtilisin" *Phil. Trans. R. Soc. Lond*. A 317: 415-423), mutagenesis by total gene synthesis (Nambiar et al. (1984) "Total synthesis and cloning of a gene coding for the ribonuclease S protein" *Science* 223: 1299-1301; Sakamar and Khorana (1988) "Total synthesis and expression of a gene for the a-subunit of bovine rod outer segment guanine nucleotide-binding protein (transducing)" *Nucl. Acids Res*. 14: 6361-6372; Wells et al (1985) "Cassette mutagenesis: an efficient method for generation of multiple mutations at defined sites" *Gene* 34:315-323; and Grundstrom et al. (1985) "Oligonucleotide-directed mutagenesis by microscale 'shotgun' gene synthesis" *Nucl. Acids Res*. 13: 3305-3316), double-strand break repair (Mandecki (1986); Arnold (1993) "Protein engineering for unusual environments" *Current Opinion in Biotechnology* 4:450-455. "Oligonucleotide-directed double-strand break repair in plasmids of *Escherichia coli*: a method for site-specific mutagenesis" *Proc. Natl. Acad. Sci. USA*, 83:7177-7181). Additional details on many of the above methods can be found in *Methods in Enzymology* Volume 154, which also describes useful controls for trouble-shooting problems with various mutagenesis methods.

Oligonucleotide directed mutagenesis could be used to introduce site-specific mutations in a nucleic acid sequence of interest. Examples of such techniques are found in the references above and, e.g., in Reidhaar-Olson et al. (1988) *Science* 241:53-57. Similarly, cassette mutagenesis can be used in a process that replaces a small region of a double stranded DNA molecule with a synthetic oligonucleotide cassette that differs from the native sequence. The oligonucleotide can contain, e.g., completely and/or partially randomized native sequence(s).

Modification of Polymerase Nucleic Acids for Common Codon Usage in an Organism

The polynucleotide sequence encoding a particular polymerase can be altered to coincide with the codon usage of a particular host. For example, the codon usage of *E. coli* can be used to derive a polynucleotide that encodes a polymerase polypeptide of the invention and comprises preferred *E. coli* codons. The frequency of preferred codon usage exhibited by a host cell could be calculated by averaging frequency of preferred codon usage in a large number of genes expressed by the host cell.

When synthesizing a gene for improved expression in a host cell, it is desirable to design the gene such that its frequency of codon usage approaches the frequency of preferred codon usage of the host cell. The percent deviation of the frequency of preferred codon usage for a synthetic gene from that employed by a host cell is calculated by first determining the percent deviation of the frequency of usage of a single codon from that of the host followed by obtaining the average deviation over all codons.

DNA Binding Domains of the Present Invention

In some embodiments, the novel polymerases are conjugated to a DNA binding domain. A DNA binding domain is a protein, or a defined region of a protein, that binds to nucleic acid in a sequence-independent matter, e.g., binding does not exhibit a gross preference for a particular sequence. DNA binding domains may be single or double stranded.

The DNA binding proteins are preferably thermostable. Examples of such proteins include, but are not limited to, the Archaeal small basic DNA binding proteins Sso7D and Sso7D-like proteins(see, e.g., Choli et al., *Biochimica et Biophysica Acta* 950:193-203, 1988; Baumann et al., *Structural Biol*. 1:808-819, 1994; and Gao et al, *Nature Struc. Biol*. 5:782-786, 1998), Archaeal HMf-like proteins (see, e.g., Starich et al., *J. Molec. Biol*. 255:187-203, 1996; Sandman et al., *Gene* 150:207-208, 1994), and PCNA homologs (see, e.g., Cann et al., *J. Bacteriology* 181:6591-6599, 1999; Shamoo and Steitz, *Cell*:99, 155-166, 1999; De Felice et al., *J. Molec. Biol*. 291, 47-57, 1999; and Zhang et al., *Biochemistry* 34:10703-10712, 1995).

Sso7d and Sso7d-like proteins, Sac7d and Sac7d-like proteins, e.g., Sac7a, Sac7b, Sac7d, and Sac7e are small (about 7,000 kd MW), basic chromosomal proteins from the hyperthermophilic archaebacteria *Sulfolobus solfataricus* and *S. acidocaldarius*, respectively. These proteins are lysine-rich and have high thermal, acid and chemical stability. They bind DNA in a sequence-independent manner and when bound, increase the $T_M$ of DNA by up to 40° C. under some conditions (McAfee et al., *Biochemistry* 34:10063-10077, 1995). These proteins and their homologs are typically believed to be involved in stabilizing genomic DNA at elevated temperatures. Suitable Sso7d-like DNA binding domains for use in the invention can be modified based on their sequence homology to Sso7d. Typically, DNA binding domains that are identical to or substantially identical to a known DNA binding protein over a comparison window of about 25 amino acids, optionally about 50-100 amino acids, or the length of the entire protein, can be used in the invention. The sequence can be compared and aligned for maximum correspondence over a comparison window, or designated region as measured using one of the described comparison algorithms or by manual alignment and visual inspection. For purposes of this patent, percent amino acid identity is determined by the default parameters of BLAST.

The HMf-like proteins are archaeal histones that share homology both in amino acid sequences and in structure with eukaryotic H4 histones, which are thought to interact directly with DNA. The HMf family of proteins form stable dimers in solution, and several HMf homologs have been identified from thermostable species (e.g., *Methanothermus fervidus* and *Pyrococcus* strain GB-3a). The HMf family of proteins, once joined to Taq DNA polymerase or any DNA modifying enzyme with a low intrinsic processivity, can enhance the ability of the enzyme to slide along the DNA substrate and thus increase its processivity. For example, the dimeric HMf-like protein can be covalently linked to the N terminus of Taq DNA polymerase, e.g., via chemical modification, and thus improve the processivity of the polymerase.

Certain helix-hairpin-helix motifs have been shown to bind DNA nonspecifically and enhance the processivity of a DNA polymerase to which it is fused (Pavlov et al., *Proc Natl Acad Sci USA*. 99:13510-5, 2002).

Many but not all family B DNA polymerases interact with accessory proteins to achieve highly processive DNA synthesis. A particularly important class of accessory proteins is referred to as the sliding clamp. Several characterized sliding clamps exist as trimers in solution, and can form a ring-like structure with a central passage capable of accommodating double-stranded DNA. The sliding clamp forms specific interactions with the amino acids located at the C terminus of particular DNA polymerases, and tethers those polymerases to the DNA template during replication. The sliding clamp in eukarya is referred to as the proliferating cell nuclear antigen (PCNA), while similar proteins in other domains are often referred to as PCNA homologs. These homologs have marked structural similarity but limited sequence similarity.

Recently, PCNA homologs have been identified from thermophilic Archaea (e.g., *Pyroccocus furiosus*). Some family B polymerases in Archaea have a C terminus containing a consensus PCNA-interacting amino acid sequence and are capable of using a PCNA homolog as a processivity factor (see, e.g., Cann et al., *J. Bacteriol*. 181:6591-6599, 1999 and De Felice et al., *J. Mol. Biol*. 291:47-57, 1999). These PCNA homologs are useful DNA binding domains for the invention. For example, a consensus PCNA-interacting sequence can be joined to a polymerase that does not naturally interact with a PCNA homolog, thereby allowing a PCNA homolog to serve as a processivity factor for the polymerase. By way of illustration, the PCNA-interacting sequence from *Pyrococcus furiosus* PolII (a heterodimeric DNA polymerase containing two family B-like polypeptides) can be covalently joined to *Pyrococcus furiosus* PolI (a monomeric family B polymerase that does not normally interact with a PCNA homolog). The resulting fusion protein can then be allowed to associate non-covalently with the *Pyrococcus furiosus* PCNA homolog to generate a novel heterologous protein with increased processivity relative to the unmodified *Pyrococcus furiosus* PolI.

Additional DNA binding domains suitable for use in the invention can be identified by homology with known DNA binding proteins and/or by antibody crossreactivity, or may be found by means of a biochemical assay. DNA binding domains may be synthesized or isolated using the techniques described above.

Joining a DNA Binding Domain to a Polymerase

The DNA binding domain and the polymerase domain of the conjugate or fusion proteins of the invention can be joined by methods well known to those of skill in the art. These methods include both chemical and recombinant means.

Chemical means of joining a DNA binding protein to a polymerase domain are described, e.g., in *Bioconjugate Techniques*, Hermanson, Ed., Academic Press (1996). These include, for example, derivitization for the purpose of linking the two proteins to each other, either directly or through a linking compound, by methods that are well known in the art of protein chemistry. For example, in one chemical conjugation embodiment, the means of linking the catalytic domain and the DNA binding domain comprises a heterobifunctional-coupling reagent which ultimately contributes to formation of an intermolecular disulfide bond between the two moieties. Other types of coupling reagents that are useful in this capacity for the present invention are described, for example, in U.S. Pat. No. 4,545,985. Alternatively, an intermolecular disulfide may conveniently be formed between cysteines in each moiety, which occur naturally or are inserted by genetic engineering. The means of linking moieties may also use thioether linkages between heterobifunctional crosslinking reagents or specific low pH cleavable crosslinkers or specific protease cleavable linkers or other cleavable or noncleavable chemical linkages.

The means of linking a DNA binding domain, e.g., Sso7d, and a polymerase domain may also comprise a peptidyl bond formed between moieties that are separately synthesized by standard peptide synthesis chemistry or recombinant means. The conjugate protein itself can also be produced using chemical methods to synthesize an amino acid sequence in whole or in part. For example, peptides can be synthesized by solid phase techniques, such as, e.g., the Merrifield solid phase synthesis method, in which amino acids are sequentially added to a growing chain of amino acids (see, Merrifield (1963) *J. Am. Chem. Soc.*, 85:2149-2146). Equipment for automated synthesis of polypeptides is commercially available from suppliers such as PE Corp. (Foster City, Calif.), and may generally be operated according to the manufacturer's instructions. The synthesized peptides can then be cleaved from the resin, and purified, e.g., by preparative high performance liquid chromatography (see Creighton, *Proteins Structures and Molecular Principles*, 50-60 (1983)). The composition of the synthetic polypeptides or of subfragments of the polypeptide, may be confirmed by amino acid analysis or sequencing (e.g., the Edman degradation procedure; see Creighton, *Proteins, Structures and Molecular Principles*, pp. 34-49 (1983)).

In addition, nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxy-proline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In another embodiment, a DNA binding domain and polymerase domain can be joined via a linking group. The linking group can be a chemical crosslinking agent, including, for example, succinimidyl-(N-maleimidomethyl)-cyclohexane-1-carboxylate (SMCC). The linking group can also be an additional amino acid sequence(s), including, for example, a polyalanine, polyglycine or similarly, linking group.

In some embodiments, the coding sequences of each polypeptide in a resulting fusion protein are directly joined at their amino- or carboxy-terminus via a peptide bond in any order. Alternatively, an amino acid linker sequence may be employed to separate the first and second polypeptide components by a distance sufficient to ensure that each polypeptide folds into its secondary and tertiary structures. Such an amino acid linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Typical peptide linker sequences contain Gly, Ser, Val and Thr residues. Other near neutral amino acids, such as Ala can also be used in the linker sequence. Amino acid sequences which may be usefully employed as linkers include those disclosed in Maratea et al. (1985) Gene 40:39-46; Murphy et al. (1986) Proc. Natl. Acad. Sci. USA 83:8258-8262; U.S. Pat. Nos. 4,935,233 and 4,751,180. The linker sequence may generally be from 1 to about 50 amino acids in length, e.g., 3, 4, 6, or 10 amino acids in length, but can be 100 or 200 amino acids in length. Linker sequences may not be required when the first and second polypeptides have non-essential N-terminal amino acid regions that can be used to separate the functional domains and prevent steric interference.

Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Ala. These linkers optionally have amide linkages, sulfhydryl linkages, or heterobifunctional linkages.

Other methods of joining a DNA binding domain and polymerase domain include ionic binding by expressing negative and positive tails and indirect binding through antibodies and streptavidin-biotin interactions. (See, e.g., *Bioconjugate Techniques*, supra). The domains may also be joined together through an intermediate interacting sequence. For example, an Sso7D-interacting sequence, i.e., a sequence that binds to Sso7D, can be joined to a polymerase. The resulting fusion protein can then be allowed to associate non-covalently with the Sso7D to generate an Sso7D-polymerase conjugate.

Production of Polypeptides Using Recombinant Techniques

As previously described, nucleic acids encoding the polymerase or DNA binding domains can be obtained using routine techniques in the field of recombinant genetics. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994-1999).

In one example of obtaining a nucleic acid encoding a Sso7d domain using PCR for use in the present invention, the nucleic acid sequence or subsequence is PCR amplified, using a sense primer containing one restriction site and an antisense primer containing another restriction site. This will produce a nucleic acid encoding the desired domain sequence or subsequence and having terminal restriction sites. This nucleic acid can then be easily ligated into a vector containing a nucleic acid encoding a second domain, e.g., polymerase domain, and having the appropriate corresponding restriction sites. The domains can be directly joined or may be separated by a linker, or other, protein sequence. Suitable PCR primers can be determined by one of skill in the art using the sequence information provided in GenBank or other sources. Appropriate restriction sites can also be added to the nucleic acid encoding the protein or protein subsequence by site-directed mutagenesis. The plasmid containing the domain-encoding nucleotide sequence or subsequence is cleaved with the appropriate restriction endonuclease and then ligated into an appropriate vector for amplification and/or expression according to standard methods.

Examples of techniques sufficient to direct persons of skill through in vitro amplification methods are described above and found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) C&EN 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

One of skill will recognize that modifications can additionally be made to the polymerases of the present invention without diminishing their biological activity. Some modifications may be made to facilitate the cloning, expression, or incorporation of a domain into a fusion protein. Such modifications are well known to those of skill in the art and include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences.

One or more of the domains may also be modified to facilitate the linkage of a variant polymerase domain and DNA binding domain to obtain the polynucleotides that encode the fusion polymerases of the invention. Thus, DNA binding domains and polymerase domains that are modified by such methods are also part of the invention. For example, a codon for a cysteine residue can be placed at either end of a domain so that the domain can be linked by, for example, a sulfide linkage. The modification can be performed using either recombinant or chemical methods (see, e.g., Pierce Chemical Co. catalog, Rockford Ill.).

The DNA binding and polymerase domains comprised by a recombinant fusion protein are often joined by linker domains, usually polypeptide sequences including Gly, Ser, Ala, and Val such as those described above. In some embodiments, proline residues are incorporated into the linker to prevent the formation of significant secondary structural elements by the linker.

Expression Cassettes and Host Cells for Expressing Polypeptides

The polymerases of the present invention can be expressed in a variety of host cells, including *E. coli*, other bacterial hosts, yeasts, filamentous fungi, and various higher eukaryotic cells such as the COS, CHO and HeLa cells lines and myeloma cell lines. Techniques for gene expression in microorganisms are described in, for example, Smith, *Gene Expression in Recombinant Microorganisms* (*Bioprocess Technology*, Vol. 22), Marcel Dekker, 1994. Examples of bacteria that are useful for expression include, but are not limited to, *Escherichia, Enterobacter, Azotobacter, Erwinia, Bacillus, Pseudomonas, Klebsielia, Proteus, Salmonella, Serratia, Shigella, Rhizobia, Vitreoscilla*, and *Paracoccus*. Filamentous fungi that are useful as expression hosts include, for example, the following genera: *Aspergillus, Trichoderma, Neurospora, Penicillium, Cephalosporium, Achlya, Podospora, Mucor, Cochliobolus*, and *Pyricularia*. See, e.g., U.S. Pat. No. 5,679,543 and Stahl and Tudzynski, Eds., *Molecular Biology in Filamentous Fungi*, John Wiley & Sons, 1992. Synthesis of heterologous proteins in yeast is well known and described in the literature. *Methods in Yeast Genetics*, Sherman, F., et al., Cold Spring Harbor Laboratory, (1982) is a well recognized work describing the various methods available to produce the enzymes in yeast.

There are many expression systems for producing the polymerase polypeptides of the present invention that are well know to those of ordinary skill in the art. (See, e.g., *Gene Expression Systems*, Fernandex and Hoeffler, Eds. Academic Press, 1999; Sambrook $ Russell, supra; and Ausubel et al, supra.) Typically, the polynucleotide that encodes the variant polypeptide is placed under the control of a promoter that is functional in the desired host cell. An extremely wide variety of promoters are available, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the nucleic acids that encode the joined polypeptides are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Nati. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used. Standard bacterial expression vectors include plasmids such as pBR322-based plasmids, e.g., pBLUESCRIPT™, pSKF, pET23D, λ-phage derived vectors, and fusion expression systems such as GST and LacZ. Epitope tags can also be added to recombinant proteins to provide convenient methods of isolation, e.g., c-myc, HA-tag, 6-His (SEQ ID NO:47) tag, maltose binding protein, VSV-G tag, anti-DYKDDDDK (SEQ ID NO:48) tag, or any such tag, a large number of which are well known to those of skill in the art.

For expression of in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* sp. in addition to *E. coli*. These and other suitable bacterial promoters are well known in the art and are described, e.g., in Sambrook et al. and Ausubel et al. Bacterial expression systems for expressing the proteins of the invention are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available.

Eukaryotic expression systems for mammalian cells, yeast, and insect cells are well known in the art and are also commercially available. In yeast, vectors include Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Either constitutive or regulated promoters can be used in the present invention. Regulated promoters can be advantageous because the host cells can be grown to high densities before expression of the fusion polypeptides is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals.

For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l Acad. Sci. USA* 82: 1074-8). These promoters and their use are discussed in Sambrook et al., supra.

Inducible promoters for other organisms are also well known to those of skill in the art. These include, for example, the metallothionein promoter, the heat shock promoter, as well as many others.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The construction of polynucleotide constructs generally requires the use of vectors able to replicate in bacteria. Such vectors are commonly used in the art. A plethora of kits are commercially available for the purification of plasmids from bacteria (for example, EasyPrepJ, FlexiPrepJ, from Pharmacia Biotech; StrataCleanJ, from Stratagene; and, QIAexpress Expression System, Qiagen). The isolated and purified plasmids can then be further manipulated to produce other plasmids, and used to transform cells.

The polypeptides of the present invention can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al., *Bio/Technology* (1984) 2: 800; Schoner et al., *Bio/Technology* (1985) 3: 151). Polypeptides of the invention can be expressed in a variety of host cells, including *E. coli*, other bacterial hosts, yeast, and various higher eukaryotic cells such as the COS, CHO and HeLa cells lines and myeloma cell lines. The host cells can be mammalian cells, insect cells, or microorganisms, such as, for example, yeast cells, bacterial cells, or fungal cells.

Once expressed, the polypeptides can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology* Vol. 182: *Guide to Protein Purification*., Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

To facilitate purification of the polypeptides of the invention, the nucleic acids that encode the polypeptides can also include a coding sequence for an epitope or "tag" for which an affinity binding reagent is available. Examples of suitable epitopes include the myc and V-5 reporter genes; expression vectors useful for recombinant production of fusion polypeptides having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the fusion proteins of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines (SEQ ID NO:47) are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)).

One of skill in the art would recognize that after biological expression or purification, the polymerase peptide (s) may possess a conformation substantially different than the native conformations of the constituent polypeptides. In this case, it may be necessary or desirable to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.* 268: 14065-14070; Kreitman and Pastan (1993) *Bioconjug. Chem.* 4: 581-585; and Buchner et al. (1992) *Anal. Biochem.* 205: 263-270). Debinski et al., for example, describe the denaturation and reduction of inclusion body proteins in guanidine-DTE. The protein is then refolded in a redox buffer containing oxidized glutathione and L-arginine.

Assays to Evaluate Polymerase Activity

Activity of a polymerase can be measured using a variety of assays that can be used to determine processivity or modification activity of a polymerase. Improvement in activity may include both increased processivity and increased efficiency.

The polymerases of the present invention, e.g. SEQ ID NO:2 and SEQ ID NO:4, exhibit polymerase activity, e.g., processivity, primer/template binding specificity, and 3' to 5' exonuclease activity. The activities can be measured using techniques that are standard in the art.

For example, polymerase processivity can be measured by a variety of methods known to those of ordinary skill in the art. Polymerase processivity is generally defined as the number of nucleotides incorporated during a single binding event of a modifying enzyme to a primed template. For example, a 5° FAM-labeled primer is annealed to circular or linearized ssM 13mp 18 DNA to form a primed template. In measuring processivity, the primed template usually is present in significant molar excess to the polymerase so that the chance of any primed template being extended more than once by the polymerase is minimized. The primed template is therefore mixed with the polymerase at a ratio such as approximately 4000:1 (primed DNA:DNA polymerase) in the presence of buffer and dNTPs. $MgCl_2$ is added to initiate DNA synthesis. Samples are quenched at various times after initiation, and analyzed on a sequencing gel. At a polymerase concentration where the median product length does not change with time or polymerase concentration, the length corresponds to the processivity of the enzyme. The processivity of a protein of the invention, e.g., SEQ ID NO:2 or SEQ ID NO:4, is then compared to the processivity of a wild type enzyme.

Efficiency can be demonstrated by measuring the ability of an enzyme to produce product. Increased efficiency can be demonstrated by measuring the increased ability of an enzyme to produce product. Such an analysis measures the stability of the double-stranded nucleic acid duplex indirectly by determining the amount of product obtained in a reaction. For example, a PCR assay can be used to measure the amount of PCR product obtained with a short, e.g., 12 nucleotide in length, primer annealed at an elevated temperature, e.g., 50° C. In this analysis, enhanced efficiency is shown by the ability of a polymerase to produce more product in a PCR reaction using the 12 nucleotide primer annealed at 50° C.

Efficiency can also be measured, e.g., in a real-time PCR. The Ct value represents the number of cycles required to generate a detectable amount of DNA (a "detectable" amount of DNA is typically 2×, usually 5×, 10×, 100× or more above background). An efficient polymerase may be able to produce a detectable amount of DNA in a smaller number of cycles by more closely approaching the theoretical maximum amplification efficiency of PCR. Accordingly, a lower Ct value reflects a greater amplification efficiency for the enzyme.

Long PCR may be used as another method of demonstrating enhanced efficiency. For example, an enzyme with enhanced efficiency typically allows the amplification of a long amplicon (>5 kb) in a shorter extension time compared to an enzyme with relatively lower efficiency.

Assays such as salt sensitivity can also be used to demonstrate improvement in efficiency or equivalent efficiency of a polymerase of the invention. A polymerase of the present invention may exhibit increased tolerance to high salt concentrations, i.e., a processive enzyme with increased processivity can produce more product in higher salt concentrations. For example, a PCR analysis can be preformed to determine the amount of product obtained in a reaction using a polymerase of the present invention compared to a wild type polymerase in reaction conditions with high salt, e.g., 80 mM.

Other methods of assessing efficiency of the polymerases of the invention can be determined by those of ordinary skill in the art using standard assays of the enzymatic activity of a given modification enzyme.

Primer/template specificity is the ability of an enzyme to discriminate between matched primer/template duplexes and mismatched primer/template duplexes. Specificity can be determined, for example, by comparing the relative yield of two reactions, one of which employs a matched primer, and one of which employs a mismatched primer. An enzyme with increased discrimination will have a higher relative yield with the matched primer than with the mismatched primer, i.e., the ratio of the yield in the reaction using the matched primer vs. the reaction using the mismatched primer is about 1 or above. This ratio can then be compared to the yield obtained in a parallel set of reactions employing a wild type polymerase.

In other assays for improvement, the exonuclease activity of a polymerase can also be measured, as described in the "Examples" section. In some instances, desired improvements may take into account multiple functions of a polymerase. For example, one may want to tailor the ratio of exonuclease activity to polymerization activity.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1

Generation of Hybrid Polymerases

Pfu polymerase is a commercially available (Stratagene, La Jolla, Calif.) family B DNA polymerase isolated from *Pyrococcus furiosus*. Deep Vent® is a commercially available (New England Biolabs, Beverly, Mass.) family B DNA polymerase isolated from *Pyrococcus* sp. GB-D. Being 775 amino acids in length, these proteins are twice as large as a typical protein. They share a variety of activities including DNA binding, nucleotide binding, nucleotide addition, pyrophosphorolysis, and 3' to 5' exonuclease (proofreading) activities. The method of generating a hybrid polymerase can be applied to any one of the activities encoded by these large proteins by being applied to one domain of the protein. In this example, the method was applied to each of the different enzymatic activities, by making a hybrid library for the entire protein.

Figure 1:
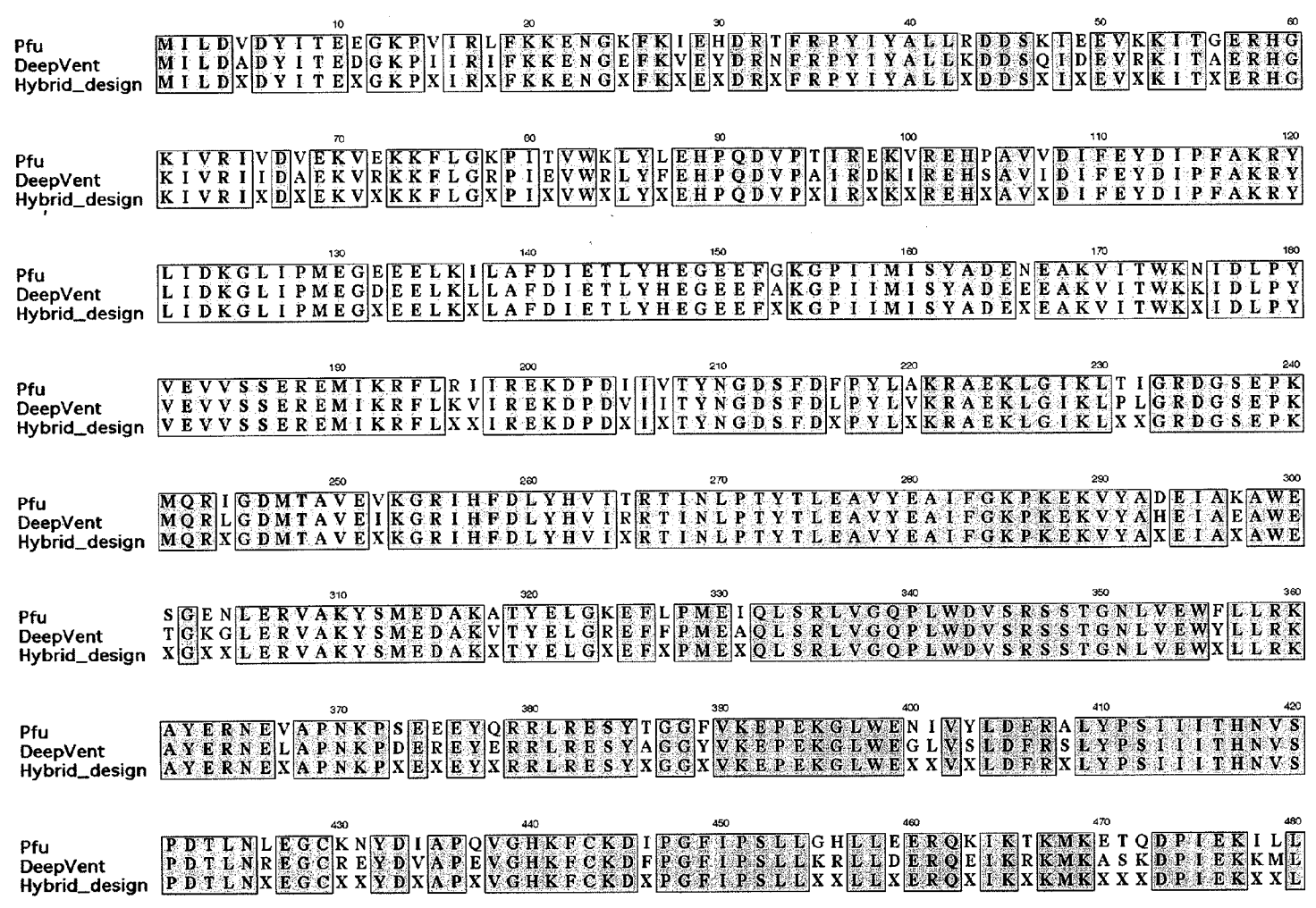

The protein sequences of Pfu polymerase and Deep Vent® polymerase were aligned. The alignment and a consensus hybrid protein sequence, in which X indicates the residues at which the parents differ, are shown in FIG. 1. The amino acid sequences of Pfu and Deep Vent® differ from one another at 115 locations. The sequences are 85% identical over the complete sequence. One 18-amino-acid-region is only 56% identical. Hybrid Deep Ventg®/Pfu proteins were produced by creating a collection of oligonucleotides that encodes a blend of sequences from the two parents and then assembling the oligonucleotides in a library of full-length polymerase proteins.

As stated, the alignment found 115 differences between the Pfu and Deep Vent® amino acid sequences. An *E. coli* codon usage table was then used to compare the various codons that can encode the amino acids and deduce an minimal encoding sequence. In many instances, a single nucleic acid degeneracy could encode both amino acids. For example, the parent proteins differ at amino acid position 15 where Pfu has a valine (Val) and Deep Vent® an isoleucine (Ile). It is possible to encode Val using GTT and Ile using ATT. The oligonucleotide synthesis machine was therefore programmed to produce product with half G and half A at nucleotide position 43 of the protein-coding DNA. Thus, a codon with a RTT where either a G or an A is introduced into the first nucleotide position of the codon will provide a pool of oligonucleotides, some of which have a GTT at that position; the others of which have an ATT at that position.

In the alignment of Pfu and Deep Vent®, 98 of the 115 differences could be simply incorporated into the library by introducing a single degeneracy at one nucleotide residue of the codon that encoded the different amino acids.

The remaining 17 differences required two nucleotides to be changed in order to encode the two parental sequences. These changes forced the possibility that two non-parental amino acid sequences would exist in the resulting library. An example of this is residue 72, at which Pfu has a glutamate (Glu) and the Deep Vent® has an arginine (Arg). Glu is encoded by GAR and Arg by CGN or AGR. The minimal encoding sequence (A/G)(A/G)G was selected to potentially encode the parent sequences at position 214 through 216 of the hybrid protein-coding region. This combination will also generate nucleotides encoding glycine (GGG) and lysine (AAG). This situation was determined to be tolerable even though glycine is not similar to either parental amino acid because such situations were rare relative to the size of the protein.

Incorporation of a potential stop codon at amino acid residue 758 (nucleic acid residues 2272 and 2273) was also deemed to be tolerable. This stop codon made ¼ of the library useless. Amino acid residue 566 (nucleotides 1696 through 1698) was made a lysine by mistake; it should have contained a nucleotide degeneracy that encoded lysine or aspartic acid.

For each strand of the minimal encoding sequence, a set of degenerate oligonucleotides of approximately 100 bases in length, and separated by gaps of 40 bases, was synthesized. The oligonucleotide sequences on the two strands were arranged so that the oligonucleotides from the first strand spanned the gaps on the second strand and overlapped the oligonucleotides of the second strand by 30 bases (FIG. 2). This oligonucleotide set was used in assembly PCR as follows. Overlapping oligonucleotides were paired, annealed to each other, and extended using a thermostable high fidelity polymerase. High concentrations of oligonucleotide and a minimal number of thermal cycles (no more than 5) were used. The products of the first cycle were double-stranded fragments of approximately 170 base pairs in length. These fragments were band-purified from a gel and used for the next cycle of pairing and primer extension to generate a new double-stranded fragment of about 310 base pairs in length. This cycle was repeated until the entire sequence was obtained as a collection of fragments of about 500 bases in length. At this point, particular fragments were selected and sequenced to assess the integrity of the procedure. It was found that the oligonucleotides purchased were of low quality, resulting in excessive unintended mutations. A number of segments containing no unintended mutations were chosen and used to assemble full-length genes using restriction sites that had been incorporated at the ends of each fragment and conventional molecular biology techniques. Four full-length clones were assembled and the encoded proteins were expressed in pET11 (Novogene, Madison, Wis.). Expression by all four clones was confirmed by SDS-PAGE. These clones were names Hyb1 to Hyb4.

A second collection of libraries was constructed on a custom basis by Blue Heron Biotechnology (Bothell, Wash.) using "Genemaker" technology. The complete coding sequence was delivered as four fragment libraries that could be assembled into a full-length hybrid genes. Two full-length assembled clones were obtained and sequenced to verify validity of the library. These clones were named Phy1 and Phy2. Clones from this library contained only proper hybrid sequences including the degeneracies at position 566 (lysine/aspartic acid) and 758 (tyrosine/tryptophan) discussed earlier. The full-length sequences were cloned into expression vectors and protein of the expected size were produced.

Hybrid polymerase protein was expressed and purified from each of the six clones from the two libraries. Purification was performed as follows.

Purification of Hybrid Polymerases

This section describes methodology for isolating a hybrid polymerase. Following induction of expression in *E. coli*, the cells were centrifuged and the pellets stored at −20° C. to −80° C. One milliliter of Buffer A (Buffer: 50 mM Tris (8.0); 50 mM Dextrose; 1 mM EDTA) was added for every 100 ml of starting culture and the cells were lysed with 4 mg/ml of powdered lysozyme at 72° C. $MgCl_2$ and $CaCl_2$ were added to a concentration of 2 mM, followed by the addition of 1 unit/ml of DNase I. The sample was shaken slowly for 10 min at room temperature. One ml of Buffer B (10 mM Tris (8.0); 50 mM KCl; 1 mM EDTA; 0.5% Tween 20; 0.5% NP40) was added per 100 ml starting culture and the sample then shaken slowly at room temperature for 15 min. The sample was transferred to a centrifuge tube and incubated at 72° C. for 1 hour followed by centrifugation at 4000×g at 4° C. for 15 min. The supernatant was collected and 0.476 gm/ml of $(NH_4)_2SO_4$ was added and the sample was mixed slowly at 4° C. for 1 hour and then centrifuged at 15,000×g at 4° C. for 15 mmin.

The pellet was resuspended in, and dialyzed against HiTrap Q 'A' Buffer (20 mM Tris (7.9); 50 mM NaCl; 5 mM β-mercaptoethanol). The suspension was then loaded onto a ÄKTAprime HiTrap Q chromatography column (Amersham Biosciences) equilibrated and run using method #2 per the manufacturers instructions using HiTrap Q buffers 'A' and 'B' ('A' buffer with 1 M NaCl). Fractions containing the polymerase were combined and dialyzed against P-11 Loading Buffer (20 mM Tris (7.9); 50 mM NaCl). The sample was bound to a liquid chromatography column of P-11 resin (Amersham Biosciences), washed with P-11 Buffer 'B' (20 mM Tris (7.9); 150 mM NaCl), then eluted using P-11 Elution Buffer (20 mM Tris (7.9); 400 mM NaCl). The eluted fractions were dialyzed against HiTrap SP 'A' buffer (20 mM Tris (6.8); 50 mM NaCl; 5 mM β-mercaptoethanol) then injected onto a ÄKTAprime HiTrap SP chromatography column equilibrated and run using method #2 per the manufacturers instructions using HiTrap SP 'A' and 'B' Buffer ('A' buffer with 1 M NaCl). Fractions containing PhS1 were concentrated using a YM-30 Centricon protein concentrator (Millipore). The sample was then dialyzed against buffer containing 50 mM Tris (pH 8.2); 0.1 mM EDTA; 1 mM DTT; 0.1% NP40; 0.1% Tween 20. The final volume was then measured and 1.47×85% glycerol, and 0.015×10% NP-40 and 10% Tween 20 added. The sample was stored at −20° C.

Of the six hybrid polymerase proteins generated from the two libraries, all had DNA polymerase activity.

Sso7d fusion polymerases (see, e.g., WO0192501) were prepared using some of the hybrid polymerase proteins and compared to the parental Pfu polymerase with and without Sso7d (designated as "Pfu" and "PfS", respectively) in exonuclease assays and extension assays. Sso7d fusions of Hyb clones are designated HyS; Sso7d fusions of the Phy clones are designated PhS. The most thoroughly studied hybrid protein was PhS1.

To measure exonuclease activity, a 45 base long primer with the following sequence was synthesized: 5'-FAM-TTTTTTGAGGTGTGTCCTACACAGCG-GAGTGTAGGAC ACACCTCT* 3' (SEQ ID NO:49), wherein T*=is an amino-link dT with the quencher, DAB (dabcyl) attached. The sequence forms a 16 base pair stem loop structure with a T:T* mismatch at the quencher-labeled base. The 5' unbase-paired poly T sequence keeps FAM (6 carboxy-fluorescein) in close proximity to the quenching dye so the FAM, if excited, it will not fluoresce.

Figure 3:
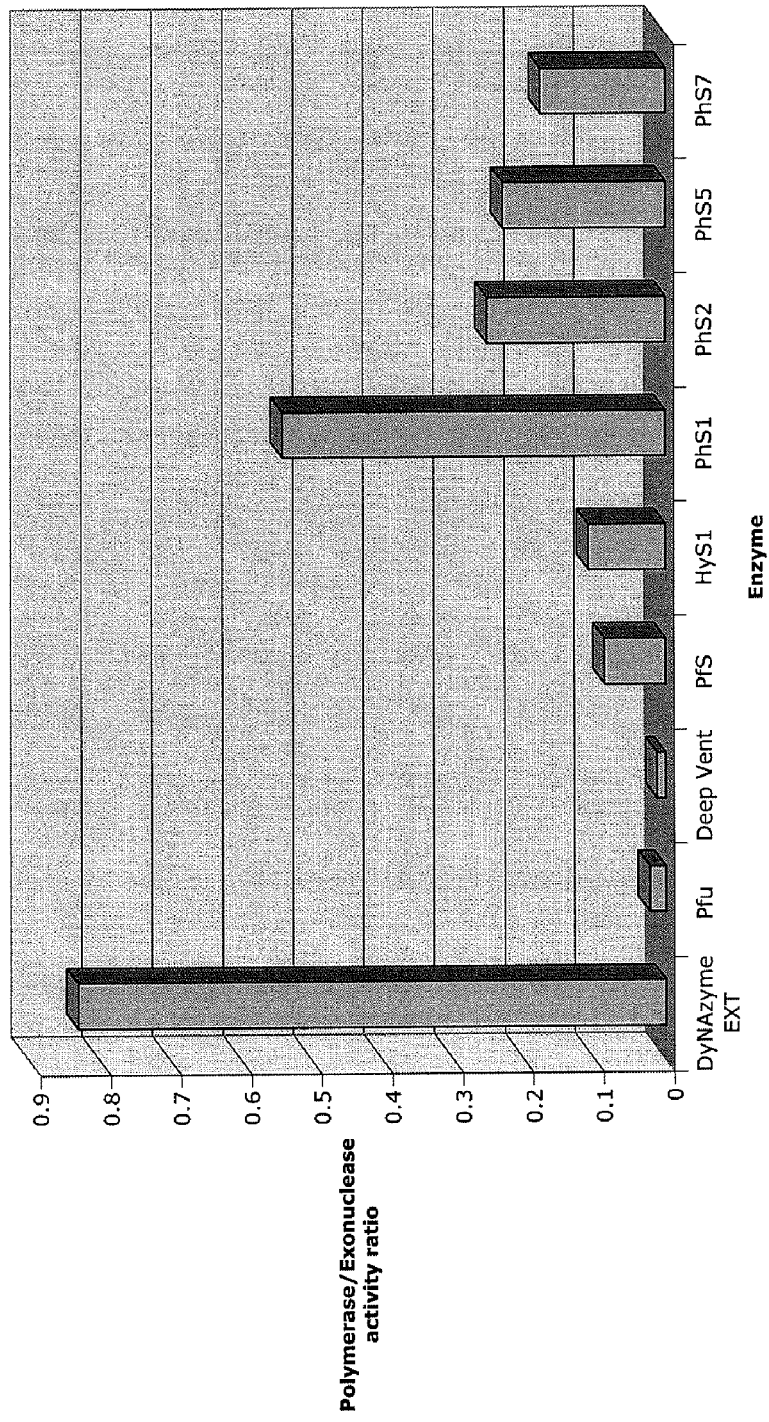
FIG. 3 shows a comparison of the polymerase to 3' exonuclease ratios for several commercially available enzymes, including the parental proteins, and isolates from the hybrid library.

The oligonucleotide was combined with buffer and the enzyme and incubated in a real time detection instrument, the DNA Engine Opticon System (MJ Research, Inc.). This instrument excites the FAM and detects any fluorescence if present. In the absence of 3' to 5' exonuclease activity, there is only background fluorescence because FAM is quenched by DAB. However if the enzyme does have 3' to 5' exonuclease activity, the T:T* mismatch is recognized and the 3'-T* is removed. The DAB is released and will no longer quench the FAM fluorescence. The Opticon System will detect the increase in fluorescence with increasing time (readings were taken every 10 sec at 65° C.). The rate of fluorescence increase directly reflects the amount of 3' to 5' exonuclease activity. An increase in fluorescence greater than control levels shows that the enzyme has 3' to 5' exonuclease activity. The results (FIG. 3) of this analysis are discussed below.

Figure 4:
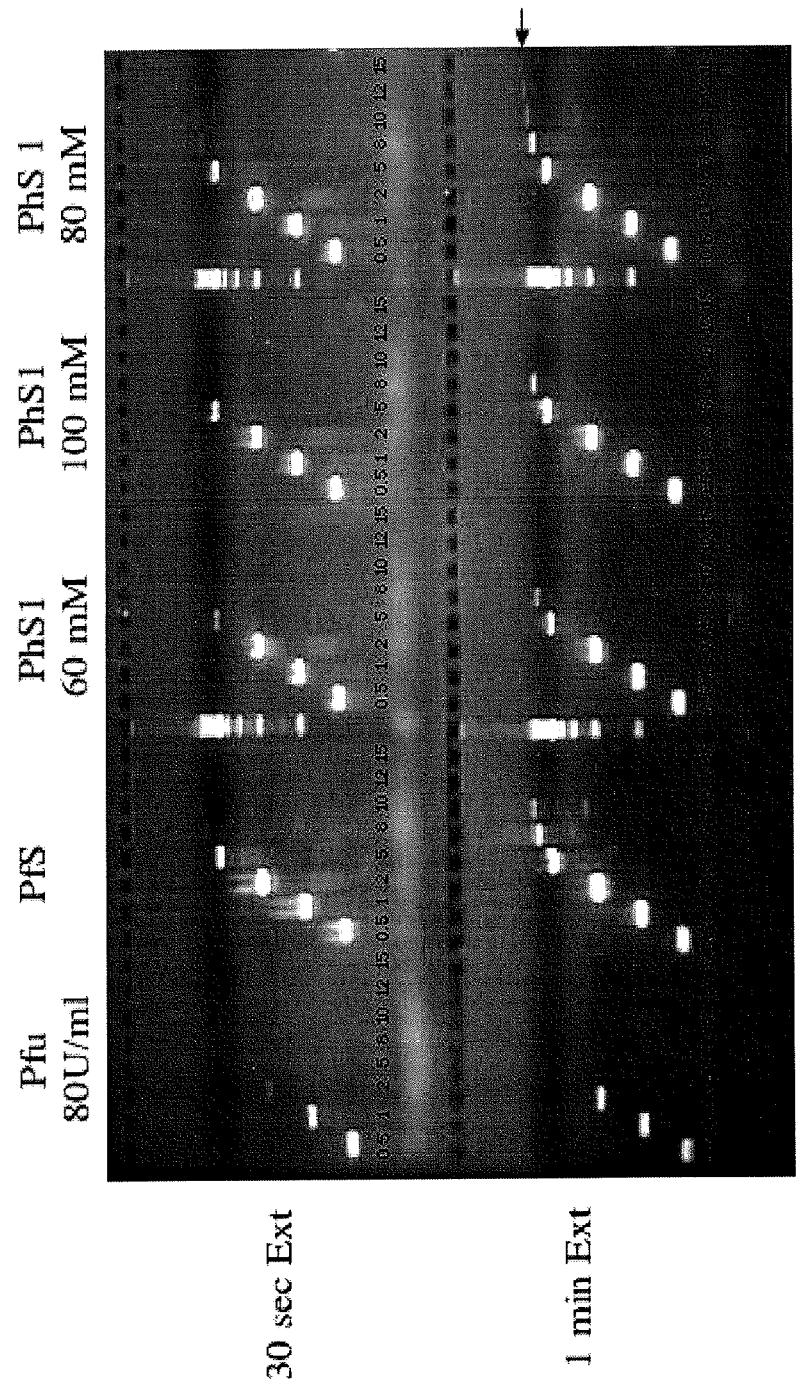
FIG. 4 shows the results of a comparison of hybrid and parent polymerases. The enzymes were tested for the ability to amplify bacteriophage lambda DNA amplicons of a range of sizes, given a 30 sec or 1 min extension time. The sizes of the amplicons, in kilobases, are listed across the bottom of the lanes. Twenty units of enzyme per ml were used unless otherwise specified.

FIG. 4 shows results of a comparison of a hybrid and a parent polymerase in extension assays. Even with excess enzyme (80 U/ml), Pfu could not amplify any amplicon longer than 2 kb. An Sso7d fusion to Pfu polymerase (PfS) amplified a 10 kb fragment given a 1 min extension time. PhS1 amplified a 15 kb fragment (arrow) in 80 mM KCl with a 1 minute extension time. Further, PhS1 was also able to perform long PCR under a variety of salt conditions.

Characterization of Additional Hybrid Polymerases

Five additional hybrid clones were isolated from the second library directly as Sso7d fusions and were designated PhS3 to PhS7. The polymerases were tested for polymerase and exonuclease activity. Table 1 summarizes characteristics of the various hybrid proteins analyzed in this example. PhS2 has two mutations at sites other than a target site. PhS3 is truncated due to an early stop codon. PhS4 has one deletion and one mutation. The "Hyb" and "HyS" polymerases also comprise mutations at positions other than the target sites, probably due to faulty oligonucleotide synthesis.

TABLE 1

| Pol | Activity | Full-length | KCL Opt | Temp. Stab. | Processivity | Number Pfu parent residues | Number D. vent parent residues | Relative specific activity |
|---|---|---|---|---|---|---|---|---|
| PhS1 | Yes | Yes | 80-100 mM | 3 hr, 97.5 | 26-30 | 55 | 60 | 1.5 |
| PhS2 | Yes | Yes | 160-180 mM | 3 hr+, 97.5 | 24-28 | 64 | 51 | 4 |
| PhS3 | No | No | N/A | N/A | N/A | N/A | N/A | n.d |
| PhS4 | No | No; minus one Pfu/DV amino acid | N/A | N/A | N/A | 56 | 58 | nd. |
| PhS5 | Yes | Yes | 40-80 mM | 3 hr, 97.5 | nd | 52 | 63 | 1 |
| Ph6 | No | No | N/A | N/A | N/A | 55 | 60 | n.d. |
| Ph7 | Yes | Yes | 40-80 mM | 3 hr, 97.5 | nd | 54 | 61 | 2 |
| Hyb1 | Yes | Yes | nd | 10 min* | 2-4 nt | 59 | 46 | n.d. |
| HyS1 | Yes | Yes | 90-100 mM | 8-14 min* | 11 nt | 59 | 46 | 2 |
| Hyb2** | Yes | No | nd | n.d. | n.d. | 50 | 53 | n.d. |
| Hyb3** | Yes | No | nd | n.d. | n.d. | 51 | 47 | n.d. |
| HyS4 | Yes | Yes | 80-90 mM | <1 min* | n.d. | 51 | 50 | n.d. |

All polymerases designated "PhS" are Sso7d fusions.
"HyS1" is Hyb1 with Sso7d at the C-terminus.
"HyS4" has Sso7d at the C-terminus.

The exonuclease activity of various hybrid polymerases was also evaluated as described above. The polymerase- to –3'-exonuclease ratios for several commercially available enzymes, including the parental proteins and isolates from the hybrid library, were compared. DyNAzyme EXT, an enzyme used in long accurate PCR, is a blend of a Family B polymerase with 3' to 5' exonuclease activity, and a Family A polymerase that lacks any proofreading activity. Too much exonuclease activity is detrimental because it digests primers instead of extending them. Pfu and Deep Vent® are the parental Family B polymerases which both have high exonuclease activity. PfS (a Pfu-Sso7d fusion enzyme) has increased polymerase activity. HyS1, PhS1, PhS2, PhS5, and PhS7 are isolates from the hybrid libraries. Surprisingly, the results (FIG. 3) show that the hybrid proteins vary greatly in their polymerase to exonuclease activities, both relative to the parent proteins and each other. PhS1 has a polymerase to exonuclease activity ratio approaching that of the enzyme blend.

These results show that multiple polymerase hybrid isolates from two different libraries were active. Furthermore, the example shows that the method also allows for generating hybrids for different domains, i.e., polymerase activity domain vs. exonuclease activity domain.

Figure 5:
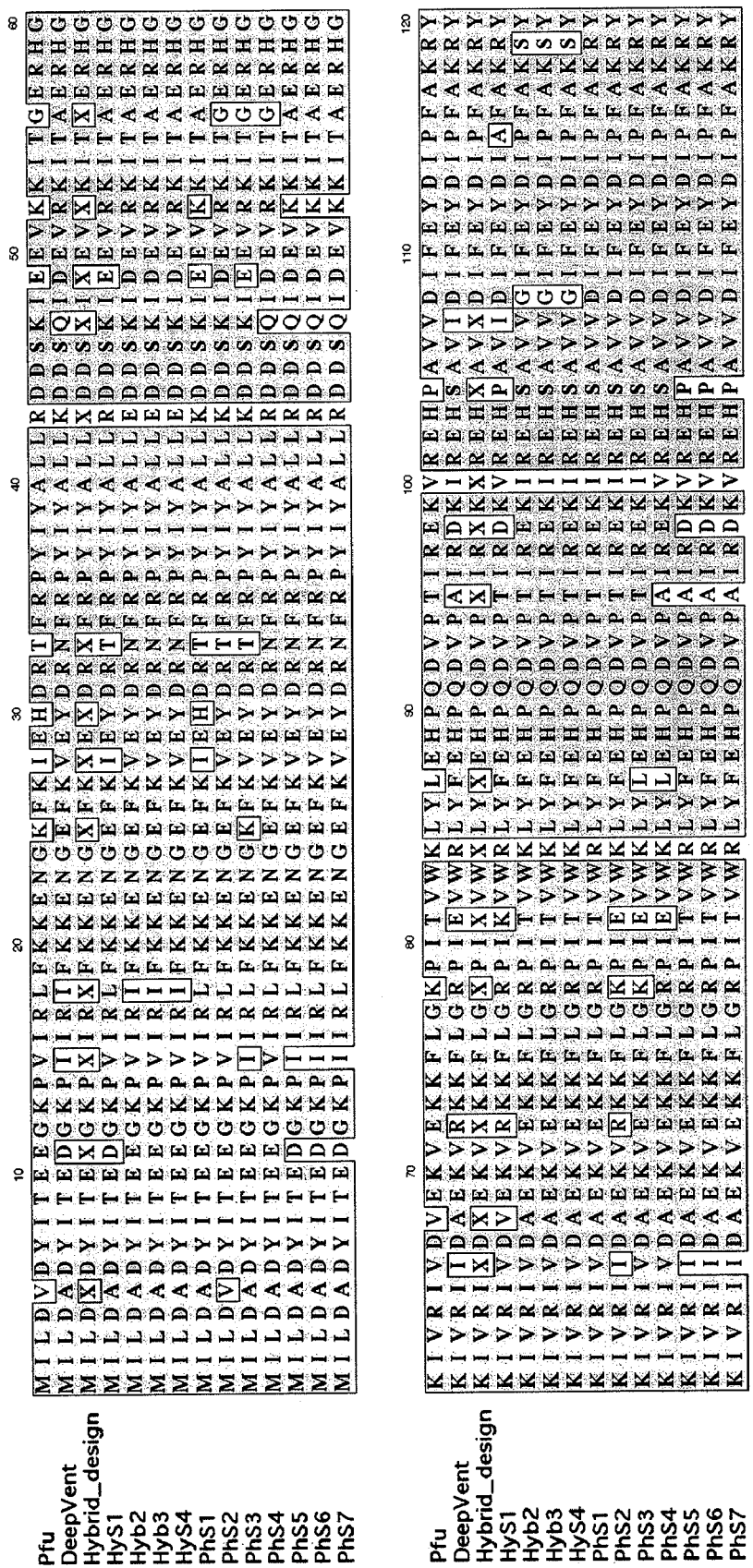
FIG. 5 shows an alignment of the parental Pfu (SEQ ID NO:24) and Deep Vent® (SEQ IID NO:25) sequences, and various hybrid polymerase sequences (Hybrid design, HyS1, Hyb2, Hyb3, HyS4, PhS1, PhS2, PhS3, PhS4, PhS5, PhS6, and PhS7; SEQ ID NOS:27, 28, 29, 30, 31, 32, 33, 34, 35, 36, 37, and 10, respectively).
Figure 5:
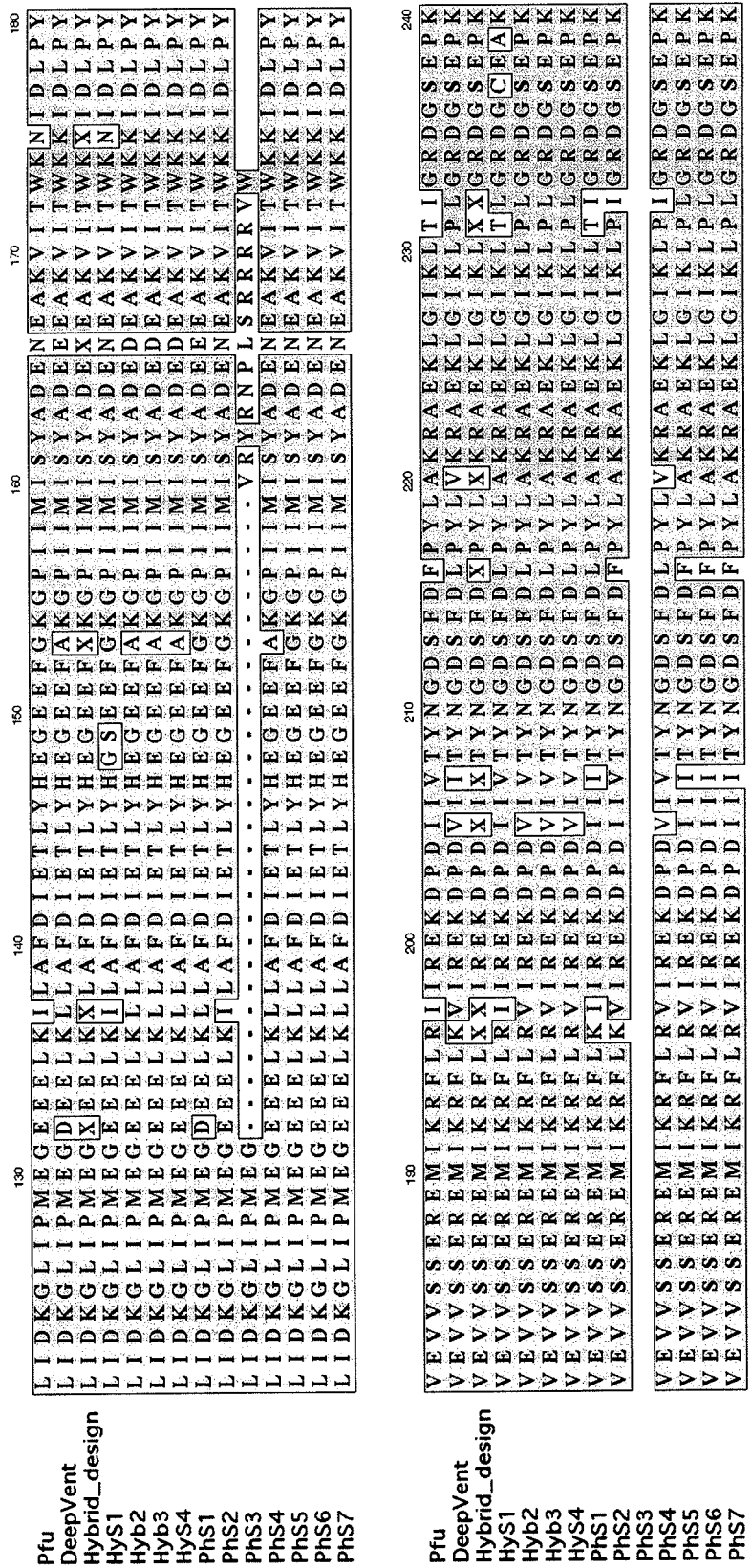
Figure 5:
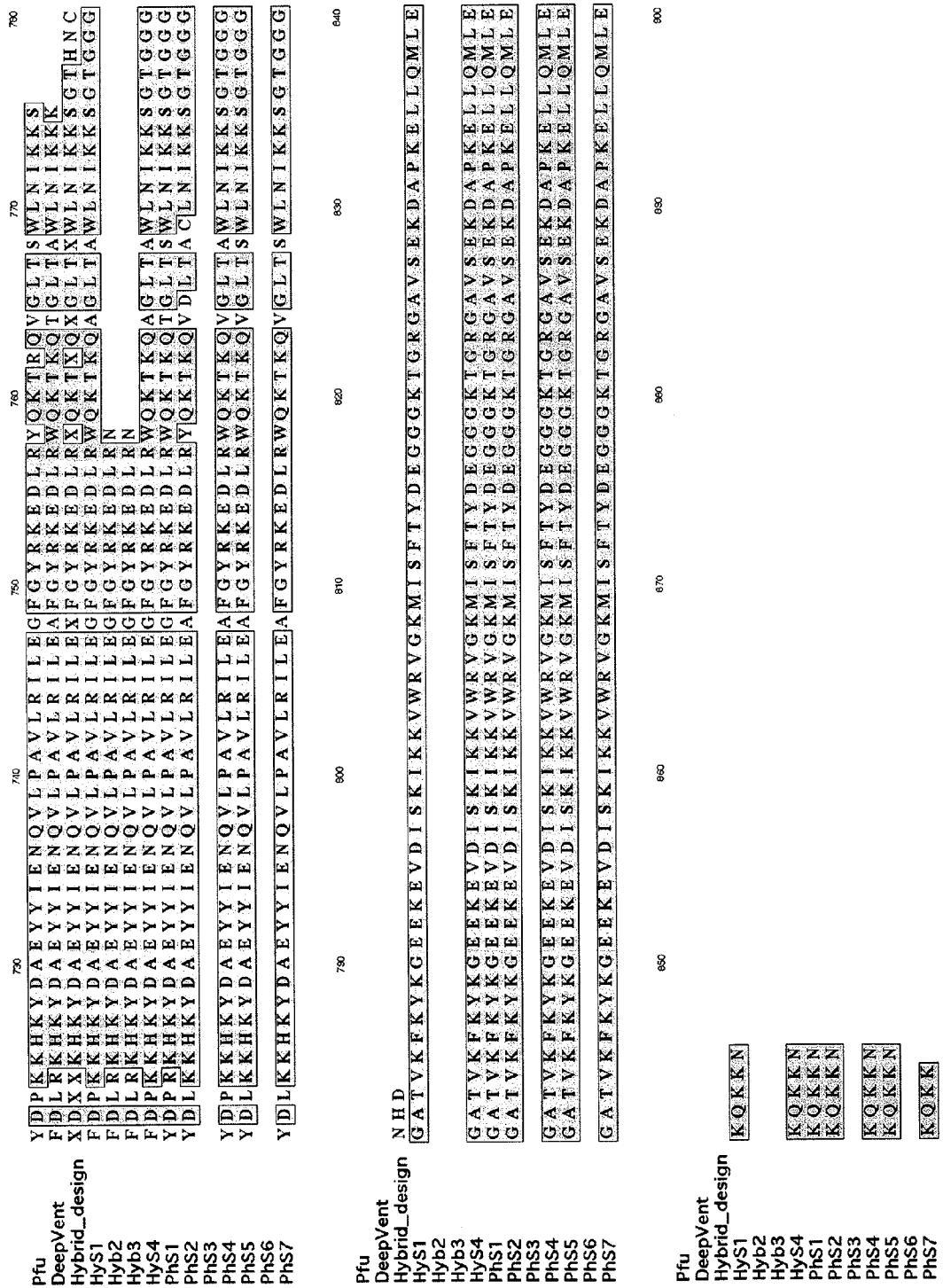
Figure 6:
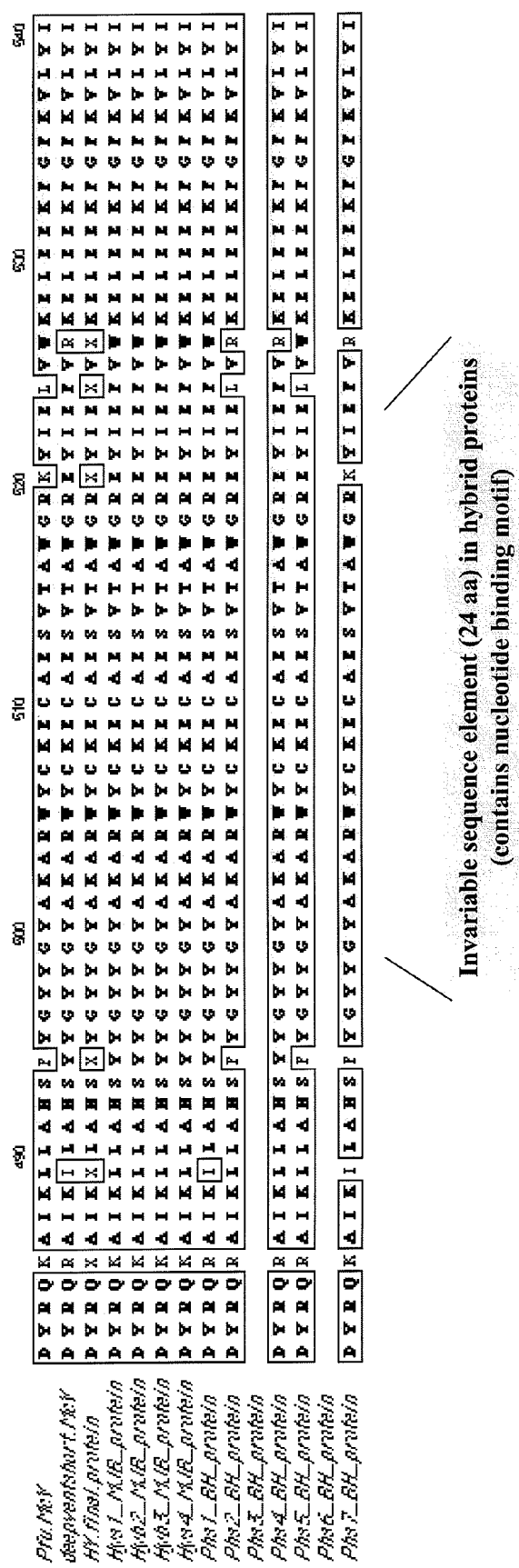
FIG. 6 shows a sequence element that is common to the parental and hybrid sequences Pfu (SEQ ID NO:38); Deep Vent (SEQ ID NO:39); Hybrid final protein (SEQ ID NO:40); HyS1, Hyb2, Hyb3, and HyS4 (SEQ ID NO:41); PhS1 (SEQ ID NO:42); PhS2 (SEQ ID NO:43); PhS4 (SEQ ID NO:44); PhS5 (SEQ ID NO:45); and PhS7 (SEQ ID NO:46).

A comparison of the sequences of the parent and various hybrid proteins is presented in FIG. 5. As can be seen, a signature sequence, i.e., an invariable sequence element, is present in all of the proteins. This element (FIG. 6) contains the nucleotide binding motif and is characteristic of Pfu/Deep Vent polymerases generated using the method described herein. The sites that differ between the parent polymerases are indicated.

Example 2

Substantially Identical Polynerase Gene Synthesis

The following is a preferred method of generating polymerase nucleic acids encoding polymerases substantially identical to a polymerase of the invention, e.g., SEQ ID NO:2 or SEQ ID NO:4. A set of conservative substitutions are chosen. A degenerate sequence is constructed, where the degenerate positions in the nucleotide encode, in their alternative forms, at least the two amino acids corresponding to the wild-type amino acid and the conservative substitution. For each strand of the degenerate sequence, a set of degenerate oligonucleotides of approximately 100 bases in length, and separated by gaps of 40 bases, is synthesized. The oligonucleotide sequences on the two strands are arranged so that the oligonucleotides from the first strand span the gaps on the second strand and overlap the oligonucleotides of the second strand by 30 bases. This oligonucleotide set is used in assembly PCR as follows. Overlapping oligonucleotides are paired, annealed to each other, and extended using a thermostable high fidelity polymerase. High concentrations of oligonucleotide and a minimal number of thermal cycles (no more than 5) are used whenever possible. The products of the first cycle are double-stranded fragments of length approximately 170 bases. These are band-purified from a gel and used for the next cycle of pairing and primer extension to generate new double-stranded fragments of length approximately 310 bases. This cycle is repeated until the entire sequence has been obtained in a single fragment. If at any point the quantity of the product becomes too low, the amount can be increased by PCR using short (15-30) base primers corresponding to the ends of particular desired fragments. Cloning of partial gene sequences, and/or cutting with restriction enzymes and ligating subfragments together, are additional techniques that may be used to improve the efficiency of the gene construction process. When the entire gene is synthesized, it is cloned into a vector suitable for protein expression. Because the sequence is degenerate, cloning will produce a library of related but different clones, which must be screened to eliminate those clones that do not produce a functional protein or which are not substantially identical to the target polymerase.

Table of Polymerase Sequences

SEQ ID NO:1 Phy1 nucleic acid sequence

ATGATCCTGGATGCTGACTACATCACTGAAGAAGGCAAACCGGTTATCCG

TCTGTTCAAAAAAGAGAACGGCGAATTTAAGATTGAGCATGATCGCACCT

TTCGTCCATACATTTACGCTCTGCTGAAAGATGATTCTAAGATTGAGGAA

-continued
```
GTTAAAAAAATCACTGCTGAGCGCCATGGCAAGATTGTTCGTATCGTTGA
TGCGGAAAAGGTAGAAAAGAAATTTCTGGGCAGACCAATCACCGTGTGGA
GACTGTATTTCGAACATCCACAAGATGTTCCGACTATTCGCGAGAAAATT
CGCGAACATTCTGCAGTTGTTGACATCTTCGAATACGATATTCCATTTGC
AAAGCGTTACCTCATCGACAAAGGCCTGATACCAATGGAGGGCGATGAAG
AACTCAAGCTCCTGGCGTTCGATATAGAAACCCTCTATCACGAAGGCGAA
GAGTTTGGTAAAGGCCCAATTATAATGATCAGCTATGCAGATGAAGAAGA
AGCAAAGGTGATTACTTGGAAAAAAATAGATCTCCCATACGTTGAGGTTG
TATCTTCCGAGCGCGAGATGATTAAGCGCTTTCTCAAAATTATCCGCGAG
AAGGATCCGGACATTATCATTACTTATAACGGCGACTCTTTTGACCTCCC
ATATCTGGCGAAACGCGCAGAAAAACTCGGTATTAAACTGACTATCGGCC
GTGATGGTTCCGAGCCGAAGATGCAGCGTATCGGCGATATGACCGCTGTA
GAAGTTAAGGGTCGTATCCATTTCGACCTGTATCATGTAATTCGTCGTAC
TATTAACCTCCCGACTTACACTCTCGAGGCTGTATATGAAGCAATTTTTG
GTAAGCCGAAGGAGAAGGTATACGCCGATGAGATTGCAAAGGCGTGGGAA
ACCGGTGAGGGCCTCGAGCGTGTTGCAAAATACTCCATGGAAGATGCAAA
GGCGACTTATGAACTCGGCAAAGAATTCTTCCCAATGGAAGCTCAGCTCT
CTCGCCTGGTTGGCCAACCACTGTGGGATGTTTCTCGTTCTTCCACCGGT
AACCTCGTAGAGTGGTTTCTCCTGCGCAAAGCGTACGAACGCAACGAACT
GGCTCCGAACAAGCCAGATGAACGTGAGTATGAACGCCGTCTCCGCGAGT
CTTACGCTGGTGGCTTTGTTAAAGAGCCAGAAAAGGGCCTCTGGGAAAAC
ATCGTGTCCCTCGATTTTCGCGCTCTGTATCCGTCTATTATCATTACCCA
CAACGTGTCTCCGGATACTCTCAACCGCGAGGGCTGCAGAAACTATGATG
TTGCTCCGGAAGTAGGCCACAAGTTCTGCAAGGACTTCCCGGGCTTTATT
CCGTCTCTCCTGAAACGTCTGCTCGATGAACGCCAAAAGATTAAGACTAA
AATGAAGGCGTCCCAGGATCCGATTGAAAAAATAATGCTCGACTATCGCC
AAAGAGCGATTAAAATCCTCGCAAACTCTTATTACGGCTATTATGGCTAT
GCAAAAGCACGCTGGTACTGTAAGGAGTGTGCTGAGTCCGTTACTGCTTG
GGGTCGCGAATACATCGAGTTCGTGTGGAAGGAGCTCGAAGAAAGTTTG
GCTTTAAAGTTCTCTACATTGACACTGATGGTCTCTATGCGACTATTCCG
GGTGGTAAGTCTGAGGAAATTAAGAAAAAGGCTCTAGAATTTGTGGATTA
CATTAACGCGAAGCTCCCGGGTCTCCTGGAGCTCGAATATGAAGGCTTTT
ATAAACGCGGCTTCTTCGTTACCAAGAAGAAATATGCGCTGATTGATGAA
GAAGGCAAAATTATTACTCGTGGTCTCGAGATTGTGCGCCGTGATTGGAG
CGAAATTGCGAAAGAAACTCAAGCTAGAGTTCTCGAGGCTATTCTCAAAC
ACGGCAACGTTGAAGAAGCTGTGAGAATTGTAAAAGAAGTAACCCAAAAG
CTCTCTAAATATGAAATTCCGCCAGAGAAGCTCGCGATTTATGAGCAGAT
TACTCGCCCGCTGCATGAGTATAAGGCGATTGGTCCGCACGTGGCTGTTG
CAAAGAGACTGGCTGCTAAAGGCGTGAAAATTAAACCGGGTATGGTAATT
GGCTACATTGTACTCCGCGGCGATGGTCCGATTAGCAACCGTGCAATTCT
AGCTGAGGAATACGATCCGAGAAAGCACAAGTATGACGCAGAATATTACA
TTGAGAACCAGGTGCTCCCGGCGGTACTCCGTATTCTGGAGGGTTTTGGC
TACCGTAAGGAAGACCTCCGCTGGCAAAAGACTAAACAGACTGGCCTCAC
TTCTTGGCTCAACATTAAAAAATCC
```

SEQ ID NO:2 Phy1 polypeptide sequence
```
MILDADYITEEGKPVIRLFKKENGEFKIEHDRTFRPYIYALLKDDSKIEEVKKITAERH
GKIVRIVDAEKVEKKFLGRPITVWRLYFEHPQDVPTIREKIREHSAVVDIFEYDIPFAK
RYLIDKGLIPMEGDEELKLLAFDIETLYHEGEEFGKGPIIMISYADEEEAKVITWKKID
LPYVEVVSSEREMIKRFLKIIREKDPDIIITYNGDSFDLPYLAKRAEKLGIKLTIGRDGS
EPKMQRIGDMTAVEVKGRIHFDLYHVIRRTINLPTYTLEAVYEAIFGKPKEKVYADEI
AKAWETGEGLERVAKYSMEDAKATYELGKEFFPMEAQLSRLVGQPLWDVSRSSTG
NLVEWFLLRKAYERNELAPNKPDEREYERRLRESYAGGFVKEPEKGLWENIVSLDFR
ALYPSIIITHNVSPDTLNREGCRNYDVAPEVGHKFCKDFPGFIPSLLKRLLDERQKIKT
KMKASQDPIEKIMLDYRQRAIKILANSYYGYYGYAKARWYCKECAESVTAWGREYI
EFVWKELEEKFGFKVLYIDTDGLYATIPGGKSEEIKKKALEFVDYINAKLPGLLELEY
EGFYKRGFFVTKKKYALIDEEGKIITRGLEIVRRDWSEIAKETQARVLEAILKHGNVE
EAVRIVKEVTQKLSKYEIPPEKLAIYEQITRPLHEYKAIGPHVAVAKRLAAKGVKIKP
GMVIGYIVLRGDGPISNRAILAEEYDPRKHKYDAEYYIENQVLPAVLRILEGFGYRKE
DLRWQKTKQTGLTSWLNIKKS
```

SEQ ID NO:3 Nucleic acid sequence encoding PhS1, a fusion protein comprising Phy1 and SSo7d, with the linker and the Sso7d coding region in lower case, and the linker region in bold.

ATGATCCTGGATGCTGACTACATCACTGAAGAAGGCAAACCGGTTATCCGTCTGT
TCAAAAAAGAGAACGGCGAATTTAAGATTGAGCATGATCGCACCTTTCGTCCAT
ACATTTACGCTCTGCTGAAAGATGATTCTAAGATTGAGGAAGTTAAAAAAATCAC
TGCTGAGCGCCATGGCAAGATTGTTCGTATCGTTGATGCGGAAAAGGTAGAAAA
GAAATTTCTGGGCAGACCAATCACCGTGTGGAGACTGTATTTCGAACATCCACAA
GATGTTCCGACTATTCGCGAGAAAATTCGCGAACATTCTGCAGTTGTTGACATCT
TCGAATACGATATTCCATTTGCAAAGCGTTACCTCATCGACAAAGGCCTGATACC
AATGGAGGGCGATGAAGAACTCAAGCTCCTGGCGTTCGATATAGAAACCCTCTA
TCACGAAGGCGAAGAGTTTGGTAAAGGCCCAATTATAATGATCAGCTATGCAGA
TGAAGAAGAAGCAAAGGTGATTACTTGGAAAAAAATAGATCTCCCATACGTTGA
GGTTGTATCTTCCGAGCGCGAGATGATTAAGCGCTTTCTCAAAATTATCCGCGAG
AAGGATCCGGACATTATCATTACTTATAACGGCGACTCTTTTGACCTCCCATATCT
GGCGAAACGCGCAGAAAAACTCGGTATTAAACTGACTATCGGCCGTGATGGTTC
CGAGCCGAAGATGCAGCGTATCGGCGATATGACCGCTGTAGAAGTTAAGGGTCG
TATCCATTTCGACCTGTATCATGTAATTCGTCGTACTATTAACCTCCCGACTTACA
CTCTCGAGGCTGTATATGAAGCAATTTTTGGTAAGCCGAAGGAGAAGGTATACG
CCGATGAGATTGCAAAGGCGTGGGAAACCGGTGAGGGCCTCGAGCGTGTTGCAA
AATACTCCATGGAAGATGCAAAGGCGACTTATGAACTCGGCAAAGAATTCTTCC
CAATGGAAGCTCAGCTCTCTCGCCTGGTTGGCCAACCACTGTGGGATGTTTCTCG
TTCTTCCACCGGTAACCTCGTAGAGTGGTTTCTCCTGCGCAAAGCGTACGAACGC
AACGAACTGGCTCCGAACAAGCCAGATGAACGTGAGTATGAACGCCGTCTCCGC
GAGTCTTACGCTGGTGGCTTTGTTAAAGAGCCAGAAAAGGGCCTCTGGGAAAAC
ATCGTGTCCCTCGATTTTCGCGCTCTGTATCCGTCTATTATCATTACCCACAACGT
GTCTCCGGATACTCTCAACCGCGAGGGCTGCAGAAACTATGATGTTGCTCCGGAA
GTAGGCCACAAGTTCTGCAAGGACTTCCCGGGCTTTATTCCGTCTCTCCTGAAAC
GTCTGCTCGATGAACGCCAAAAGATTAAGACTAAAATGAAGGCGTCCCAGGATC
CGATTGAAAAAATAATGCTCGACTATCGCCAAAGAGCGATTAAAATCCTCGCAA
ACTCTTATTACGGCTATTATGGCTATGCAAAAGCACGCTGGTACTGTAAGGAGTG
TGCTGAGTCCGTTACTGCTTGGGGTCGCGAATACATCGAGTTCGTGTGGAAGGAG
CTCGAAGAAAGTTTGGCTTTAAAGTTCTCTACATTGACACTGATGGTCTCTATG
CGACTATTCCGGGTGGTAAGTCTGAGGAAATTAAGAAAAAGGCTCTAGAATTTG
TGGATTACATTAACGCGAAGCTCCCGGGTCTCCTGGAGCTCGAATATGAAGGCTT
TTATAAACGCGGCTTCTTCGTTACCAAGAAGAAATATGCGCTGATTGATGAAGAA
GGCAAAATTATTACTCGTGGTCTCGAGATTGTGCGCCGTGATTGGAGCGAAATTG
CGAAAGAAACTCAAGCTAGAGTTCTCGAGGCTATTCTCAAACACGGCAACGTTG
AAGAAGCTGTGAGAATTGTAAAAGAAGTAACCCAAAAGCTCTCTAAATATGAAA
TTCCGCCAGAGAAGCTCGCGATTTATGAGCAGATTACTCGCCCGCTGCATGAGTA

```
-continued
TAAGGCGATTGGTCCGCACGTGGCTGTTGCAAAGAGACTGGCTGCTAAAGGCGT

GAAAATTAAACCGGGTATGGTAATTGGCTACATTGTACTCCGCGGCGATGGTCCG

ATTAGCAACCGTGCAATTCTAGCTGAGGAATACGATCCGAGAAAGCACAAGTAT

GACGCAGAATATTACATTGAGAACCAGGTGCTCCCGGCGGTACTCCGTATTCTGG

AGGGTTTTGGCTACCGTAAGGAAGACCTCCGCTGGCAAAAGACTAAACAGACTG

GCCTCACTTCTTGGCTCAACATTAAAAAATCCggtaccggcggtggcggtgcaaccgtaaagttcaag tacaaaggcgaagaaaagaggtagacatctccaagatcaagaaagtatggcgtgtgggcaagatgat ctccttcacctacgacgagggcggtggcaagaccggccgtggtgcggtaagcgaaaaggacgcgccga aggagctgctgcagatgctggagaagcagaaaaagtga
```

SEQ ID NO:4 The amino acid sequence of PhS1 (a PHY-SSo7d fusion protein), with the linker and the Sso7d coding region in lower case, and the linker region in bold.

```
MILDADYITEEGKPVIRLFKKENGEFKIEHDRTFRPYIYALLKDDSKIEEVKKITAERH
GKIVRIVDAEKVEKKFLGRPITVWRLYFEHPQDVPTIREKIREHSAVVDIFEYDIPFAK
RYLIDKGLIPMEGDEELKLLAFDIETLYHEGEEFGKGPIIMISYADEEEAKVITWKKID
LPYVEVVSSEREMIKRFLKIIREKDPDIIITYNGDSFDLPYLAKRAEKLGIKLTIGRDGS
EPKMQRIGDMTAVEVKGRIHFDLYHVIRRTINLPTYTLEAVYEAIFGKPKEKVYADEI
AKAWETGEGLERVAKYSMEDAKATYELGKEFFPMEAQLSRLVGQPLWDVSRSSTG
NLVEWFLLRKAYERNELAPNKPDEREYERRLRESYAGGFVKEPEKGLWENIVSLDFR
ALYPSIIITHNVSPDTLNREGCRNYDVAPEVGHKFCKDFPGFIPSLLKRLLDERQKIKT
KMKASQDPIEKIMLDYRQRAIKILANSYYGYYGYAKARWYCKECAESVTAWGREYI
EFVWKELEEKFGFKVLYIDTDGLYATIPGGKSEEIKKKALEFVDYINAKLPGLLELEY
EGFYKRGFFVTKKKYALIDEEGKIITRGLEIVRRDWSEIAKETQARVLEAILKHGNVE
EAVRIVKEVTQKLSKYEIPPEKLAIYEQITRPLHEYKAIGPHVAVAKRLAAKGVKIKP
GMVIGYIVLRGDGPISNRAILAEEYDPRKHKYDAEYYIENQVLPAVLRILEGFGYRKE
DLRWQKTKQTGLTSWLNIKKSgtgggatvkfkykgeekevdiskikkvwrvgkmisftyde
gggktgrgavsekdapkellqmlekqkk*
```

SEQ ID NO:5 PhS2 nucleic acid sequence

```
ATGATCCTGGATGTTGACTACATCACTGAAGAAGGCAAACCGGTTATCCG
TCTGTTCAAAAAAGAGAACGGCGAATTTAAGGTTGAGTATGATCGCACCT
TTCGTCCATACATTTACGCTCTGCTGAAAGATGATTCTAAGATTGATGAA
GTTAGAAAAATCACTGGTGAGCGCCATGGCAAGATTGTTCGTATCATTGA
TGCGGAAAAGGTACGTAAGAAATTTCTGGGCAAACCAATCGAGGTGTGGA
AACTGTATTTCGAACATCCACAAGATGTTCCGACTATCGCGAGAAAATT
CGCGAACATTCTGCAGTTGTTGACATCTTCGAATACGATATTCCATTTGC
AAAGCGTTACCTCATCGACAAAGGCCTGATACCAATGGAGGGCGAGGAAG
AACTCAAGATCCTGGCGTTCGATATAGAAACCCTCTATCACGAAGGCGAA
GAGTTTGGTAAAGGCCCAATTATAATGATCAGCTATGCAGATGAAAACGA
AGCAAAGGTGATTACTTGGAAAAAAATAGATCTCCCATACGTTGAGGTTG
TATCTTCCGAGCGCGAGATGATTAAGCGCTTTCTCAAAGTTATCCGCGAG
AAGGATCCGGACATTATCGTTACTTATAACGGCGACTCTTTTGACTTCCC
ATATCTGGCGAAACGCGCAGAAAAACTCGGTATTAAACTGCCTATCGGCC
GTGATGGTTCCGAGCCGAAGATGCAGCGTATCGGCGATATGACCGCTGTA
GAAGTTAAGGGTCGTATCCATTTCGACCTGTATCATGTAATTCGTCGTAC
TATTAACCTCCCGACTTACACTCTCGAGGCTGTATATGAAGCAATTTTTG
GTAAGCCGAAGGAGAAGGTATACGCCCATGAGATTGCAGAGGCGTGGGAA
TCCGGTGAGGGCCTCGAGCGTGTTGCAAAATACTCCATGGAAGATGCAAA
```

-continued

```
GGCGACTTATGAACTCGGCAAAGAATTCTTCCCAATGGAAATCCAGCTCT
CTCGCCTGGTTGGCCAACCACTGTGGGATGTTTCTCGTTCTTCCACCGGT
AACCTCGTAGAGTGGTTTCTCCTGCGCAAAGCGTACGAACGCAACGAACT
GGCTCCGAACAAGCCATCTGAACGTGAGTATGAACGCCGTCTCCGCGAGT
CTTACACTGGTGGCTATGTTAAAGAGCCAGAAAAGGGCCTCTGGGAAAAC
ATCGTGTACCTCGATTTTCGCTCTCTGTATCCGTCTATTATCATTACCCA
CAACGTGTCTCCGGATACTCTCAACCTCGAGGGCTGCAAAGAGTATGATG
TTGCTCCGGAAGTAGGCCACAAGTTCTGCAAGGACATCCCGGGCTTTATT
CCGTCTCTCCTGGGCCATCTGCTCGAGGAACGCCAAAAGATTAAGCGTAA
AATGAAGGCGTCCAAGGATCCGATTGAAAAAATACTGCTCGACTATCGCC
AAAGAGCGATTAAACTCCTCGCAAACTCTTTTTACGGCTATTATGGCTAT
GCAAAAGCACGCTGGTACTGTAAGGAGTGTGCTGAGTCCGTTACTGCTTG
GGGTCGCGAATACATCGAGCTCGTGCGGAAGGAGCTCGAAGAAAAGTTTG
```

-continued

```
ACGGCAACGTTGAAGAAGCTGTGAGAATTGTAAAAGAAGTAACCCAAAAG
CTCGCTAAATATGAAATTCCACCAGAGAAGCTCGCGATTTATGAGCAGAT
TACTCCCCCCCTGCATGAGTATAAGGCGATTGGTCCCCACGTGGCTGTTG
CAAAGAGACTGGCTGCTAGAGGCGTGAAAATTAAACCGGGTATGGTAATA
GGCTACATTGTACTCCGCGGCGATGGTCCGATTAGCAACCGTGCAATTCT
AGCTGAGGAATACGATCTGAAAAAGCACAAGTATGACGCAGAATATTACA
TTGAGAACCAGGTGCTCCCGGCGGTACTCCGTATTCTGGAGGCTTTTGGC
TACCGTAAGGAAGACCTCCGCTACCAAAAGACTAAACAGGTTGACCTCAC
TGCTTGCCTCAACATTAAAAAATCCGGTACCGGCGGTGGCGGTGCAACCG
TAAAGTTCAAGTACAAAGGCGAAGAAAAAGAGGTAGACATCTCCAAGATC
AAGAAAGTATGGCGTGTGGGCAAGATGATCTCCTTCACCTACGACGAGGG
CGGTGGCAAGACCGGCCGTGGTGCGGTAAGCGAAAAGGACGCTCCGAAGG
AGCTCCTGCAGATGCTGGAGAAGCAGAAAAAGTGA
```

SEQ ID NO:6 PhS2 amino acid sequence with the linker and the Sso7d coding region in lower case, and the linker region in bold.

MILDVDYITEEGKPVIRLFKKENGEFKVEYDRTFRPYIYALLKDDSKIDEVRKITGERH
GKIVRIIDAEKVRKKFLGKPIEVWKLYFEHPQDVPTIREKIREHSAVVDIFEYDIPFAK
RYLIDKGLIPMEGEEELKILAFDIETLYHEGEEFGKGPIIMISYADENEAKVITWKKIDL
PYVEVVSSEREMIKRFLKVIREKDPDIIVTYNGDSFDFPYLAKRAEKLGIKLPIGRDGS
EPKMQRIGDMTAVEVKGRIHFDLYHVIRRTINLPTYTLEAVYEAIFGKPKEKVYAHEI
AEAWESGEGLERVAKYSMEDAKATYELGKEFFPMEIQLSRLVGQPLWDVSRSSTGN
LVEWFLLRKAYERNELAPNKPSEREYERRLRESYTGGYVKEPEKGLWENIVYLDFRS
LYPSIIITHNVSPDTLNLEGCKEYDVAPEVGHKFCKDIPGFIPSLLGHLLEERQKIKRK
MKASKDPIEKILLDYRQRAIKLLANSFYGYYGYAKARWYCKECAESVTAWGREYIE
LVRKELEEKFGFKVLYIDTDGLYATIPGGKSEEIKKKALEFVDYINSKLPGLLELEYEG
FYKRGFFVTKKRYALIDEEGKIITRGLEIVRRDWSEIAKETQAKVLETILKHGNVEEA
VRIVKEVTQKLAKYEIPPEKLAIYEQITPPLHEYKAIGPHVAVAKRLAARGVKIKPGM
VIGYIVLRGDGPISNRAILAEEYDLKKHKYDAEYYIENQVLPAVLRILEAFGYRKEDL
RYQKTKQVDLTACLNIKKSgtggggatvkfkykgeekevdiskikkvwrvgkmisftyd
egggktgrgavsekdapkellqmlekqkk*

-continued

```
GCTTTAAAGTTCTCTACATTGACACTGATGGTCTCTATGCGACTATTCCG
GGTGGTAAGTCTGAGGAAATTAAGAAAAAGGCTCTAGAATTTGTGGATTA
CATTAACTCGAAGCTCCCGGGTCTCCTGGAGCTCGAATATGAAGGCTTTT
ATAAACGCGGCTTCTTCGTTACCAAGAAGAGATATGCGCTGATTGATGAA
GAAGGCAAAATTATTACTCGTGGTCTCGAGATTGTGCGCCGTGATTGGAG
CGAAATTGCGAAAGAAACTCAAGCTAAAGTTCTCGAGACTATTCTCAAAC
```

SEQ ID NO:7 PhS5 nucleic acid sequence

```
ATGGATCCTGGATGCTGACTACATCACTGAAGACGGCAAACCGATTATCCG
TCTGTTCAAAAAAGAGAACGGCGAATTTAAGGTTGAGTATGATCGCAACT
TTCGTCCATACATTTACGCTCTGCTGAGAGATGATTCTCAGATTGATGAA
GTTAAAAAAATCACTGCTGAGCGCCATGGCAAGATTGTTCGTATCATTGA
TGCGGAAAAGGTAGAAAAGAAATTTCTGGGCAGACCAATCACCGTGTGGA
```

```
GACTGTATTTCGAACATCCACAAGATGTTCCGGCTATTCGCGATAAAGTT
CGCGAACATCCTGCAGTTGTTGACATCTTCGAATACGATATTCCATTTGC
AAAGCGTTACCTCATCGACAAAGGCCTGATACCAATGGAGGGCGAGGAAG
AACTCAAGCTCCTGGCGTTCGATATAGAAACCCTCTATCACGAAGGCGAA
GAGTTTGGTAAAGGCCCAATTATAATGATCAGCTATGCAGATGAAAACGA
AGCAAAGGTGATTACTTGGAAAAAAATAGATCTCCCATACGTTGAGGTTG
TATCTTCCGAGCGCGAGATGATTAAACGTTTTCTCAGAGTTATCCGCGAG
AAGGATCCGGACATTATCATTACTTATAACGGCGACTCTTTTGACTTCCC
ATATCTGGCGAAACGCGCAGAAAAACTCGGTATTAAACTGCCTCTCGGCC
GTGATGGTTCCGAGCCGAAGATGCAGCGTATCGGCGATATGACCGCTGTA
GAAATTAAGGGTCGTATCCATTTCGACCTGTATCATGTAATTACTCGTAC
TATTAACCTCCCGACTTACACTCTCGAGGCTGTATATGAAGCAATTTTTG
GTAAGCCGAAGGAGAAGGTATACGCCGATGAGATTGCAGAGGCGTGGGAA
TCCGGTAAGAACCTCGAGCGTGTTGCAAAATACTCCATGGAAGATGCAAA
GGCGACTTATGAACTCGGCAAAGAATTCCTCCCAATGGAAATCCAGCTCT
CTCGCCTGGTTGGCCAACCACTGTGGGATGTTTCTCGTTCTTCCACCGGT
AACCTCGTAGAGTGGTATCTCCTGCGCAAAGCGTACAACGCAACGAAGT
GGCTCCGAACAAGCCAGACGAAGAAGAGTATGAACGCCGTCTCCGCGAGT
CTTACACTGGTGGCTATGTTAAAGAGCCAGAAAAGGGCCTCTGGGAAAAC
CTCGTGTCCCTCGATTTTCGCGCTCTGTATCCGTCTATTATCATTACCCA
CAACGTGTCTCCGGATACTCTCAACCGCGAGGGCTGCAAAGAGTATGATA
TTGCTCCGCAAGTAGGCCACAAGTTCTGCAAGGACTTCCCGGGCTTTATT
CCGTCTCTCCTGAAACATCTGCTCGATGAACGCCAAGAGATTAAGCGTAA
```

```
AATGAAGGCGTCCAAGGATCCGATTGAAAAAAAAATGCTCGACTATCGCC
AAAGAGCGATTAAACTCCTCGCAAACTCTTTTTACGGCTATTATGGCTAT
GCAAAAGCACGCTGGTACTGTAAGGAGTGTGCTGAGTCCGTTACTGCTTG
GGGTCGCGAATACATCGAGCTCGTGTGGAAGGAGCTCGAAGAAAAGTTTG
GCTTTAAAGTTCTCTACATTGACACTGATGGTCTCTATGCGACTATTCCG
GGTGGTAAGCCTGAGGAAATTAAGAAAAAGGCTCTAGAATTTGTGAAATA
CATTAACTCGAAGCTCCCGGGTCTCCTGGAGCTCGAATATGAAGGCTTTT
ATGTTCGCGGCTTCTTCGTTACCAAGAAGAGATATGCGGTGATTGATGAA
GAAGGCAAAATTATTACTCGTGGTCTCGAGATTGTGCGCCGTGATTGGAG
CGAAATTGCGAAAGAAACTCAAGCTAGAGTTCTCGAGGCTATTCTCAAAC
ACGGCAACGTTGAAGAAGCTGTGAAAATTGTAAAAGAAGTAACCCAAAAG
CTCGCTAAATATGAAATTCCGCCAGAGAAGCTCGCGATTTATGAGCAGAT
TACTCGCCCGCTGCATGAGTATAAGGCGATTGGTCCGCACGTGGCTGTTG
CAAAGAGACTGGCTGCTAGAGGCGTGAAAGTTAGACGGGTATGGTAATT
GGCTACATTGTACTCCGCGGCGATGGTCCGATTAGCAACCGTGCAATTCT
AGCTGAGGAATACGATCTGAAAAAGCACAAGTATGACGCAGAATATTACA
TTGAGAACCAGGTGCTCCCGGCGGTACTCCGTATTCTGGAGGCTTTTGGC
TACCGTAAGGAAGACCTCCGCTGGCAAAAGACTAAACAGGTTGGCCTCAC
TTCTTGGCTCAACATTAAAAAATCCGGTACCGGCGGTGGCGGTGCAACCG
TAAAGTTCAAGTACAAAGGCGAAGAAAAAGAGGTAGACATCTCCAAGATC
AAGAAAGTATGGCGTGTGGGCAAGATGATCTCCTTCACCTACGACGAGGG
CGGTGGCAAGACCGGCCGTGGTGCGGTAAGCGAAAAGGACGCGCCGAAGG
AGCTGCTGCAGATGCTGGAGAAGCAGAAAAAGTGA
```

SEQ ID NO:8 PhS5 polypeptide sequence with the linker and the
Sso7d coding region in lower case, and the linker region in bold.
MILDADYITEDGKPIIRLFKKENGEFKVEYDRNFRPYIYALLRDDSQIDEVKKITAERH
GKIVRIIDAEKVEKKFLGRPITVWRLYFEHPQDVPAIRDKVREHPAVVDIFEYDIPFAK
RYLIDKGLIPMEGEEELKLLAFDIETLYHEGEEFGKGPIIMISYADENEAKVITWKKID
LPYVEVVSSEREMIKRFLRVIREKDPDIIITYNGDSFDFPYLAKRAEKLGIKLPLGRDG
SEPKMQRIGDMTAVEIKGRIHFDLYHVITRTINLPTYTLEAVYEAIFGKPKEKVYADEI
AEAWESGKNLERVAKYSMEDAKATYELGKEFLPMEIQLSRLVGQPLWDVSRSSTGN
LVEWYLLRKAYERNEVAPNKPDEEEYERRLRESYTGGYVKEPEKGLWENLVSLDFR
ALYPSIIITHNVSPDTLNREGCKEYDIAPQVGHKFCKDFPGFIPSLLKHLLDERQEIKRK
MKASKDPIEKKMLDYRQRAIKLLANSFYGYYGYAKARWYCKECAESVTAWGREYI
ELVWKELEEKFGFKVLYIDTDGLYATIPGGKPEEIKKKALEFVKYINSKLPGLLELEY
EGFYVRGFFVTKKRYAVIDEEGKIITRGLEIVRRDWSEIAKETQARVLEAILKHGNVE
EAVKIVKEVTQKLAKYEIPPEKLAIYEQITRPLHEYKAIGPHVAVAKRLAARGVKVRP
GMVIGYIVLRGDGPISNRAILAEEYDLKKHKYDAEYYIENQVLPAVLRILEAFGYRKE -continued DLRWQKTKQVGLTSWLNIKKSgtggggatvkfkykgeekevdiskikkvwrvgkmisft ydegggktgrgavsekdapkellqmlekqkk*

SEQ ID NO:9 PhS7 nucleic acid sequence

ATGATCCTGGATGCTGACTACATCACTGAAGACGGCAAACCGATTATCCG
TCTGTTCAAAAAAGAGAACGGCGAATTTAAGGTTGAGTATGATCGCAACT
TTCGTCCATACATTTACGCTCTGCTGAGAGATGATTCTCAGATTGATGAA
GTTAAAAAATCACTGCTGAGCGCCATGGCAAGATTGTTCGTATCATTGAT
GCGGAAAAGGTAGAAAAGAAATTTCTGGGCAGACCAATCACCGTGTGGAG
ACTGTATTTCGAACATCCACAAGATGTTCCGGCTATTCGCGATAAAGTTC
GCGAACATCCTGCAGTTGTTGACATCTTCGAATACGATATTCCATTTGCA
AAGCGTTACCTCATCGACAAAGGCCTGATACCAATGGAGGGCGAGGAAGA
ACTCAAGCTCCTGGCGTTCGATATAGAAACCCTCTATCACGAAGGCGAAG
AGTTTGGTAAAGGCCCAATTATAATGATCAGCTATGCAGATGAAAACGAA
GCAAAGGTGATTACTTGGAAAAAAATAGATCTCCCATACGTTGAGGTTGT
ATCTTCCGAGCGCGAGATGATTAAACGTTTTCTCAGAGTTATCCGCGAG
AAGGATCCGGACATTATCATTACTTATAACGGCGACTCTTTTGACTTCCC
ATATCTGGCGAAACGCGCAGAAAAACTCGGTATTAAACTGCCTCTCGGCC
GTGATGGTTCCGAGCCGAAGATGCAGCGTATCGGCGATATGACCGCTGTA
GAAATTAAGGGTCGTATCCATTTCGACCTGTATCATGTAATTACTCGTAC
TATTAACCTCCCGACTTACACTCTCGAGGCTGTATATGAAGCAATTTTTG
GTAAGCCGAAGGAGAAGGTATACGCCGATGAGATTGCAGAGGCGTGGGAA
TCCGGTAAGAACCTCGAGCGTGTTGCAAAATACTCCATGGAAGATGCAAA
GGCGACTTATGAACTCGGCAAAGAATTCCTCCCAATGGAAATCCAGCTCT
CTCGCCTGGTTGGCCAACCACTGTGGGATGTTTCTCGTTCTTCCACCGGT
AACCTCGTAGAGTGGTATCTCCTGCGCAAAGCGTACGAACGCAACGAAGT
GGCTCCGAACAAGCCAGACGAAGAAGAGTATGAACGCCGTCTCCGCGAGT
CTTACACTGGTGGCTATGTTAAAGAGCCAGAAAAGGGCCTCTGGGAAAAC
CTCGTGTCCCTCGATTTTCGCGCTCTGTATCCGTCTATTATCATTACCCA

CAACGTGTCTCCGGATACTCTCAACCGCGAGGGCTGCAGAAACTATGATG
TTGCTCCGCAAGTAGGCCACAAGTTCTGCAAGGACTTCCCGGGCTTTATT
CCGTCTCTCCTGGGCCGTCTGCTCGAGGAACGCCAAGAGATTAAGACTAA
AATGAAGGCGACCAAGGATCCGATTGAAAAAAAACTGCTCGACTATCGCC
AAAAAGCGATTAAAATCCTCGCAAACTCTTTTTACGGCTATTATGGCTAT
GCAAAAGCACGCTGGTACTGTAAGGAGTGTGCTGAGTCCGTTACTGCTTG
GGGTCGCAAATACATCGAGTTCGTGCGGAAGGAGCTCGAAGAAAAGTTTG
GCTTTAAAGTTCTCTACATTGACACTGATGGTCTCTATGCGACTATTCCG
GGTGGTAAGCCTGAGGAAATTAAGAAAAGGCTCTAGAATTTGTGAAATA
CATTAACTCGAAGCTCCCGGGTCTCCTGGAGCTCGAATATGAAGGCTTTT
ATGTTCGCGGCTTCTTCGTTACCAAGAAGAGATATGCGGTGATTGATGAA
GAAGGCAAAATTATTACTCGTGGTCTCGAGATTGTGCGCCGTGATTGGAG
CGAAATTGCGAAAGAAACTCAAGCTAGAGTTCTCGAGGCTATTCTCAAAC
ACGGCAACGTTGAAGAAGCTGTGAAAATTGTAAAAGAAGTAACCCAAAAG
CTCGCTAAATATGAAATTCCGCCAGAGAAGCTCGCGATTTATGAGCAGAT
TACTCGCCCGCTGCATGAGTATAAGGCGATTGGTCCGCACGTGGCTGTTG
CAAAGAGACTGGCTGCTAGAGGCGTGAAAGTTAGACCGGGTATGGTAATT
GGCTACATTGTACTCCGCGGCGATGGTCCGATTAGCAACCGTGCAATTCT
AGCTGAGGAATACGATCTGAAAAAGCACAAGTATGACGCAGAATATTACA
TTGAGAACCAGGTGCTCCCGGCGGTACTCCGTATTCTGGAGGCTTTTGGC
TACCGTAAGGAAGACCTCCGCTGGCAAAAGACTAAACAGGTTGGCCTCAC
TTCTTGGCTCAACATTAAAAAATCCGGTACCGGCGGTGGCGGTGCAAC
CGTAAAGTTCAAGTACAAAGGCGAAGAAAAAGAGGTAGACATCTCCAAGA
TCAAGAAAGTATGGCGTGTGGGCAAGATGATCTCCTTCACCTACGACGAG
GGCGGTGGCAAGACCGGCCGTGGTGCGGTAAGCGAAAAGGACGCGCCGAA
GGAGCTGCTGCAGATGCTGGAGAAGCAGAAAAAGTGA

SEQ ID NO:10 PhS7 polypeptide sequence with the linker and the
Sso7d coding region in lower case, and the linker region in bold.
MILDADYITEDGKPIIRLFKKENGEFKVEYDRNFRPYIYALLRDDSQIDEVKKITAERH
GKIVRIIDAEKVEKKFLGRPITVWRLYFEHPQDVPAIRDKVREHPAVVDIFEYDIPFAK
RYLIDKGLIPMEGEEELKLLAFDIETLYHEGEEFGKGPIIMISYADENEAKVITWKKID
LPYVEVVSSEREMIKRFLRVIREKDPDIIITYNGDSFDFPYLAKRAEKLGIKLPLGRDG
SEPKMQRIGDMTAVEIKGRIHFDLYHVITRTINLPTYTLEAVYEAIFGKPKEKVYADEI
AEAWESGKNLERVAKYSMEDAKTYELGKEFLPMEIQLSRLVGQPLWDVSRSSTGN LVEWYLLRKAYERNEVAPNKPDEEEYERRLRESYTGGYVKEPEKGLWENLVSLDFR
ALYPSIIITHNVSPDTLNREGCRNYDVAPQVGHKFCKDFPGFIPSLLGRLLEERQEIKT
KMKATKDPIEKKLLDYRQKAIKILANSFYGYYGYAKARWYCKECAESVTAWGRKY
IEFVRKELEEKFGFKVLYIDTDGLYATIPGGKPEEIKKKALEFVKYINSKLPGLLELEY
EGFYVRGFFVTKKRYAVIDEEGKIITRGLEIVRRDWSEIAKETQARVLEAILKHGNVE
EAVKIVKEVTQKLAKYEIPPEKLAIYEQITRPLHEYKAIGPHVAVAKRLAARGVKVRP
GMVIGYIVLRGDGPISNRAILAEEYDLKKHKYDAEYYIENQVLPAVLRILEAFGYRKE
DLRWQKTKQVGLTSWLNIKKSgtggggatvkfkykgeekevdiskikkvwrvgkmisft
ydegggktgrgavsekdapkellqmlekqkk*

SEQ ID NO:11 Hyb1 nucleic acid sequence
ATGATCCTGGATGCTGACTACATCACTGAAGACGGCAAACCGGTTATCCG
TCTCTTCAAAAAGAGAACGGCGAATTTAAGATTGAGTATGATCGCACCT
TTCGTCCATACATTTACGCTCTGCTGAGAGATGATTCTAAGATTGAGGAA
GTTAGAAAAATCACTGCTGAGCGCCATGGCAAGATTGTTCGTATCGTTGA
TGTGGAAAAGGTAAGGAAGAAATTTCTGGGCAGACCAATCAAGGTGTGGA
GACTGTATTTCGAACATCCACAAGATGTTCCGACTATTCGCGATAAAGTT
CGCGAACATCCTGCAGTTATTGACATCTTCGAATACGATATTGCATTTGC
AAAGCGTTACCTCATCGACAAAGGCCTGATACCAATGGAGGGCGAGGAAG
AACTCAAGATCCTGGCGTTCGATATAGAAACCCTCTATCACGGAAGCGAA
GAGTTTGGTAAAGGCCCAATTATAATGATCAGCTATGCAGATGAAAACGA
AGCAAAGGTGATTACTTGGAAAAACATAGATCTCCCATACGTTGAGGTTG
TATCTTCCGAGCGCGAGATGATTAAACGCTTTCTCAGAATTATCCGCGAG
AAGGATCCGGACATTATCGTTACTTATAACGGCGACTCTTTTGACCTCCC
ATATCTGGCGAAACGCGCAGAAAAACTCGGTATTAAACTGACTCTCGGCC
GTGATGGTTGCGAGGCGAAGATGCAGCGTCTCGGCGATATGACCGCTGTA
GAAGTTAAGGGTCGTATCCATTTCGACCTGTATTATGTAATTAGCCGTAC
TATTAACCTCCCGACTTACACTCTCGAGGCTGTATATGAAGCAATTTTTG
GTAAGCCGAAGGAGAAGGTATACGCCGATGATATTGCAGAGGCGTGGGAA
ACCGGTAAGGGCCTCGAGCGTGTTGCAAAATACTCCATGGAAGATGCAAA
GGCGACTTATGAACTCGGCAAAGAATTCCTCCCAATGGAAGCTCAGCTCT
CTCGCCTGGTTGGCCAACCACTGTGGGATGTTTCTCGTTCTTCCACCGGT
AACCTCGTAGAGTGGTATCCTGCGCAAAGCGTACGAACGCAACGAAGT
GGCTCCGAACAAGCCATACGAACGAGAGTATGAACGCCGTCTCCGCGAGT
CTTACACTGGTGGCTTTGTTAAAGAGCCAGAAAAGGGCCTCTGGGAAAGC
CTCGTGTCCCTCGATTTTCGCTCTCTGTATCCGTCTATTATCATTACCCA
CAACGTGTCTCCGGATACTCTCAACCGCGAGGGCTGCAAAGACTATGATA
TTGCTCCGGAAGTAGGCCACAAGTTCTGCAAGGACTTCCTTGGCTTTATT
CCGTCTCTCCTGGGGCATCTGCTCGAGGAACGCCAAGAGATTAAGACCAA AATGAAGGAGACCCANGATCCGATTGAAAAAATACTGCTCGACTATCGCC
AAAAAGCGATTAAACTCCTCGCAAACTCTTATTACGGCTATTATGGCTAT
GCAAAAGCACGCTGGTACTGTAAGGAGTGTGCTGAGTCCGTTACTGCTTG
GGGTCGCGAATACATCGAGTTCGTGTGGAAGGAGCTCGAAGAAAAGTTTG
GCTTTAAAGTTCTCTACATTGACACTGATGGTCTCTATGCGACTATTCCG
GGTGGTGAGCCTGAGGAAATTAAGAAAAAGGCTCTAGAATTTGTGAAATA
CATTAACTCGAAGCTCCCCGGTCTCTTGGAGCTCGAATATGAAGGCTTTT
ATAAGCGCGGCTTCTTCGTTACCAAGAAGAGATATGCGGTGATTGATGAA
GAAGGCAAAATTATTACTCGTGGTCTCGAGATTGTGCGCCGTGATTGGAG
CGAAATTGCGAAAGAAACTCAAGCTAAAGTTCTCGAGGCTATTCTCAAAC
ACGGCAACGTTGAAGAAGCTGTGAAAATTGTAAAAGAAATAATCGAAAAG
CTCGCTAAATATGAAATACCGCCAGAGAAGCTCGCGATTTATGAGCAGAT
TACTCGCCCGCTGCATGAGTATAAGGCGATTGGTCCGCACGTGGCTGTTG
CAAAGAAACTGGCTGCTAGAGGCGTGAAAATTAAACCGGGTATGGTAATT
GGCTACATTGTACTCCGCGGCGATGGTCCGATTAGCAAACGTGCAATTCT
AGCTGAGGAATTCGATCCGAAAAAGCACAAGTATGACGCAGAATATTACA
TTGAGAACCAGGTGCTCCCGGCGGTACTCCGTATTCTGGAGGGTTTTGGC
TACCGTAAGGAAGACCTCCGTTGGCAAAAGACTAAACAGGCTGGCCTCAC
TGCTTGGCTCAACATTAAAAAATCCGGTACCCACTAG SEQ ID NO:12 Hyb1 amino acid sequence MILDADYITEDGKPVIRLFKKENGEFKIEYDRTFRPYIYALLRDDSKIEEVRKITAERH
GKIVRIVDVEKVRKKFLGRPIKVWRLYFEHPQDVPTIRDKVREHPAVIDIFEYDIAFA
KRYLIDKGLIPMEGEEELKILAFDIETLYHGSEEFGKGPIIMISYADENEAKVITWKNID
LPYVEVVSSEREMIKRFLRIIREKDPDIIVTYNGDSFDLPYLAKRAEKLGIKLTLGRDG
CEAKMQRLGDMTAVEVKGRIHFDLYYVISRTINLPTYTLEAVYEAIFGKPKEKVYAD
DIAEAWETGKGLERVAKYSMEDAKATYELGKEFLPMEAQLSRLVGQPLWDVSRSST
GNLVEWYLLRKAYERNEVAPNKPYEREYERRLRESYTGGFVKEPEKGLWESLVSLD
FRSLYPSIIITHNVSPDTLNREGCKDYDIAPEVGHKFCKDFLGFIPSLLGHLLEERQEIK
TKMKETXDPIEKILLDYRQKAIKLLANSYYGYYGYAKARWYCKECAESVTAWGRE
YIEFVWKELEEKFGFKVLYIDTDGLYATIPGGEPEEIKKKALEFVKYINSKLPGLLELE
YEGFYKRGFFVTKKRYAVIDEEGKIITRGLEIVRRDWSEIAKETQAKVLEAILKHGNV
EEAVKIVKEIIEKLAKYEIPPEKLAIYEQITRPLHEYKAIGPHVAVAKKLAARGVKIKP
GMVIGYIVLRGDGPISKRAILAEEFDPKKHKYDAEYYIENQVLPAVLRILEGFGYRKE
DLRWQKTKQAGLTAWLNIKKS*

SEQ ID NO:13 HyS1 (Hyb1 with Sso7d at the C-terminus) nucleic acid sequence

ATGATCCTGGATGCTGACTACATCACTGAAGACGGCAAACCGGTTATCCGTCTCT
TCAAAAAGAGAACGGCGAATTTAAGATTGAGTATGATCGCACCTTTCGTCCATA
CATTTACGCTCTGCTGAGAGATGATTCTAAGATTGAGGAAGTTAGAAAAATCACT
GCTGAGCGCCATGGCAAGATTGTTCGTATCGTTGATGTGGAAAAGGTAAGGAAG
AAATTTCTGGGCAGACCAATCAAGGTGTGGAGACTGTATTTCGAACATCCACAA
GATGTTCCGACTATTCGCGATAAAGTTCGCGAACATCCTGCAGTTATTGACATCT
TCGAATACGATATTGCATTTGCAAAGCGTTACCTCATCGACAAAGGCCTGATACC
AATGGAGGGCGAGGAAGAACTCAAGATCCTGGCGTTCGATATAGAAACCCTCTA
TCACGGAAGCGAAGAGTTTGGTAAAGGCCCAATTATAATGATCAGCTATGCAGA
TGAAAACGAAGCAAAGGTGATTACTTGGAAAAACATAGATCTCCCATACGTTGA
GGTTGTATCTTCCGAGCGCGAGATGATTAAACGCTTTCTCAGAATTATCCGCGAG
AAGGATCCGGACATTATCGTTACTTATAACGGCGACTCTTTTGACCTCCCATATCT
GGCGAAACGCGCAGAAAAACTCGGTATTAAACTGACTCTCGGCCGTGATGGTTG
CGAGGCGAAGATGCAGCGTCTCGGCGATATGACCGCTGTAGAAGTTAAGGGTCG
TATCCATTTCGACCTGTATTATGTAATTAGCCGTACTATTAACCTCCCGACTTACA
CTCTCGAGGCTGTATATGAAGCAATTTTTGGTAAGCCGAAGGAGAAGGTATACG
CCGATGATATTGCAGAGGCGTGGGAAACCGGTAAGGGCCTCGAGCGTGTTGCAA
AATACTCCATGGAAGATGCAAAGGCGACTTATGAACTCGGCAAAGAATTCCTCC
CAATGGAAGCTCAGCTCTCTCGCCTGGTTGGCCAACCACTGTGGGATGTTTCTCG
TTCTTCCACCGGTAACCTCGTAGAGTGGTATCTCCTGCGCAAAGCGTACGAACGC
AACGAAGTGGCTCCGAACAAGCCATACGAACGAGAGTATGAACGCCGTCTCCGC
GAGTCTTACACTGGTGGCTTTGTTAAAGAGCCAGAAAAGGGCCTCTGGGAAAGC
CTCGTGTCCCTCGATTTTCGCTCTCTGTATCCGTCTATTATCATTACCCACAACGT

-continued

```
GTCTCCGGATACTCTCAACCGCGAGGGCTGCAAAGACTATGATATTGCTCCGGAA
GTAGGCCACAAGTTCTGCAAGGACTTCCTTGGCTTTATTCCGTCTCTCCTGGGGC
ATCTGCTCGAGGAACGCCAAGAGATTAAGACCAAAATGAAGGAGACCCANGATC
CGATTGAAAAAATACTGCTCGACTATCGCCAAAAAGCGATTAAACTCCTCGCAA
ACTCTTATTACGGCTATTATGGCTATGCAAAAGCACGCTGGTACTGTAAGGAGTG
TGCTGAGTCCGTTACTGCTTGGGGTCGCGAATACATCGAGTTCGTGTGGAAGGAG
CTCGAAGAAAGTTTGGCTTTAAAGTTCTCTACATTGACACTGATGGTCTCTATG
CGACTATTCCGGGTGGTGAGCCTGAGGAAATTAAGAAAAAGGCTCTAGAATTTG
TGAAATACATTAACTCGAAGCTCCCCGGTCTCTTGGAGCTCGAATATGAAGGCTT
TTATAAGCGCGGCTTCTTCGTTACCAAGAAGAGATATGCGGTGATTGATGAAGAA
GGCAAAATTATTACTCGTGGTCTCGAGATTGTGCGCCGTGATTGGAGCGAAATTG
CGAAAGAAACTCAAGCTAAAGTTCTCGAGGCTATTCTCAAACACGGCAACGTTG
AAGAAGCTGTGAAAATTGTAAAAGAAATAATCGAAAAGCTCGCTAAATATGAAA
TACCGCCAGAGAAGCTCGCGATTTATGAGCAGATTACTCGCCCGCTGCATGAGTA
TAAGGCGATTGGTCCGCACGTGGCTGTTGCAAAGAAACTGGCTGCTAGAGGCGT
GAAAATTAAACCGGGTATGGTAATTGGCTACATTGTACTCCGCGGCGATGGTCCG
ATTAGCAAACGTGCAATTCTAGCTGAGGAATTCGATCCGAAAAAGCACAAGTAT
GACGCAGAATATTACATTGAGAACCAGGTGCTCCCGGCGGTACTCCGTATTCTGG
AGGGTTTTGGCTACCGTAAGGAAGACCTCCGTTGGCAAAAGACTAAACAGGCTG
GCCTCACTGCTTGGCTCAACATTAAAAAATCCGGTACCGGCGGTGGCGGTGCAAC
CGTAAAGTTCAAGTACAAAGGCGAAGAAAAGAGGTAGACATCTCCAAGATCAA
GAAAGTATGGCGTGTGGGCAAGATGATCTCCTTCACCTACGACGAGGGCGGTGG
CAAGACCGGCCGTGGTGCGGTAAGCGAAAAGGACGCGCCGAAGGAGCTGCTGC
AGATGCTGGAGAAGCAGAAAAAGTGA
```

SEQ ID NO:14 HyS1 (Hyb1 with Sso7d at the C-terminus) polypeptide
sequence with the linker and the Sso7d coding region in lower case,
and the linker region in bold.

```
MILDADYITEDGKPVIRLFKKENGEFKIEYDRTFRPYIYALLRDDSKIEEVRKITAERH
GKIVRIVDVEKVRKKFLGRPIKVWRLYFEHPQDVPTIRDKVREHPAVIDIFEYDIAFA
KRYLIDKGLIPMEGEEELKILAFDIETLYHGSEEFGKGPIIMISYADENEAKVITWKNID
LPYVEVVSSEREMIKRFLRIIREKDPDIIVTYNGDSFDLPYLAKRAEKLGIKLTLGRDG
CEAKMQRLGDMTAVEVKGRIHFDLYYVISRTINLPTYTLEAVYEAIFGKPKEKVYAD
DIAEAWETGKGLERVAKYSMEDAKATYELGKEFLPMEAQLSRLVGQPLWDVSRSST
GNLVEWYLLRKAYERNEVAPNKPYEREYERRLRESYTGGFVKEPEKGLWESLVSLD
FRSLYPSIIITHNVSPDTLNREGCKDYDIAPEVGHKFCKDFLGFIPSLLGHLLEERQEIK
TKMKETXDPIEKILLDYRQKAIKLLANSYYGYYGYAKARWYCKECAESVTAWGRE
YIEFVWKELEEKFGFKVLYIDTDGLYATIPGGEPEEIKKKALEFVKYINSKLPGLLELE
YEGFYKRGFFVTKKRYAVIDEEGKIITRGLEIVRRDWSEIAKETQAKVLEAILKHGNV
```

-continued

EEAVKIVKEIIEKLAKYEIPPEKLAIYEQITRPLHEYKAIGPHVAVAKKLAARGVKIKP

GMVIGYIVLRGDGPISKRAILAEEFDPKKHKYDAEYYIENQVLPAVLRILEGFGYRKE

DLRWQKTKQAGLTAWLNIKKSgtggggatvkfkykgeekevdiskikkvwrvgkmisftydeggg ktgrgavsekdapkellqmlekqkk*

SEQ ID NO:15 Hyb2 (premature stop codon in bold) nucleic acid sequence

ATGATCCTGGATGCTGACTACATCACTGAAGAAGGCAAACCGGTTATCCGTATCT

TCAAAAAAGAGAACGGCGAATTTAAGGTTGAGTATGATCGCAACTTTCGTCCAT

ACATTTACGCTCTGCTGGAAGATGATTCTAAGATTGATGAAGTTAGAAAAATCAC

TGCTGAGCGCCATGGCAAGATTGTTCGTATCGTTGATGCGGAAAAGGTAGAGAA

GAAATTTCTGGGCAGACCAATCACGGTGTGGAAACTGTATTTCGAACATCCACAA

GATGTTCCGACTATTCGCGAGAAAATTCGCGAACATTCTGCAGTTGTTGGCATCT

TCGAATACGATATTCCATTTGCAAAGAGTTACCTCATCGACAAAGGCCTGATACC

AATGGAGGGCGAGGAAGAACTCAAGCTCCTGGCGTTCGATATAGAAACCCTCTA

TCACGAAGGCGAAGAGTTTGCTAAAGGCCCAATTATAATGATCAGCTATGCAGA

TGAAGACGAAGCAAAGGTGATTACTTGGAAAAAAATAGATCTCCCATACGTTGA

GGTTGTATCTTCCGAGCGCGAGATGATTAAGCGCTTTCTCAGAGTTATCCGCGAG

AAGGATCCGGACGTTATCGTTACTTATAACGGCGACTCTTTTGACCTCCCATATCT

GGCGAAACGCGCAGAAAAACTCGGTATTAAACTGCCTCTCGGCCGTGATGGTTC

CGAGCCGAAGATGCAGCGTCTCGGCGATATGACCGCTGTAGAAGTTAAGGGTCG

TATCCATTTCGACCTGTATCATGTAATTAGCCGTACTATTAACCTCCCGACTTACA

CTCTCGAGGCTGTATATGAAGCAATTTTTGGTAAGCCGAAGGAGAAGGTATACG

CCGATGAGATTGCAGGGGCGTGGGAAACCGGTGAGGACCTCGAGCGTGTTGCAA

AATACTCCATGGAAGATGCAAAGGCGATTTATGAACTCGGCAAAGAATTCTTCCC

AATGGAAGTTCAGCTCCCTCGCCTGGTTGGCCAACCACTGTGGGATGTTTCTCGT

TCTTCCACCGGTAACCTCGTAGAGTGGTTGCTCCTGCGCAAAGCGTACGAACGCA

ACGAACTGGCTCCGAACAAGCCAGCCGAACAAGAGTATGAACGCCGTCTCCGCG

AGTCTTACACTGGTGGCTTTGTTAAAGAGCCAGAAAAGGGCCTCTGGGAAGACC

TCGTGTCCCTCGATTTTCGCGCTCTGTATCCGTCTATTATCATTACCCACAACGTG

TCTCCGGATACTCTCAACCGCGAGGGCTGCAAAGACTATGATATTGCTCCGGAAG

TAGGCCACAAGTTCTGCAAGGACTTCCTTGGCTTTATTCCGTCTCTCCTGGGGCAT

CTGCTCGAGGAACGCCAAGAGATTAAGACCAAAATGAAGGAGACCCANGATCCG

ATTGAAAAAATACTGCTCGACTATCGCCAAAAAGCGATTAAACTCCTCGCAAACT

CTTATTACGGCTATTATGGCTATGCAAAAGCACGCTGGTACTGTAAGGAGTGTGC

TGAGTCCGTTACTGCTTGGGGTCGCGAATACATCGAGTTCGTGTGGAAGGAGCTC

GAAGAAAAGTTTGGCTTTAAAGTTCTCTACATTGACACTGATGGTCTCTATGCGA

CTATTCCGGGTGGTGAGCCTGAGGAAATTAAGAAAAAGGCTCTAGAATTTGTGA

AATACATTAACTCGAAGCTCCCCGGTCTCTTGGAGCTCGAATATGAAGGCTTTTA

TAAGCGCGGCTTCTTCGTTACCAAGAAGAGATATGCGGTGATTGATGAAGAAGG

CAAAATTATTACTCGTGGTCTCGAGATTGTGCGCCGTGATTGGAGCGAAATTGCG

-continued

AAAGAAACTCAAGCTAAAGTTCTCGAGGCTATTCTCAAACACGGCAACGTTGAA

GAAGCTGTGAAAATTGTAAAAGAAATAATCGAAAAGCTCGCTAAATATGAAATA

CCGCCAGAGAAGCTCGCGATTTATGAGCAGATTACTCGCCCGCTGCATGAGTATA

AGGCGATTGGTCCGCACGTGGCTGTTGCAAAGAAACTGGCTGCTAGAGGCGTGA

AAATTAAACCGGGTATGGTAATTGGCTACATTGTACTCCGCGGCGATGGTCCGAT

TAGCAACCGTGCAATTCTAGCTGAGGAATTCGATCTGAGAAAGCACAAGTATGA

CGCAGAATATTACATTGAGAACCAGGTGCTCCCGGCGGTACTCCGTATTCTGGAG

GGTTTTGGCTACCGTAAGGAAGACCTCCGTTAGCAAAAGACTAAACAGGCTGGA

CTCACTGCTTGGCTCATCATTAAAAAATCCGGTACCCACTAGTGC

SEQ ID NO:16 Hyb2 polypeptide sequence

MILDADYITEEGKPVIRIFKKENGEFKVEYDRNFRPYIYALLEDDSKIDEVRKITAERH

GKIVRIVDAEKVEKKFLGRPITVWKLYFEHPQDVPTIREKIREHSAVVGIFEYDIPFAK

SYLIDKGLIPMEGEEELKLLAFDIETLYHEGEEFAKGPIIMISYADEDEAKVITWKKID

LPYVEVVSSEREMIKRFLRVIREKDPDVIVTYNGDSFDLPYLAKRAEKLGIKLPLGRD

GSEPKMQRLGDMTAVEVKGRIHFDLYHVISRTINLPTYTLEAVYEAIFGKPKEKVYA

DEIAGAWETGEDLERVAKYSMEDAKAIYELGKEFFPMEVQLPRLVGQPLWDVSRSS

TGNLVEWLLLRKAYERNELAPNKPAEQEYERRLRESYTGGFVKEPEKGLWEDLVSL

DFRALYPSIIITHNVSPDTLNREGCKDYDIAPEVGHKFCKDFLGFIPSLLGHLLEERQEI

KTKMKETXDPIEKILLDYRQKAIKLLANSYYGYYGYAKARWYCKECAESVTAWGR

EYIEFVWKELEEKFGFKVLYIDTDGLYATIPGGEPEEIKKKALEFVKYINSKLPGLLEL

EYEGFYKRGFFVTKKRYAVIDEEGKIITRGLEIVRRDWSEIAKETQAKVLEAILKHGN

VEEAVKIVKEIIEKLAKYEIPPEKLAIYEQITRPLHEYKAIGPHVAVAKKLAARGVKIK

PGMVIGYIVLRGDGPISNRAILAEEFDLRKHKYDAEYYIENQVLPAVLRILEGFGYRK

EDLR*

SEQ ID NO:17 Hyb3 (premature stop codon in bold) nucleic acid sequence

ATGATCCTGGATGCTGACTACATCACTGAAGAAGGCAAACCGGTTATCCGTATCT

TCAAAAAAGAGAACGGCGAATTTAAGGTTGAGTATGATCGCAACTTTCGTCCAT

ACATTTACGCTCTGCTGGAAGATGATTCTAAGATTGATGAAGTTAGAAAAATCAC

TGCTGAGCGCCATGGCAAGATTGTTCGTATCGTTGATGCGGAAAAGGTAGAGAA

GAAATTTCTGGGCAGACCAATCACGGTGTGGAAACTGTATTTCGAACATCCACAA

GATGTTCCGACTATTCGCGAGAAAATTCGCAACATTCTGCAGTTGTTGGCATCT

TCGAATACGATATTCCATTTGCAAAGAGTTACCTCATCGACAAAGGCCTGATACC

AATGGAGGGCGAGGAAGAACTCAAGCTCCTGGCGTTCGATATAGAAACCCTCTA

TCACGAAGGCGAAGAGTTTGCTAAAGGCCCAATTATAATGATCAGCTATGCAGA

TGAAGACGAAGCAAAGGTGATTACTTGGAAAAAAATAGATCTCCCATACGTTGA

GGTTGTATCTTCCGAGCGCGAGATGATTAAGCGCTTTCTCAGAGTTATCCGCGAG

AAGGATCCGGACGTTATCGTTACTTATAACGGCGACTCTTTTGACCTCCCATATCT

-continued

```
GGCGAAACGCGCAGAAAAACTCGGTATTAAACTGCCTCTCGGCCGTGATGGTTC
CGAGCCGAAGATGCAGCGTCTCGGCGATATGACCGCTGTAGAAGTTAAGGGTCG
TATCCATTTCGACCTGTATCATGTAATTAGCCGTACTATTAACCTCCCGACTTACA
CTCTCGAGGCTGTATATGAAGCAATTTTTGGTAAGCCGAAGGAGAAGGTATACG
CCGATGAGATTGCAGGGCGTGGGAAACCGGTGAGGACCTCGAGCGTGTTGCAA
AATACTCCATGGAAGATGCAAAGGCGATTTATGAACTCGGCAAAGAATTCTTCCC
AATGGAAGTTCAGCTCCCTCGCCTGGTTGGCCAACCACTGTGGGATGTTTCTCGT
TCTTCCACCGGTAACCTCGTAGAGTGGTTGCTCCTGCGCAAAGCGTACGAACGCA
ACGAACTGGCTCCGAACAAGCCAGCCGAACAAGAGTATGAACGCCGTCTCCGCG
AGTCTTACACTGGTGGCTTTGTTAAAGAGCCAGAAAAGGGCCTCTGGGAAGACC
TCGTGTCCCTCGATTTTCGCGCTCTGTATCCGTCTATTATCATTACCCACAACGTG
TCTCCGGATACTCTCAACCGCGAGGGCTGCAAAGACTATGATATTGCTCCGGAAG
TAGGCCACAAGTTCTGCAAGGACTTCCTTGGCTTTATTCCGTCTCTCCTGGGGCAT
CTGCTCGAGGAACGCCAAGAGATTAAGACCAAAATGAAGGAGACCCANGATCCG
ATTGAAAAAATACTGCTCGACTATCGCCAAAAAGCGATTAAACTCCTCGCAAACT
CTTATTACGGCTATTATGGCTATGCAAAAGCACGCTGGTACTGTAAGGAGTGTGC
TGAGTCCGTTACTGCTTGGGGTCGCGAATACATCGAGTTCGTGTGGAAGGAGCTC
GAAGAAAAGTTTGGCTTTAAAGTTCTCTACATTGACACTGATGGTCTCTATGCGA
CTATTCCGGGTGGTGAGCCTGAGGAAATTAAGAAAAAGGCTCTAGAATTTGTGA
AATACATTAACTCGAAGCTCCCCGGTCTCTTGGAGCTCGAATATGAAGGCTTTTA
TAAGCGCGGCTTCTTCGTTACCAAGAAGAGATATGCGGTGATTGATGAAGAAGG
CAAAATTATTACTCGTGGTCTCGAGATTGTGCGCCGTGATTGGAGCGAAATTGCG
AAAGAAACTCAAGCTAAAGTTCTCGAGGCTATTCTCAAACACGGCAACGTTGAA
GAAGCTGTGAAAATTGTAAAAGAAATAATCGAAAAGCTCGCTAAATATGAAATA
CCGCCAGAGAAGCTCGCGATTTATGAGCAGATTACTCGCCCGCTGCATGAGTATA
AGGCGATTGGTCCGCACGTGGCTGTTGCAAAGAAACTGGCTGCTAGAGGCGTGA
AAATTAAACCGGGTATGGTAATTGGCTACATTGTACTCCGCGGCGATGGTCCGAT
TAGCAACCGTGCAATTCTAGCTGAGGAATTCGATCTGAGAAAGCACAAGTATGA
CGCAGAATATTACATTGAGAACCAGGTGCTCCCGGCGGTACTCCGTATTCTGGAG
GGTTTTGGCTACCGTAAGGAAGACCTCCGTTAGCAAAAGACTAAACAGGCTGGA
CTCACTGCTTGGCTCATCATTAAAAAATCCGGTACCCACTAGTGC
```

SEQ ID NO:18 Hyb3 polypeptide sequence

```
MILDADYITEEGKPVIRIFKKENGEFKVEYDRNFRPYIYALLEDDSKIDEVRKITAERH
GKIVRIVDAEKVEKKFLGRPITVWKLYFEHPQDVPTIREKIREHSAVVGIFEYDIPFAK
SYLIDKGLIPMEGEEELKLLAFDIETLYHEGEEFAKGPIIMISYADEDEAKVITWKKID
LPYVEVVSSEREMIKRFLRVIREKDPDVIVTYNGDSFDLPYLAKRAEKLGIKLPLGRD
GSEPKMQRLGDMTAVEVKGRIHFDLYHVISRTINLPTYTLEAVYEAIFGKPKEKVYA
DEIAGAWETGEDLERVAKYSMEDAKAIYELGKEFFPMEVQLPRLVGQPLWDVSRSS
TGNLVEWLLLRKAYERNELAPNKPAEQEYERRLRESYTGGFVKEPEKGLWEDLVSL
```

-continued

DFRALYPSIIITHNVSPDTLNREGCKDYDIAPEVGHKFCKDFLGFIPSLLGHLLEERQEI

KTKMKETXDPIEKILLDYRQKAIKLLANSYYGYYGYAKARWYCKECAESVTAWGR

EYIEFVWKELEEKFGFKVLYIDTDGLYATIPGGEPEEIKKKALEFVKYINSKLPGLLEL

EYEGFYKRGFFVTKKRYAVIDEEGKIITRGLEIVRRDWSEIAKETQAKVLEAILKHGN

VEEAVKIVKEIIEKLAKYEIPPEKLAIYEQITRPLHEYKAIGPHVAVAKKLAARGVKIK

PGMVIGYIVLRGDGPISNRAILAEEFDLRKHKYDAEYYIENQVLPAVLRILEGFGYRK

EDLR*

SEQ ID NO:19 HyS4 (with Sso7d at the C-terminus) nucleic acid sequence

ATGATCCTGGATGCTGACTACATCACTGAAGAAGGCAAACCGGTTATCCGTATCT

TCAAAAAAGAGAACGGCGAATTTAAGGTTGAGTATGATCGCAACTTTCGTCCAT

ACATTTACGCTCTGCTGGAAGATGATTCTAAGATTGATGAAGTTAGAAAAATCAC

TGCTGAGCGCCATGGCAAGATTGTTCGTATCGTTGATGCGGAAAAGGTAGAGAA

GAAATTTCTGGGCAGACCAATCACGGTGTGGAAACTGTATTTCGAACATCCACAA

GATGTTCCGACTATTCGCGAGAAAATTCGCGAACATTCTGCAGTTGTTGGCATCT

TCGAATACGATATTCCATTTGCAAAGAGTTACCTCATCGACAAAGGCCTGATACC

AATGGAGGGCGAGGAAGAACTCAAGCTCCTGGCGTTCGATATAGAAACCCTCTA

TCACGAAGGCGAAGAGTTTGCTAAAGGCCCAATTATAATGATCAGCTATGCAGA

TGAAGACGAAGCAAAGGTGATTACTTGGAAAAAAATAGATCTCCCATACGTTGA

GGTTGTATCTTCCGAGCGCGAGATGATTAAGCGCTTTCTCAGAGTTATCCGCGAG

AAGGATCCGGACGTTATCGTTACTTATAACGGCGACTCTTTTGACCTCCCATATCT

GGCGAAACGCGCAGAAAAACTCGGTATTAAACTGCCTCTCGGCCGTGATGGTTC

CGAGCCGAAGATGCAGCGTCTCGGCGATATGACCGCTGTAGAAGTTAAGGGTCG

TATCCATTTCGACCTGTATCATGTAATTAGCCGTACTATTAACCTCCCGACTTACA

CTCTCGAGGCTGTATATGAAGCAATTTTTGGTAAGCCGAAGGAGAAGGTATACG

CCGATGAGATTGCAGGGGCGTGGGAAACCGGTGAGGACCTCGAGCGTGTTGCAA

AATACTCCATGGAAGATGCAAAGGCGATTTATGAACTCGGCAAAGAATTCTTCCC

AATGGAAGTTCAGCTCCCTCGCCTGGTTGCCAACCACTGTGGGATGTTTCTCGT

TCTTCCACCGGTAACCTCGTAGAGTGGTTGCTCCTGCGCAAAGCGTACGAACGCA

ACGAACTGGCTCCGAACAAGCCAGCCGAACAAGAGTATGAACGCCGTCTCCGCG

AGTCTTACACTGGTGGCTTTGTTAAAGAGCCAGAAAAGGGCCTCTGGGAAGACC

TCGTGTCCCTCGATTTTCGCGCTCTGTATCCGTCTATTATCATTACCCACAACGTG

TCTCCGGATACTCTCAACCGCGAGGGCTGCAAAGACTATGATATTGCTCCGGAAG

TAGGCCACAAGTTCTGCAAGGACTTCCTTGGCTTTATTCCGTCTCTCCTGGGGCAT

CTGCTCGAGGAACGCCAAGAGATTAAGACCAAAATGAAGGAGACCCANGATCCG

ATTGAAAAAATACTGCTCGACTATCGCCAAAAAGCGATTAAACTCCTCGCAAACT

CTTATTACGGCTATTATGGCTATGCAAAAGCACGCTGGTACTGTAAGGAGTGTGC

TGAGTCCGTTACTGCTTGGGGTCGCGAATACATCGAGTTCGTGTGGAAGGAGCTC

GAAGAAAAGTTTGGCTTTAAAGTTCTCTACATTGACACTGATGGTCTCTATGCGA

-continued

```
CTATTCCGGGTGGTGAGCCTGAGGAAATTAAGAAAAAGGCTCTAGAATTTGTGA

AATACATTAACTCGAAGCTCCCCGGTCTCTTGGAGCTCGAATATGAAGGCTTTTA

TAAGCGCGGCTTCTTCGTTACCAAGAAGAGATATGCGGTGATTGATGAAGAAGG

CAAAATTATTACTCGTGGTCTCGAGATTGTGCGCCGTGATTGGAGCGAAATTGCG

AAAGAAACTCAAGCTAAAGTTCTCGAGGCTATTCTCAAACACGGCAACGTTGAA

GAAGCTGTGAAAATTGTAAAAGAAATAATCGAAAAGCTCGCTAAATATGAAATA

CCGCCAGAGAAGCTCGCGATTTATGAGCAGATTACTCGCCCGCTGCATGAGTATA

AGGCGATTGGTCCGCACGTGGCTGTTGCAAAGAAACTGGCTGCTAGAGGCGTGA

AAATTAAACCGGGTATGGTAATTGGCTACATTGTACTCCGCGGCGATGGTCCGAT

TAGCAAACGTGCAATTCTAGCTGAGGAATTCGATCCGAAAAAGCACAAGTATGA

CGCAGAATATTACATTGAGAACCAGGTGCTCCCGGCGGTACTCCGTATTCTGGAG

GGTTTTGGCTACCGTAAGGAAGACCTCCGTTGGCAAAAGACTAAACAGGCTGGC

CTCACTGCTTGGCTCAACATTAAAAAATCCGGTACCGGCGGTGGCGGTGCAACCG

TAAAGTTCAAGTACAAAGGCGAAGAAAAAGAGGTAGACATCTCCAAGATCAAG

AAAGTATGGCGTGTGGGCAAGATGATCTCCTTCACCTACGACGAGGGCGGTGGC

AAGACCGGCCGTGGTGCGGTAAGCGAAAAGGACGCGCCGAAGGAGCTGCTGCA

GATGCTGGAGAAGCAGAAAAAGTGA
```

SEQ ID NO:20 HyS4 (with Sso7d at the C-terminus) polypeptide sequence with the linker and the Sso7d coding region in lower case, and the linker region in bold.

MILDADYITEEGKPVIRIFKKENGEFKVEYDRNFRPYIYALLEDDSKIDEVRKITAERH

GKIVRIVDAEKVEKKFLGRPITVWKLYFEHPQDVPTIREKIREHSAVVGIFEYDIPFAK

SYLIDKGLIPMEGEEELKLLAFDIETLYHEGEEFAKGPIIMISYADEDEAKVITWKKID

LPYVEVVSSEREMIKRFLRVIREKDPDVIVTYNGDSFDLPYLAKRAEKLGIKLPLGRD

GSEPKMQRLGDMTAVEVKGRIHFDLYHVISRTINLPTYTLEAVYEAIFGKPKEKVYA

DEIAGAWETGEDLERVAKYSMEDAKAIYELGKEFFPMEVQLPRLVGQPLWDVSRSS

TGNLVEWLLLRKAYERNELAPNKPAEQEYERRLRESYTGGFVKEPEKGLWEDLVSL

DFRALYPSIIITHNVSPDTLNREGCKDYDIAPEVGHKFCKDFLGFIPSLLGHLLEERQEI

KTKMKETXDPIEKILLDYRQKAIKLLANSYYGYYGYAKARWYCKECAESVTAWGR

EYIEFVWKELEEKFGFKVLYIDTDGLYATIPGGEPEEIKKKALEFVKYINSKLPGLLEL

EYEGFYKRGFFVTKKRYAVIDEEGKIITRGLEIVRRDWSEIAKETQAKVLEAILKHGN

VEEAVKIVKEIIEKLAKYEIPPEKLAIYEQITRPLHEYKAIGPHVAVAKKLAARGVKIK

PGMVIGYIVLRGDGPISKRAILAEEFDPKKHKYDAEYYIENQVLPAVLRILEGFGYRK

EDLRWQKTKQAGLTAWLNIKKSgtggggatvkfkykgeekevdiskikkvwrvgkmisf tydegggktgrgavsekdapkellqmlekqkk*

SEQ ID NO: 21: Sso7d coding region:
ACCGTAAAGTTCAAGTACAAAGGCGAAGAAAAAGAGGTAGACATCTCCA
AGATCAAGAAAGTATGGCGTGTGGGCAAGATGATCTCCTTCACCTACGA
CGAGGGCGGTGGCAAGACCGGCCGTGGTGCGGTAAGCGAAAAGGACGCG
CCGAAGGAGCTGCTGCAGATGCTGGAGAAGCAGAAAAAGTGA SEQ ID NO: 22 Sso7d binding domain:
ATVKFKYKGEEKEVDISKIKKVWRVGKMISFTYDEGGGKTGRGAVSEKDA
PKELLQMLEKQKK SEQ ID NO: 23
signature amino acid sequence
common to polymerases of the invention
YGYYGYAKARWYCKECAESVTAWGR SEQ ID NO: 24 Parent Pyrococcus
furiosus (Pfu) polymerase polypeptide sequence
MILDVDYITEEGKPVIRLFKKENGKFKIEHDRTFRPYIYALLRDDSKIEE
VKKITGERHGKIVRIVDVEKVEKKFLGKPITVWKLYLEHPQDVPTIREKV
REHPAVVDIFEYDIPFAKRYLIDKGLIPMEGEEELKILAFDIETLYHEGE
EFGKGPIIMISYADENEAKVITWKNIDLPYVEVVSSEREMIKRFLRIIRE
KDPDIIVTYNGDSFDFPYLAKRAEKLGIKLTIGRDGSEPKMQRIGDMTAV
EVKGRIHFDLYHVITRTINLPTYTLEAVYEAIFGKPKEKVYADEIAKAWE
SGENLERVAKYSMEDAKATYELGKEFLPMEIQLSRLVGQPLWDVSRSSTG
NLVEWFLLRKAYERNEVAPNKPSEEEYQRRLRESYTGGFVKEPEKGLWEN
IVYLDFRALYPSIIITHNVSPDTLNLEGCKNYDIAPQVGHKFCKDIPGFI
PSLLGHLLEERQKIKTKMKETQDPIEKILLDYRQKAIKLLANSFYGYYGY
AKARWYCKECAESVTAWGRKYIELVWKELEEKFGFKVLYIDTDGLYATIP
GGESEEIKKKALEFVKYINSKLPGLLELEYEGFYKRGFFVTKKRYAVIDE
EGKVITRGLEIVRRDWSEIAKETQARVLETILKHGDVEEAVRIVKEVIQK
LANYEIPPEKLAIYEQITRPLHEYKAIGPHVAVAKKLAAKGVKIKPGMVI
GYIVLRGDGPISNRAILAEEEYDPKKHKYDAEYYIENQVLPAVLRILEGFG
YRKEDLRYQKTRQVGLTSWLNIKKS SEQ ID NO: 25 parent Pyrococcus sp.. GD-B
(Deep Vent ®) polymerase polypeptide sequence
MILDADYITEDGKPIIRIFKKENGEFKVEYDRNFRPYIYALLKDDSQIDE
VRKITAERHGKIVRIIDAEKVRKKFLGRPIEVWRLYFEHPQDVPAIRDKI
REHSAVIDIFEYDIPFAKRYLIDKGLIPMEGDEELKLLAFDIETLYHEGE
EFAKGPIIMISYADEEEAKVITWKKIDLPYVEVVSSEREMIKRFLKVIRE
KDPDVIITYNGDSFDLPYLVKRAEKLGIKLPLGRDGSEPKMQRLGDMTAV
EIKGRIHFDLYHVIRRTINLPTYTLEAVYEAIFGKPKEKVYAHEIAEAWE
TGKGLERVAKYSMEDAKVTYELGREFFPMEAQLSRLVGQPLWDVSRSSTG
NLVEWYLLRKAYERNELAPNKPDEREYERRLRESYAGGYVKEPEKGLWEG
LVSLDFRSLYPSIIITHNVSPDTLNREGCREYDVAPEVGHKFCKDFPGFI
PSLLKRLLDERQEIKRKMKASKDPIEKKMLDYRQRAIKILANSYYGYYGY
AKARWYCKECAESVTAWGREYIEFVRKELEEKFGFKVLYIDTDGLYATIP
GAKPEEIKKKALEFVDYINAKLPGLLELEYEGFYVRGFFVTKKKYALIDE
EGKIITRGLEIVRRDWSEIAKETQAKVLEAILKHGNVEEAVKIVKEVTEK
LSKYEIPPEKLVIYEQITRPLHEYKAIGPHVAVAKRLAARGVKVRPGMVI
GYIVLRGDGPISKRAILAEEFDLRKHKYDAEYYIENQVLPAVLRILEAFG
YRKEDLRWQKTKQTGLTAWLNIKKK SEQ ID NO: 26
Amino acid sequences of designed hybrid protein
The "X" residue represents a hybrid
protein position that is encoded by a degeneracy.
The residue at that position is typically either
that of the Pfu parent or the Deep Vent ® parent.
MILDXDYITEXGKPXIRXFKKENGXFKXEXDRXFRPYIYALLXDDSXIXE
VXKITXERHGKIVRIXDXEKVXKKFLGXPIXVWXLYXEHPQDVPXIRXKX
REHXAVXDIFEYDIPFAKRYLIDKGLIPMEGXEELKXLAFDIETLYHEGE
EFXKGPIIMISYADEXEAKVITWKXIDLPYVEVVSSEREMIKRFLXXIRE
KDPDXIXTYNGDSFDXPYLXKRAEKLGIKLXXGRDGSEPKMQRXGDMTAV
EXKGRIHFDLYHVIXRTINLPTYTLEAVYEAIFGKPKEKVYAXEIAXAWE
XGXXLERVAKYSMEDAKXTYELGXEFXPMEXQLSRLVGQPLWDVSRSSTG
NLVEWXLLRKAYERNEXAPNKPXEXEYXRRLRESYXGGXVKEPEKGLWEX
XVXLDFRXLYPSIIITHNVSPDTLNXEGCXXYDXAPXVGHKFCKDXPGFI
PSLLXXLLXERQXIKXKMKXXXDPIEKXXLDYRQXAIKXLANSXYGYYGY
AKARWYCKECAESVTAWGRXYIEXVXKELEEKFGFKVLYIDTDGLYATIP
GXXXEEIKKKALEFVKYINXKLPGLLELEYEGFYXRGFFVTKKXYAXIDE
EGKXITRGLEIVRRDWSEIAKETQAXVLEXILKHGXVEEAVXIVKEVXXK
LXXYEIPPEKLXIYEQITRPLHEYKAIGPHVAVAKXLAAXGVKXXPGMVI
GYIVLRGDGPISXRAILAEEXDXXKHKYDAEYYIENQVLPAVLRILEXFG
YRKEDLRXQKTXQXGLTXWLNIKKS

What is claimed is:

1. A hybrid polymerase having polymerase activity, wherein the polymerase comprises the amino acid sequence of SEQ ID NO:2.

2. A method of amplifying a target sequence using a hybrid polymerase, the method comprising the steps of:

providing a polymerase according to claim 1,
combining the polymerase in an amplification reaction mixture, and
amplifying the target sequence.

* * * * *

SEQUENCE LISTING

<160> NUMBER OF SEQ ID NOS: 49

<210> SEQ ID NO 1
<211> LENGTH: 2325
<212> TYPE: DNA
<213> ORGANISM: Artificial Sequence
<220> FEATURE:
<223> OTHER INFORMATION: Description of Artificial Sequence:full-length assembled hybrid polymerase clone Phy1

<400> SEQUENCE: 1

```
atgatcctgg atgctgacta catcactgaa gaaggcaaac cggttatccg tctgttcaaa      60
aaagagaacg gcgaatttaa gattgagcat gatcgcacct ttcgtccata catttacgct     120
ctgctgaaag atgattctaa gattgaggaa gttaaaaaaa tcactgctga gcgccatggc     180
aagattgttc gtatcgttga tgcggaaaag gtagaaaaga aatttctggg cagaccaatc     240
accgtgtgga gactgtattt cgaacatcca caagatgttc gactattccg cgagaaaatt     300
cgcgaacatt ctgcagttgt tgacatcttc gaatacgata ttccatttgc aaagcgttac     360
ctcatcgaca aaggcctgat accaatggag ggcgatgaag aactcaagct cctggcgttc     420
gatatagaaa ccctctatca cgaaggcgaa gagtttggta aaggcccaat tataatgatc     480
agctatgcag atgaagaaga agcaaaggtg attacttgga aaaaaataga tctcccatac     540
gttgaggttg tatcttccga gcgcgagatg attaagcgct ttctcaaaat tatccgcgag     600
aaggatccgg acattatcat tacttataac ggcgactctt ttgacctccc atatctggcg     660
aaacgcgcag aaaaactcgg tattaaactg actatcggcc gtgatggttc cgagccgaag     720
atgcagcgta tcggcgatat gaccgctgta gaagttaagg tcgtatcca tttcgacctg     780 tatcatgtaa ttcgtcgtac tattaacctc ccgacttaca ctctcgaggc tgtatatgaa     840 gcaattttg gtaagccgaa ggagaaggta tacgccgatg agattgcaaa ggcgtgggaa     900
accggtgagg gcctcgagcg tgttgcaaaa tactccatgg aagatgcaaa ggcgacttat     960
gaactcggca agaattctt cccaatggaa gctcagctct ctcgcctggt ggccaacca    1020 ctgtgggatg tttctcgttc ttccaccggt aacctcgtag agtggtttct cctgcgcaaa    1080
gcgtacgaac gcaacgaact ggctccgaac aagccagatg aacgtgagta tgaacgccgt    1140
ctccgcgagt cttacgctgg tggctttgtt aaagagccag aaagggcct ctgggaaaac    1200 atcgtgtccc tcgattttcg cgctctgtat ccgtctatta tcattaccca caacgtgtct    1260
ccggatactc tcaaccgcga gggctgcaga aactatgatg ttgctccgga agtaggccac    1320
aagttctgca aggacttccc gggctttatt ccgtctctcc tgaaacgtct gctcgatgaa    1380
cgccaaaaga ttaagactaa aatgaaggcg tcccaggatc cgattgaaaa ataatgctc    1440 gactatcgcc aaagagcgat taaaatcctc gcaaactctt attacggcta ttatggctat    1500
gcaaaagcac gctggtactg taaggagtgt gctgagtccg ttactgcttg gggtcgcgaa    1560
tacatcgagt tcgtgtggaa ggagctcgaa gaaaagtttg ctttaaagt tctctacatt    1620 gacactgatg gtctctatgc gactattccg ggtggtaagt ctgaggaaat taagaaaaag    1680
gctctagaat ttgtggatta cattaacgcg aagctcccgg gtctcctgga gctcgaatat    1740
gaaggctttt ataaacgcgg cttcttcgtt accaagaaga aatatgcgct gattgatgaa    1800
gaaggcaaaa ttattactcg tggtctcgag attgtgcgcc gtgattggag cgaaattgcg    1860
aaagaaactc aagctagagt tctcgaggct attctcaaac acggcaacgt tgaagaagct    1920
```

```
gtgagaattg taaaagaagt aacccaaaag ctctctaaat atgaaattcc gccagagaag  1980
ctcgcgattt atgagcagat tactcgcccg ctgcatgagt ataaggcgat tggtccgcac  2040
gtggctgttg caaagagact ggctgctaaa ggcgtgaaaa ttaaaccggg tatggtaatt  2100
ggctacattg tactccgcgg cgatggtccg attagcaacc gtgcaattct agctgaggaa  2160
tacgatccga aaagcacaa gtatgacgca gaatattaca ttgagaacca ggtgctcccg  2220
gcggtactcc gtattctgga gggttttggc taccgtaagg aagacctccg ctggcaaaag  2280
actaaacaga ctggcctcac ttcttggctc aacattaaaa aatcc                  2325
```

<210> SEQ ID NO 2
<211> LENGTH: 775
<212> TYPE: PRT
<213> ORGANISM: Artificial Sequence
<220> FEATURE:
<223> OTHER INFORMATION: Description of Artificial Sequence:full-length
    assembled hybrid polymerase clone Phy1

<400> SEQUENCE: 2

```
Met Ile Leu Asp Ala Asp Tyr Ile Thr Glu Glu Gly Lys Pro Val Ile
 1               5                  10                  15

Arg Leu Phe Lys Lys Glu Asn Gly Glu Phe Lys Ile Glu His Asp Arg
            20                  25                  30

Thr Phe Arg Pro Tyr Ile Tyr Ala Leu Leu Lys Asp Asp Ser Lys Ile
        35                  40                  45

Glu Glu Val Lys Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Ile Ile Arg Glu Lys Asp Pro Asp Ile Ile Ile Thr
        195                 200                 205

Tyr Asn Gly Asp Ser Phe Asp Leu Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285
```

```
Lys Val Tyr Ala Asp Glu Ile Ala Lys Ala Trp Glu Thr Gly Glu Gly
    290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                    325                 330                 335

Val Gly Gln Pro Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
    370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                    405                 410                 415

His Asn Val Ser Pro Asp Thr Leu Asn Arg Glu Gly Cys Arg Asn Tyr
                420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Lys Ile
    450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                    485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Glu Tyr Ile Glu Phe Val Trp Lys Glu
            515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                    565                 570                 575

Glu Leu Glu Tyr Glu Gly Phe Tyr Lys Arg Gly Phe Phe Val Thr Lys
                580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
    610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                    645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Arg Leu Ala
            675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
```

```
                    705                 710                 715                 720
Tyr Asp Pro Arg Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
            740                 745                 750
Lys Glu Asp Leu Arg Trp Gln Lys Thr Lys Gln Thr Gly Leu Thr Ser
        755                 760                 765
Trp Leu Asn Ile Lys Lys Ser
    770                 775

<210> SEQ ID NO 3
<211> LENGTH: 2535
<212> TYPE: DNA
<213> ORGANISM: Artificial Sequence
<220> FEATURE:
<223> OTHER INFORMATION: Description of Artificial Sequence:PhS1, Phy1
      and SSo7d fusion protein

<400> SEQUENCE: 3
atgatcctgg atgctgacta catcactgaa gaaggcaaac cggttatccg tctgttcaaa      60
aaagagaacg gcgaatttaa gattgagcat gatcgcacct ttcgtccata catttacgct     120
ctgctgaaag atgattctaa gattgaggaa gttaaaaaaa tcactgctga gcgccatggc     180
aagattgttc gtatcgttga tgcggaaaag gtagaaaaga aatttctggg cagaccaatc     240
accgtgtgga gactgtattt cgaacatcca caagatgttc gactattcg cgagaaaatt     300 cgcgaacatt ctgcagttgt tgacatcttc gaatacgata ttccatttgc aaagcgttac     360
ctcatcgaca aaggcctgat accaatggag ggcgatgaag aactcaagct cctggcgttc     420
gatatagaaa ccctctatca cgaaggcgaa gagtttggta aggcccaat tataatgatc     480 agctatgcag atgaagaaga agcaaaggtg attacttgga aaaaaataga tctcccatac     540
gttgaggttg tatcttccga gcgcgagatg attaagcgct ttctcaaaat tatccgcgag     600
aaggatccgg acattatcat tacttataac ggcgactctt ttgacctccc atatctggcg     660
aaacgcgcag aaaaactcgg tattaaactg actatcggcc gtgatggttc cgagccgaag     720
atgcagcgta tcggcgatat gaccgctgta gaagttaagg gtcgtatcca tttcgacctg     780
tatcatgtaa ttcgtcgtac tattaacctc ccgacttaca ctctcgaggc tgtatatgaa     840
gcaatttttg gtaagccgaa ggagaaggta tacgccgatg agattgcaaa ggcgtgggaa     900
accggtgagg gcctcgagcg tgttgcaaaa tactccatgg aagatgcaaa ggcgacttat     960
gaactcggca agaattctt cccaatggaa gctcagctct ctcgcctggt tggccaacca    1020
ctgtgggatg tttctcgttc ttccaccggt aacctcgtag agtggtttct cctgcgcaaa    1080
gcgtacgaac gcaacgaact ggctccgaac aagccagatg aacgtgagta tgaacgccgt    1140
ctccgcgagt cttacgctgg tggctttgtt aaagagccag aaaagggcct ctgggaaaac    1200
atcgtgtccc tcgattttcg cgctctgtat ccgtctatta tcattaccca caacgtgtct    1260
ccggatactc tcaaccgcga gggctgcaga aactatgatg ttgctccgga agtaggccac    1320
aagttctgca aggacttccc gggctttatt ccgtctctcc tgaaacgtct gctcgatgaa    1380
cgccaaaaga ttaagactaa aatgaaggcg tcccaggatc cgattgaaaa ataatgctc    1440 gactatcgcc aaagagcgat taaatcctc gcaaactctt attacggcta ttatggctat    1500
gcaaaagcac gctggtactg taaggagtgt gctgagtccg ttactgcttg gggtcgcgaa    1560
tacatcgagt tcgtgtggaa ggagctcgaa gaaaagtttg gctttaaagt tctctacatt    1620
```

-continued

```
gacactgatg gtctctatgc gactattccg ggtggtaagt ctgaggaaat taagaaaaag    1680
gctctagaat ttgtggatta cattaacgcg aagctcccgg gtctcctgga gctcgaatat    1740
gaaggctttt ataaacgcgg cttcttcgtt accaagaaga aatatgcgct gattgatgaa    1800
gaaggcaaaa ttattactcg tggtctcgag attgtgcgcc gtgattggag cgaaattgcg    1860
aaagaaactc aagctagagt tctcgaggct attctcaaac acggcaacgt tgaagaagct    1920
gtgagaattg taaagaagt aacccaaaag ctctctaaat atgaaattcc gccagagaag    1980
ctcgcgattt atgagcagat tactcgcccg ctgcatgagt ataaggcgat tggtccgcac    2040
gtggctgttg caaagagact ggctgctaaa ggcgtgaaaa ttaaaccggg tatggtaatt    2100
ggctacattg tactccgcgg cgatggtccg attagcaacc gtgcaattct agctgaggaa    2160
tacgatccga aaagcacaa gtatgacgca gaatattaca ttgagaacca ggtgctcccg    2220
gcggtactcc gtattctgga gggttttggc taccgtaagg aagacctccg ctggcaaaag    2280
actaaacaga ctggcctcac ttcttggctc aacattaaaa aatccggtac cggcggtggc    2340
ggtgcaaccg taaagttcaa gtacaaaggc gaagaaaaag aggtagacat ctccaagatc    2400
aagaaagtat ggcgtgtggg caagatgatc tccttcacct acgacgaggg cggtggcaag    2460
accggccgtg gtgcggtaag cgaaaaggac gcgccgaagg agctgctgca gatgctggag    2520
aagcagaaaa agtga                                                    2535
```

<210> SEQ ID NO 4
<211> LENGTH: 844
<212> TYPE: PRT
<213> ORGANISM: Artificial Sequence
<220> FEATURE:
<223> OTHER INFORMATION: Description of Artificial Sequence:PhS1, Phy1
      and SSo7d fusion protein

<400> SEQUENCE: 4

```
Met Ile Leu Asp Ala Asp Tyr Ile Thr Glu Glu Gly Lys Pro Val Ile
  1               5                  10                  15

Arg Leu Phe Lys Lys Glu Asn Gly Glu Phe Lys Ile Glu His Asp Arg
             20                  25                  30

Thr Phe Arg Pro Tyr Ile Tyr Ala Leu Leu Lys Asp Asp Ser Lys Ile
         35                  40                  45

Glu Glu Val Lys Lys Ile Thr Ala Glu Arg His Gly Lys Ile Val Arg
     50                  55                  60

Ile Val Asp Ala Glu Lys Val Glu Lys Lys Phe Leu Gly Arg Pro Ile
 65                  70                  75                  80

Thr Val Trp Arg Leu Tyr Phe Glu His Pro Gln Asp Val Pro Thr Ile
                 85                  90                  95

Arg Glu Lys Ile Arg Glu His Ser Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190
```

-continued

```
Arg Phe Leu Lys Ile Ile Arg Glu Lys Asp Pro Asp Ile Ile Ile Thr
            195                 200                 205

Tyr Asn Gly Asp Ser Phe Asp Leu Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
290                 295                 300

Leu Glu Arg Val Ala Lys Tyr Ser Met Glu Asp Ala Lys Ala Thr Tyr
305                 310                 315                 320

Glu Leu Gly Lys Glu Phe Pro Met Glu Ala Gln Leu Ser Arg Leu
                325                 330                 335

Val Gly Gln Pro Leu Trp Asp Val Ser Arg Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Lys Ile
    450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
```

```
                610             615             620
Ala Arg Val Leu Glu Ala Ile Leu Lys His Gly Asn Val Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Arg Leu Ala
            675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
                740                 745                 750

Lys Glu Asp Leu Arg Trp Gln Lys Thr Lys Gln Thr Gly Leu Thr Ser
            755                 760                 765

Trp Leu Asn Ile Lys Lys Ser Gly Thr Gly Gly Gly Gly Ala Thr Val
770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
                820                 825                 830

Lys Glu Leu Leu Gln Met Leu Glu Lys Gln Lys Lys
            835                 840

<210> SEQ ID NO 5
<211> LENGTH: 2535
<212> TYPE: DNA
<213> ORGANISM: Artificial Sequence
<220> FEATURE:
<223> OTHER INFORMATION: Description of Artificial Sequence:hybrid
      polymerase Sso7d fusion protein PhS2

<400> SEQUENCE: 5
atgatcctgg atgttgacta catcactgaa gaaggcaaac cggttatccg tctgttcaaa        60
aaagagaacg gcgaatttaa ggttgagtat gatcgcacct ttcgtccata catttacgct       120
ctgctgaaag atgattctaa gattgatgaa gttagaaaaa tcactggtga gcgccatggc       180
aagattgttc gtatcattga tgcggaaaag gtacgtaaga aatttctggg caaaccaatc       240
gaggtgtgga actgtatttt cgaacatcca caagatgttc gactattcg cgagaaaatt       300 cgcgaacatt ctgcagttgt tgacatcttc gaatacgata ttccatttgc aaagcgttac       360
ctcatcgaca aggcctgat accaatggag ggcgaggaag aactcaagat cctggcgttc       420
gatatagaaa ccctctatca cgaaggcgaa gagtttggta aggcccaat tataatgatc       480 agctatgcag atgaaaacga agcaaaggta attacttgga aaaaataga ctcccatac       540 gttgaggttg tatcttccga gcgcgagatg attaagcgct ttctcaaagt tatccgcgag       600
aaggatccgg acattatcgt tactataac ggcgactctt ttgacttccc atatctggcg       660
aaacgcgcag aaaaactcgg tattaaactg cctatcggcc gtgatggttc cgagccgaag       720
```

| | |
|---|---|
| atgcagcgta tcggcgatat gaccgctgta gaagttaagg gtcgtatcca tttcgacctg | 780 |
| tatcatgtaa ttcgtcgtac tattaacctc ccgacttaca ctctcgaggc tgtatatgaa | 840 |
| gcaattttg gtaagccgaa ggagaaggta tacgcccatg agattgcaga ggcgtgggaa | 900 |
| tccggtgagg gcctcgagcg tgttgcaaaa tactccatgg aagatgcaaa ggcgacttat | 960 |
| gaactcggca agaattctt cccaatggaa atccagctct ctcgcctggt tggccaacca | 1020 |
| ctgtgggatg tttctcgttc ttccaccggt aacctcgtag agtggtttct cctgcgcaaa | 1080 |
| gcgtacgaac gcaacgaact ggctccgaac aagccatctg aacgtgagta tgaacgccgt | 1140 |
| ctccgcgagt cttacactgg tggctatgtt aaagagccag aaaagggcct ctgggaaaac | 1200 |
| atcgtgtacc tcgattttcg ctctctgtat ccgtctatta tcattaccca caacgtgtct | 1260 |
| ccggatactc tcaacctcga gggctgcaaa gagtatgatg ttgctccgga agtaggccac | 1320 |
| aagttctgca aggacatccc gggctttatt ccgtctctcc tgggccatct gctcgaggaa | 1380 |
| cgccaaaaga ttaagcgtaa aatgaaggcg tccaaggatc cgattgaaaa aatactgctc | 1440 |
| gactatcgcc aaagagcgat taaactcctc gcaaactctt tttacggcta ttatggctat | 1500 |
| gcaaaagcac gctggtactg taaggagtgt gctgagtccg ttactgcttg gggtcgcgaa | 1560 |
| tacatcgagc tcgtgcggaa ggagctcgaa gaaaagtttg ctttaaagt tctctacatt | 1620 |
| gacactgatg gtctctatgc gactattccg ggtggtaagt ctgaggaaat taagaaaaag | 1680 |
| gctctagaat ttgtggatta cattaactcg aagctcccgg gtctcctgga gctcgaatat | 1740 |
| gaaggctttt ataaacgcgg cttcttcgtt accaagaaga gatatgcgct gattgatgaa | 1800 |
| gaaggcaaaa ttattactcg tggtctcgag attgtgcgcc gtgattggag cgaaattgcg | 1860 |
| aaagaaactc aagctaaagt tctcgagact attctcaaac acggcaacgt tgaagaagct | 1920 |
| gtgagaattg taaagaagt aacccaaaag ctcgctaaat atgaaattcc accagagaag | 1980 |
| ctcgcgattt atgagcagat tactccccc ctgcatgagt ataaggcgat tggtccccac | 2040 |
| gtggctgttg caaagagact ggctgctaga ggcgtgaaaa ttaaaccggg tatggtaata | 2100 |
| ggctacattg tactccgcgg cgatggtccg attagcaacc gtgcaattct agctgaggaa | 2160 |
| tacgatctga aaaagcacaa gtatgacgca gaatattaca ttgagaacca ggtgctcccg | 2220 |
| gcggtactcc gtattctgga ggcttttggc taccgtaagg aagacctccg ctaccaaaag | 2280 |
| actaaacagg ttgacctcac tgcttgcctc aacattaaaa aatccggtac cggcggtggc | 2340 |
| ggtgcaaccg taaagttcaa gtacaaaggc gaagaaaaag aggtagacat ctccaagatc | 2400 |
| aagaaagtat ggcgtgtggg caagatgatc tccttcacct acgacgaggg cggtggcaag | 2460 |
| accggccgtg gtgcggtaag cgaaaaggac gctccgaagg agctcctgca gatgctggag | 2520 |
| aagcagaaaa agtga | 2535 |

<210> SEQ ID NO 6
<211> LENGTH: 844
<212> TYPE: PRT
<213> ORGANISM: Artificial Sequence
<220> FEATURE:
<223> OTHER INFORMATION: Description of Artificial Sequence:hybrid
   polymerase Sso7d fusion protein PhS2

<400> SEQUENCE: 6

Met Ile Leu Asp Val Asp Tyr Ile Thr Glu Glu Gly Lys Pro Val Ile
 1               5                  10                  15

Arg Leu Phe Lys Lys Glu Asn Gly Glu Phe Lys Val Glu Tyr Asp Arg
            20                  25                  30

```
Thr Phe Arg Pro Tyr Ile Tyr Ala Leu Leu Lys Asp Asp Ser Lys Ile
        35                  40                  45

Asp Glu Val Arg Lys Ile Thr Gly Glu Arg His Gly Lys Ile Val Arg
    50                  55                  60

Ile Ile Asp Ala Glu Lys Val Arg Lys Lys Phe Leu Gly Lys Pro Ile
65                  70                  75                  80

Glu Val Trp Lys Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Lys Ile
                165                 170                 175

Asp Leu Pro Tyr Val Glu Val Val Ser Ser Glu Arg Glu Met Ile Lys
                180                 185                 190

Arg Phe Leu Lys Val Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
210                 215                 220

Lys Leu Gly Ile Lys Leu Pro Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
    275                 280                 285

Lys Val Tyr Ala His Glu Ile Ala Glu Ala Trp Glu Ser Gly Glu Gly
    290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ile Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Lys Pro Ser Glu Arg Glu Tyr Glu Arg Arg Leu Arg Glu Ser
    370                 375                 380

Tyr Thr Gly Gly Tyr Val Lys Glu Pro Glu Lys Gly Leu Trp Glu Asn
385                 390                 395                 400

Ile Val Tyr Leu Asp Phe Arg Ser Leu Tyr Pro Ser Ile Ile Ile Thr
                405                 410                 415

His Asn Val Ser Pro Asp Thr Leu Asn Leu Glu Gly Cys Lys Glu Tyr
                420                 425                 430

Asp Val Ala Pro Glu Val Gly His Lys Phe Cys Lys Asp Ile Pro Gly
            435                 440                 445

Phe Ile Pro Ser Leu Leu Gly His Leu Leu Glu Glu Arg Gln Lys Ile
```

```
                450                 455                 460
Lys Arg Lys Met Lys Ala Ser Lys Asp Pro Ile Glu Lys Ile Leu Leu
465                 470                 475                 480

Asp Tyr Arg Gln Arg Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Glu Tyr Ile Glu Leu Val Arg Lys Glu
                515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
                580                 585                 590

Lys Arg Tyr Ala Leu Ile Asp Glu Glu Gly Lys Ile Ile Thr Arg Gly
                595                 600                 605

Leu Glu Ile Val Arg Arg Asp Trp Ser Glu Ile Ala Lys Glu Thr Gln
610                 615                 620

Ala Lys Val Leu Glu Thr Ile Leu Lys His Gly Asn Val Glu Glu Ala
625                 630                 635                 640

Val Arg Ile Val Lys Glu Val Thr Gln Lys Leu Ala Lys Tyr Glu Ile
                645                 650                 655

Pro Pro Glu Lys Leu Ala Ile Tyr Glu Gln Ile Thr Pro Pro Leu His
                660                 665                 670

Glu Tyr Lys Ala Ile Gly Pro His Val Ala Val Ala Lys Arg Leu Ala
                675                 680                 685

Ala Arg Gly Val Lys Ile Lys Pro Gly Met Val Ile Gly Tyr Ile Val
                690                 695                 700

Leu Arg Gly Asp Gly Pro Ile Ser Asn Arg Ala Ile Leu Ala Glu Glu
705                 710                 715                 720

Tyr Asp Leu Lys Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
                740                 745                 750

Lys Glu Asp Leu Arg Tyr Gln Lys Thr Lys Gln Val Asp Leu Thr Ala
                755                 760                 765

Cys Leu Asn Ile Lys Lys Ser Gly Thr Gly Gly Gly Ala Thr Val
770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
                820                 825                 830

Lys Glu Leu Leu Gln Met Leu Glu Lys Gln Lys Lys
        835                 840

<210> SEQ ID NO 7
<211> LENGTH: 2535
<212> TYPE: DNA
<213> ORGANISM: Artificial Sequence
```

<220> FEATURE:
<223> OTHER INFORMATION: Description of Artificial Sequence:hybrid
    polymerase Sso7d fusion protein PhS5

<400> SEQUENCE: 7

| | | | | | |
|---|---|---|---|---|---|
| atgatcctgg | atgctgacta | catcactgaa | gacggcaaac | cgattatccg | tctgttcaaa | 60 |
| aaagagaacg | gcgaatttaa | ggttgagtat | gatcgcaact | ttcgtccata | catttacgct | 120 |
| ctgctgagag | atgattctca | gattgatgaa | gttaaaaaaa | tcactgctga | gcgccatggc | 180 |
| aagattgttc | gtatcattga | tgcggaaaag | gtagaaaaga | aatttctggg | cagaccaatc | 240 |
| accgtgtgga | gactgtattt | cgaacatcca | caagatgttc | cggctattcg | cgataaagtt | 300 |
| cgcgaacatc | ctgcagttgt | tgacatcttc | gaatacgata | ttccatttgc | aaagcgttac | 360 |
| ctcatcgaca | aggcctgat | accaatggag | ggcgaggaag | aactcaagct | cctggcgttc | 420 |
| gatatagaaa | ccctctatca | cgaaggcgaa | gagtttggta | aggcccaat | tataatgatc | 480 |
| agctatgcag | atgaaaacga | agcaaggtg | attacttgga | aaaaaataga | tctcccatac | 540 |
| gttgaggttg | tatcttccga | gcgcgagatg | attaaacgtt | ttctcagagt | tatccgcgag | 600 |
| aaggatccgg | acattatcat | tacttataac | ggcgactctt | ttgacttccc | atatctggcg | 660 |
| aaacgcgcag | aaaaactcgg | tattaaactg | cctctcggcc | gtgatggttc | cgagccgaag | 720 |
| atgcagcgta | tcggcgatat | gaccgctgta | gaaattaagg | gtcgtatcca | tttcgacctg | 780 |
| tatcatgtaa | ttactcgtac | tattaacctc | ccgacttaca | ctctcgaggc | tgtatatgaa | 840 |
| gcaatttttg | gtaagccgaa | ggagaaggta | tacgccgatg | agattgcaga | ggcgtgggaa | 900 |
| tccggtaaga | acctcgagcg | tgttgcaaaa | tactccatgg | aagatgcaaa | ggcgacttat | 960 |
| gaactcggca | agaattcct | cccaatggaa | atccagctct | ctcgcctggt | tggccaacca | 1020 |
| ctgtgggatg | tttctcgttc | ttccaccggt | aacctcgtag | agtggtatct | cctgcgcaaa | 1080 |
| gcgtacgaac | gcaacgaagt | ggctccgaac | aagccagacg | aagaagagta | tgaacgccgt | 1140 |
| ctccgcgagt | cttacactgg | tggctatgtt | aaagagccag | aaaagggcct | ctgggaaaac | 1200 |
| ctcgtgtccc | tcgattttcg | cgctctgtat | ccgtctatta | tcattaccca | caacgtgtct | 1260 |
| ccggatactc | tcaaccgcga | gggctgcaaa | gagtatgata | ttgctccgca | agtaggccac | 1320 |
| aagttctgca | aggacttccc | gggctttatt | ccgtctctcc | tgaaacatct | gctcgatgaa | 1380 |
| cgccaagaga | ttaagcgtaa | atgaaggcg | tccaaggatc | cgattgaaaa | aaaaatgctc | 1440 |
| gactatcgcc | aaagagcgat | taaactcctc | gcaaactctt | tttacggcta | ttatggctat | 1500 |
| gcaaaagcac | gctggtactg | taaggagtgt | gctgagtccg | ttactgcttg | gggtcgcgaa | 1560 |
| tacatcgagc | tcgtgtggaa | ggagctcgaa | gaaaagtttg | gctttaaagt | tctctacatt | 1620 |
| gacactgatg | gtctctatgc | gactattccg | ggtggtaagc | ctgaggaaat | taagaaaaag | 1680 |
| gctctagaat | ttgtgaaata | cattaactcg | aagctcccgg | gtctcctgga | gctcgaatat | 1740 |
| gaaggctttt | atgttcgcgg | cttcttcgtt | accaagaaga | gatatgcggt | gattgatgaa | 1800 |
| gaaggcaaaa | ttattactcg | tggtctcgag | attgtgcgcc | gtgattggag | cgaaattgcg | 1860 |
| aaagaaactc | aagctagagt | tctcgaggct | attctcaaac | acggcaacgt | tgaagaagct | 1920 |
| gtgaaaattg | taaagaagt | aacccaaaag | ctcgctaaat | atgaaattcc | gccagagaag | 1980 |
| ctcgcgattt | atgagcagat | tactcgcccg | ctgcatgagt | ataaggcgat | tggtccgcac | 2040 |
| gtggctgttg | caagagact | ggctgctaga | ggcgtgaaag | ttagaccggg | tatggtaatt | 2100 |
| ggctacattg | tactccgcgg | cgatggtccg | attagcaacc | gtgcaattct | agctgaggaa | 2160 |
| tacgatctga | aaaagcacaa | gtatgacgca | gaatattaca | ttgagaacca | ggtgctcccg | 2220 |

```
gcggtactcc gtattctgga ggcttttggc taccgtaagg aagacctccg ctggcaaaag    2280
actaaacagg ttggcctcac ttcttggctc aacattaaaa aatccggtac cggcggtggc    2340
ggtgcaaccg taaagttcaa gtacaaaggc gaagaaaaag aggtagacat ctccaagatc    2400
aagaaagtat ggcgtgtggg caagatgatc tccttcacct acgacgaggg cggtggcaag    2460
accggccgtg gtgcggtaag cgaaaaggac gcgccgaagg agctgctgca gatgctggag    2520
aagcagaaaa agtga                                                     2535
```

<210> SEQ ID NO 8
<211> LENGTH: 844
<212> TYPE: PRT
<213> ORGANISM: Artificial Sequence
<220> FEATURE:
<223> OTHER INFORMATION: Description of Artificial Sequence:hybrid
      polymerase Sso7d fusion protein PhS5

<400> SEQUENCE: 8

```
Met Ile Leu Asp Ala Asp Tyr Ile Thr Glu Asp Gly Lys Pro Ile Ile
1               5                   10                  15

Arg Leu Phe Lys Lys Glu Asn Gly Glu Phe Lys Val Glu Tyr Asp Arg
            20                  25                  30

Asn Phe Arg Pro Tyr Ile Tyr Ala Leu Leu Arg Asp Asp Ser Gln Ile
        35                  40                  45

Asp Glu Val Lys Lys Ile Thr Ala Glu Arg His Gly Lys Ile Val Arg
    50                  55                  60

Ile Ile Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Ala Ile
                85                  90                  95

Arg Asp Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Leu Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Arg Val Ile Arg Glu Lys Asp Pro Asp Ile Ile Ile Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Ile Gly Asp Met Thr Ala Val Glu Ile Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Glu Ala Trp Glu Ser Gly Lys Asn
```

-continued

```
            290                 295                 300
Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Thr Gly Asn Leu
                340                 345                 350

Val Glu Trp Tyr Leu Leu Arg Lys Ala Tyr Glu Arg Asn Glu Val Ala
                355                 360                 365

Pro Asn Lys Pro Asp Glu Glu Tyr Glu Arg Arg Leu Arg Glu Ser
370                 375                 380

Tyr Thr Gly Gly Tyr Val Lys Glu Pro Glu Lys Gly Leu Trp Glu Asn
385                 390                 395                 400

Leu Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Lys Glu Tyr
                420                 425                 430

Asp Ile Ala Pro Gln Val Gly His Lys Phe Cys Lys Asp Phe Pro Gly
                435                 440                 445

Phe Ile Pro Ser Leu Leu Lys His Leu Leu Asp Glu Arg Gln Glu Ile
        450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Glu Tyr Ile Glu Leu Val Trp Lys Glu
                515                 520                 525

Leu Glu Glu Lys Phe Gly Phe Lys Val Leu Tyr Ile Asp Thr Asp Gly
                530                 535                 540

Leu Tyr Ala Thr Ile Pro Gly Gly Lys Pro Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Val Arg Gly Phe Phe Val Thr Lys
                580                 585                 590

Lys Arg Tyr Ala Val Ile Asp Glu Glu Gly Lys Ile Ile Thr Arg Gly
                595                 600                 605

Leu Glu Ile Val Arg Arg Asp Trp Ser Glu Ile Ala Lys Glu Thr Gln
610                 615                 620

Ala Arg Val Leu Glu Ala Ile Leu Lys His Gly Asn Val Glu Glu Ala
625                 630                 635                 640

Val Lys Ile Val Lys Glu Val Thr Gln Lys Leu Ala Lys Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Arg Leu Ala
                675                 680                 685

Ala Arg Gly Val Lys Val Arg Pro Gly Met Val Ile Gly Tyr Ile Val
                690                 695                 700

Leu Arg Gly Asp Gly Pro Ile Ser Asn Arg Ala Ile Leu Ala Glu Glu
705                 710                 715                 720
```

Tyr Asp Leu Lys Lys His Lys Tyr Asp Ala Glu Tyr Tyr Ile Glu Asn
            725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Val Gly Leu Thr Ser
            755                 760                 765

Trp Leu Asn Ile Lys Lys Ser Gly Thr Gly Gly Gly Gly Ala Thr Val
            770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
            805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys
            835                 840

<210> SEQ ID NO 9
<211> LENGTH: 2535
<212> TYPE: DNA
<213> ORGANISM: Artificial Sequence
<220> FEATURE:
<223> OTHER INFORMATION: Description of Artificial Sequence:hybrid
      polymerase Sso7d fusion protein PhS7

<400> SEQUENCE: 9

| | |
|---|---:|
| atgatcctgg atgctgacta catcactgaa gacggcaaac cgattatccg tctgttcaaa | 60 |
| aaagagaacg gcgaatttaa ggttgagtat gatcgcaact tcgtccata catttacgct | 120 |
| ctgctgagag atgattctca gattgatgaa gttaaaaaaa tcactgctga gcgccatggc | 180 |
| aagattgttc gtatcattga tgcggaaaag gtagaaaaga aatttctggg cagaccaatc | 240 |
| accgtgtgga gactgtattt cgaacatcca caagatgttc ggctattcg cgataaagtt | 300 |
| cgcgaacatc ctgcagttgt tgacatcttc gaatacgata ttccatttgc aaagcgttac | 360 |
| ctcatcgaca aaggcctgat accaatggag ggcgaggaag aactcaagct cctggcgttc | 420 |
| gatatagaaa ccctctatca cgaaggcgaa gagtttggta aagcccaat tataatgatc | 480 |
| agctatgcag atgaaaacga agcaaggtg attacttgga aaaaaataga tctcccatac | 540 |
| gttgaggttg tatcttccga cgcgagatg attaaacgtt ttctcagagt tatccgcgag | 600 |
| aaggatccgg acattatcat tacttataac ggcgactctt ttgacttccc atatctggcg | 660 |
| aaacgcgcag aaaaactcgg tattaaactg cctctcggcc gtgatggttc cgagccgaag | 720 |
| atgcagcgta tcggcgatat gaccgctgta gaaattaagg tcgtatcca tttcgacctg | 780 |
| tatcatgtaa ttactcgtac tattaacctc ccgacttaca ctctcgaggc tgtatatgaa | 840 |
| gcaattttg gtaagccgaa ggagaaggta tacgccgatg agattgcaga ggcgtgggaa | 900 |
| tccggtaaga acctcgagcg tgttgcaaaa tactccatgg aagatgcaaa ggcgacttat | 960 |
| gaactcggca agaattcct cccaatggaa atccagctct tcgcctggt ggccaacca | 1020 |
| ctgtgggatg tttctcgttc ttccaccggt aacctcgtag agtggtatct cctgcgcaaa | 1080 |
| gcgtacgaac gcaacgaagt ggctccgaac aagccagacg aagaagagta tgaacgccgt | 1140 |
| ctccgcgagt cttacactgg tggctatgtt aaagagccag aaagggcct ctgggaaaac | 1200 |
| ctcgtgtccc tcgattttcg cgctctgtat ccgtctatta tcattaccca caacgtgtct | 1260 |
| ccggatactc tcaaccgcga gggctgcaga aactatgatg ttgctccgca agtaggccac | 1320 |

-continued

```
aagttctgca aggacttccc gggctttatt ccgtctctcc tgggccgtct gctcgaggaa   1380
cgccaagaga ttaagactaa aatgaaggcg accaaggatc cgattgaaaa aaaactgctc   1440
gactatcgcc aaaaagcgat taaaatcctc gcaaactctt tttacggcta ttatggctat   1500
gcaaaagcac gctggtactg taaggagtgt gctgagtccg ttactgcttg ggtcgcaaa    1560
tacatcgagt tcgtgcggaa ggagctcgaa gaaaagtttg ctttaaagt tctctacatt    1620
gacactgatg gtctctatgc gactattccg ggtggtaagc ctgaggaaat taagaaaaag   1680
gctctagaat ttgtgaaata cattaactcg aagctcccgg gtctcctgga gctcgaatat   1740
gaaggctttt atgttcgcgg cttcttcgtt accaagaaga gatatgcggt gattgatgaa   1800
gaaggcaaaa ttattactcg tggtctcgag attgtgcgcc gtgattggag cgaaattgcg   1860
aaagaaactc aagctagagt tctcgaggct attctcaaac acggcaacgt tgaagaagct   1920
gtgaaaattg taaagaagt aacccaaaag ctcgctaaat atgaaattcc gccagagaag   1980
ctcgcgattt atgagcagat tactcgcccg ctgcatgagt ataaggcgat tggtccgcac   2040
gtggctgttg caagagagact ggctgctaga ggcgtgaaag ttagaccggg tatggtaatt   2100
ggctacattg tactccgcgg cgatggtccg attagcaacc gtgcaattct agctgaggaa   2160
tacgatctga aaaagcacaa gtatgacgca gaatattaca ttgagaacca ggtgctcccg   2220
gcggtactcc gtattctgga ggcttttggc taccgtaagg aagacctccg ctggcaaaag   2280
actaaacagg ttggcctcac ttcttggctc aacattaaaa aatccggtac cggcggtggc   2340
ggtgcaaccg taagttcaa gtacaaaggc gaagaaaaag aggtagacat ctccaagatc   2400
aagaaagtat ggcgtgtggg caagatgatc tccttcacct acgacgaggg cggtggcaag   2460
accggccgtg gtgcggtaag cgaaaaggac gcgccgaagg agctgctgca gatgctggag   2520
aagcagaaaa agtga                                                    2535
```

<210> SEQ ID NO 10
<211> LENGTH: 844
<212> TYPE: PRT
<213> ORGANISM: Artificial Sequence
<220> FEATURE:
<223> OTHER INFORMATION: Description of Artificial Sequence:hybrid
      polymerase Sso7d fusion protein PhS7

<400> SEQUENCE: 10

```
Met Ile Leu Asp Ala Asp Tyr Ile Thr Glu Asp Gly Lys Pro Ile Ile
  1               5                  10                  15

Arg Leu Phe Lys Lys Glu Asn Gly Glu Phe Lys Val Glu Tyr Asp Arg
             20                  25                  30

Asn Phe Arg Pro Tyr Ile Tyr Ala Leu Leu Arg Asp Asp Ser Gln Ile
         35                  40                  45

Asp Glu Val Lys Lys Ile Thr Ala Glu Arg His Gly Lys Ile Val Arg
     50                  55                  60

Ile Ile Asp Ala Glu Lys Val Glu Lys Lys Phe Leu Gly Arg Pro Ile
 65                  70                  75                  80

Thr Val Trp Arg Leu Tyr Phe Glu His Pro Gln Asp Val Pro Ala Ile
                 85                  90                  95

Arg Asp Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Leu Leu Ala Phe Asp Ile Glu Thr
```

-continued

```
            130                 135                 140
Leu Tyr His Glu Gly Glu Phe Gly Lys Gly Pro Ile Ile Met Ile
145                 150                 155                 160

Ser Tyr Ala Asp Glu Asn Glu Ala Lys Val Ile Thr Trp Lys Ile
                165                 170                 175

Asp Leu Pro Tyr Val Glu Val Val Ser Ser Glu Arg Glu Met Ile Lys
            180                 185                 190

Arg Phe Leu Arg Val Ile Arg Glu Lys Asp Pro Asp Ile Ile Thr
            195                 200                 205

Tyr Asn Gly Asp Ser Phe Asp Phe Pro Tyr Leu Ala Lys Arg Ala Glu
210                 215                 220

Lys Leu Gly Ile Lys Leu Pro Leu Gly Arg Asp Gly Ser Glu Pro Lys
225                 230                 235                 240

Met Gln Arg Ile Gly Asp Met Thr Ala Val Glu Ile Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
            275                 280                 285

Lys Val Tyr Ala Asp Glu Ile Ala Glu Ala Trp Glu Ser Gly Lys Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Val Ala
            355                 360                 365

Pro Asn Lys Pro Asp Glu Glu Tyr Glu Arg Arg Leu Arg Glu Ser
370                 375                 380

Tyr Thr Gly Gly Tyr Val Lys Glu Pro Glu Lys Gly Leu Trp Glu Asn
385                 390                 395                 400

Leu Val Ser Leu Asp Phe Arg Ala Leu Tyr Pro Ser Ile Ile Thr
                405                 410                 415

His Asn Val Ser Pro Asp Thr Leu Asn Arg Glu Gly Cys Arg Asn Tyr
            420                 425                 430

Asp Val Ala Pro Gln Val Gly His Lys Phe Cys Lys Asp Phe Pro Gly
            435                 440                 445

Phe Ile Pro Ser Leu Leu Gly Arg Leu Leu Glu Glu Arg Gln Glu Ile
450                 455                 460

Lys Thr Lys Met Lys Ala Thr Lys Asp Pro Ile Glu Lys Lys Leu Leu
465                 470                 475                 480

Asp Tyr Arg Gln Lys Ala Ile Lys Ile Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Phe Val Arg Lys Glu
            515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Lys Pro Glu Glu Ile Lys Lys Lys
545                 550                 555                 560
```

```
Ala Leu Glu Phe Val Lys Tyr Ile Asn Ser Lys Leu Pro Gly Leu Leu
            565                 570                 575
Glu Leu Glu Tyr Glu Gly Phe Tyr Val Arg Gly Phe Phe Val Thr Lys
        580                 585                 590
Lys Arg Tyr Ala Val Ile Asp Glu Glu Gly Lys Ile Ile Thr Arg Gly
    595                 600                 605
Leu Glu Ile Val Arg Arg Asp Trp Ser Glu Ile Ala Lys Glu Thr Gln
610                 615                 620
Ala Arg Val Leu Glu Ala Ile Leu Lys His Gly Asn Val Glu Ala
625                 630                 635                 640
Val Lys Ile Val Lys Glu Val Thr Gln Lys Leu Ala Lys Tyr Glu Ile
                645                 650                 655
Pro Pro Glu Lys Leu Ala Ile Tyr Glu Gln Ile Thr Arg Pro Leu His
            660                 665                 670
Glu Tyr Lys Ala Ile Gly Pro His Val Ala Val Ala Lys Arg Leu Ala
        675                 680                 685
Ala Arg Gly Val Lys Val Arg Pro Gly Met Val Ile Gly Tyr Ile Val
690                 695                 700
Leu Arg Gly Asp Gly Pro Ile Ser Asn Arg Ala Ile Leu Ala Glu Glu
705                 710                 715                 720
Tyr Asp Leu Lys Lys His Lys Tyr Asp Ala Glu Tyr Tyr Ile Glu Asn
                725                 730                 735
Gln Val Leu Pro Ala Val Leu Arg Ile Leu Glu Ala Phe Gly Tyr Arg
            740                 745                 750
Lys Glu Asp Leu Arg Trp Gln Lys Thr Lys Gln Val Gly Leu Thr Ser
        755                 760                 765
Trp Leu Asn Ile Lys Lys Ser Gly Thr Gly Gly Gly Gly Ala Thr Val
770                 775                 780
Lys Phe Lys Tyr Lys Gly Glu Glu Lys Glu Val Asp Ile Ser Lys Ile
785                 790                 795                 800
Lys Lys Val Trp Arg Val Gly Lys Met Ile Ser Phe Thr Tyr Asp Glu
                805                 810                 815
Gly Gly Gly Lys Thr Gly Arg Gly Ala Val Ser Glu Lys Asp Ala Pro
            820                 825                 830
Lys Glu Leu Leu Gln Met Leu Glu Lys Gln Lys Lys
        835                 840

<210> SEQ ID NO 11
<211> LENGTH: 2337
<212> TYPE: DNA
<213> ORGANISM: Artificial Sequence
<220> FEATURE:
<223> OTHER INFORMATION: Description of Artificial Sequence:hybrid
      polymerase Hyb1
<220> FEATURE:
<221> NAME/KEY: modified_base
<222> LOCATION: (1416)
<223> OTHER INFORMATION: n = g, a, c or t

<400> SEQUENCE: 11
atgatcctgg atgctgacta catcactgaa gacggcaaac cggttatccg tctcttcaaa      60
aaagagaacg gcgaatttaa gattgagtat gatcgcacct ttcgtccata catttacgct    120
ctgctgagag atgattctaa gattgaggaa gttagaaaaa tcactgctga gcgccatggc    180
aagattgttc gtatcgttga tgtggaaaag gtaaggaaga aatttctggg cagaccaatc    240
aaggtgtgga gactgtattt cgaacatcca caagatgttc gactattcg cgataaagtt    300
```

```
cgcgaacatc ctgcagttat tgacatcttc gaatacgata ttgcatttgc aaagcgttac      360
ctcatcgaca aaggcctgat accaatggag ggcgaggaag aactcaagat cctggcgttc      420
gatatagaaa ccctctatca cggaagcgaa gagtttggta aaggcccaat tataatgatc      480
agctatgcag atgaaaacga agcaaaggtg attacttgga aaaacataga tctcccatac      540
gttgaggttg tatcttccga gcgcgagatg attaaacgct ttctcagaat tatccgcgag      600
aaggatccgg acattatcgt tacttataac ggcgactctt ttgacctccc atatctggcg      660
aaacgcgcag aaaaactcgg tattaaactg actctcggcc gtgatggttg cgaggcgaag      720
atgcagcgtc tcggcgatat gaccgctgta gaagttaagg gtcgtatcca tttcgacctg      780
tattatgtaa ttagccgtac tattaacctc ccgacttaca ctctcgaggc tgtatatgaa      840 gcaattttg gtaagccgaa ggagaaggta tacgccgatg atattgcaga ggcgtgggaa      900
accggtaagg gcctcgagcg tgttgcaaaa tactccatgg aagatgcaaa ggcgacttat      960
gaactcggca agaattcct cccaatggaa gctcagctct ctcgcctggt tggccaacca     1020
ctgtgggatg tttctcgttc ttccaccggt aacctcgtag agtggtatct cctgcgcaaa     1080
gcgtacgaac gcaacgaagt ggctccgaac aagccatacg aacgagagta tgaacgccgt     1140
ctccgcgagt cttacactgg tggctttgtt aaagagccag aaaagggcct ctgggaaagc     1200
ctcgtgtccc tcgattttcg ctctctgtat ccgtctatta tcattaccca caacgtgtct     1260
ccggatactc tcaaccgcga gggctgcaaa gactatgata ttgctccgga agtaggccac     1320
aagttctgca aggacttcct tggctttatt ccgtctctcc tggggcatct gctcgaggaa     1380
cgccaagaga ttaagaccaa aatgaaggag acccangatc cgattgaaaa aatactgctc     1440
gactatcgcc aaaaagcgat taaactcctc gcaaactctt attacggcta ttatggctat     1500
gcaaaagcac gctggtactg taaggagtgt gctgagtccg ttactgcttg gggtcgcgaa     1560
tacatcgagt tcgtgtggaa ggagctcgaa gaaaagtttg gctttaaagt tctctacatt     1620
gacactgatg gtctctatgc gactattccg ggtggtgagc ctgaggaaat taagaaaaag     1680
gctctagaat ttgtgaaata cattaactcg aagctccccg gtctcttgga gctcgaatat     1740
gaaggctttt ataagcgcgg cttcttcgtt accaagaaga gatatgcggt gattgatgaa     1800
gaaggcaaaa ttattactcg tggtctcgag attgtgcgcc gtgattggag cgaaattgcg     1860
aaagaaactc aagctaaagt tctcgaggct attctcaaac acggcaacgt tgaagaagct     1920
gtgaaaattg taaagaaat aatcgaaaag ctcgctaaat atgaaatacc gccagagaag     1980
ctcgcgattt atgagcagat tactcgcccg ctgcatgagt ataaggcgat tggtccgcac     2040
gtggctgttg caaagaaact ggctgctaga ggcgtgaaaa ttaaaccggg tatggtaatt     2100
ggctacattg tactccgcgg cgatggtccg attagcaaac gtgcaattct agctgaggaa     2160
ttcgatccga aaagcacaa gtatgacgca gaatattaca ttgagaacca ggtgctcccg     2220
gcggtactcc gtattctgga gggttttggc taccgtaagg aagacctccg ttggcaaaag     2280
actaaacagg ctggcctcac tgcttggctc aacattaaaa aatccggtac ccactag       2337
```

<210> SEQ ID NO 12
<211> LENGTH: 775
<212> TYPE: PRT
<213> ORGANISM: Artificial Sequence
<220> FEATURE:
<223> OTHER INFORMATION: Description of Artificial Sequence:hybrid
      polymerase Hyb1
<220> FEATURE:
<221> NAME/KEY: MOD_RES

```
<222> LOCATION: (472)
<223> OTHER INFORMATION: Xaa = unknown amino acid

<400> SEQUENCE: 12

Met Ile Leu Asp Ala Asp Tyr Ile Thr Glu Asp Gly Lys Pro Val Ile
1               5                   10                  15

Arg Leu Phe Lys Lys Glu Asn Gly Glu Phe Lys Ile Glu Tyr Asp Arg
            20                  25                  30

Thr Phe Arg Pro Tyr Ile Tyr Ala Leu Leu Arg Asp Asp Ser Lys Ile
        35                  40                  45

Glu Glu Val Arg Lys Ile Thr Ala Glu Arg His Gly Lys Ile Val Arg
    50                  55                  60

Ile Val Asp Val Glu Lys Val Arg Lys Phe Leu Gly Arg Pro Ile
65                  70                  75                  80

Lys Val Trp Arg Leu Tyr Phe Glu His Pro Gln Asp Val Pro Thr Ile
                85                  90                  95

Arg Asp Lys Val Arg Glu His Pro Ala Val Ile Asp Ile Phe Glu Tyr
            100                 105                 110

Asp Ile Ala Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
130                 135                 140

Leu Tyr His Gly Ser Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Leu Pro Tyr Leu Ala Lys Arg Ala Glu
210                 215                 220

Lys Leu Gly Ile Lys Leu Thr Leu Gly Arg Asp Gly Cys Glu Ala Lys
225                 230                 235                 240

Met Gln Arg Leu Gly Asp Met Thr Ala Val Glu Val Lys Gly Arg Ile
                245                 250                 255

His Phe Asp Leu Tyr Tyr Val Ile Ser Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Asp Ile Ala Glu Ala Trp Glu Thr Gly Lys Gly
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Val Ala
        355                 360                 365

Pro Asn Lys Pro Tyr Glu Arg Glu Tyr Glu Arg Arg Leu Arg Glu Ser
370                 375                 380

Tyr Thr Gly Gly Phe Val Lys Glu Pro Glu Lys Gly Leu Trp Glu Ser
385                 390                 395                 400
```

```
Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Lys Asp Tyr
            420                 425                 430

Asp Ile Ala Pro Glu Val Gly His Lys Phe Cys Lys Asp Phe Leu Gly
            435                 440                 445

Phe Ile Pro Ser Leu Leu Gly His Leu Leu Glu Arg Gln Glu Ile
450                 455                 460

Lys Thr Lys Met Lys Glu Thr Xaa Asp Pro Ile Glu Lys Ile Leu Leu
465                 470                 475                 480

Asp Tyr Arg Gln Lys Ala Ile Lys Leu Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
            515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Glu Pro Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Ile Ile Thr Arg Gly
595                 600                 605

Leu Glu Ile Val Arg Arg Asp Trp Ser Glu Ile Ala Lys Glu Thr Gln
            610                 615                 620

Ala Lys Val Leu Glu Ala Ile Leu Lys His Gly Asn Val Glu Glu Ala
625                 630                 635                 640

Val Lys Ile Val Lys Glu Ile Ile Glu Lys Leu Ala Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
            675                 680                 685

Ala Arg Gly Val Lys Ile Lys Pro Gly Met Val Ile Gly Tyr Ile Val
690                 695                 700

Leu Arg Gly Asp Gly Pro Ile Ser Lys Arg Ala Ile Leu Ala Glu Glu
705                 710                 715                 720

Phe Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Ala Gly Leu Thr Ala
            755                 760                 765

Trp Leu Asn Ile Lys Lys Ser
770                 775

<210> SEQ ID NO 13
<211> LENGTH: 2535
<212> TYPE: DNA
<213> ORGANISM: Artificial Sequence
<220> FEATURE:
```

<223> OTHER INFORMATION: Description of Artificial Sequence:hybrid
polymerase Hyb1-Sso7d fusion protein HyS1
<220> FEATURE:
<221> NAME/KEY: modified_base
<222> LOCATION: (1416)
<223> OTHER INFORMATION: n = g, a, c or t

<400> SEQUENCE: 13

```
atgatcctgg atgctgacta catcactgaa gacggcaaac cggttatccg tctcttcaaa      60
aaagagaacg gcgaatttaa gattgagtat gatcgcacct ttcgtccata catttacgct     120
ctgctgagag atgattctaa gattgaggaa gttagaaaaa tcactgctga gcgccatggc     180
aagattgttc gtatcgttga tgtggaaaag gtaaggaaga aatttctggg cagaccaatc     240
aaggtgtgga gactgtattt cgaacatcca caagatgttc cgactattcg cgataaagtt     300
cgcgaacatc ctgcagttat tgacatcttc gaatacgata ttgcatttgc aaagcgttac     360
ctcatcgaca aaggcctgat accaatggag ggcgaggaag aactcaagat cctggcgttc     420
gatatagaaa ccctctatca cggaagcgaa gagtttggta aaggcccaat tataatgatc     480
agctatgcag atgaaaacga agcaaaggtg attacttgga aaaacataga tctcccatac     540
gttgaggttg tatcttccga gcgcgagatg attaaacgct ttctcagaat tatccgcgag     600
aaggatccgg acattatcgt tacttataac ggcgactctt ttgacctccc atatctggcg     660
aaacgcgcag aaaaactcgg tattaaactg actctcggcc gtgatggttg cgaggcgaag     720
atgcagcgtc tcggcgatat gaccgctgta gaagttaagg gtcgtatcca tttcgacctg     780
tattatgtaa ttagccgtac tattaacctc ccgacttaca ctctcgaggc tgtatatgaa     840
gcaattttg gtaagccgaa ggagaaggta tacgccgatg atattgcaga ggcgtgggaa     900
accggtaagg gcctcgagcg tgttgcaaaa tactccatgg aagatgcaaa ggcgacttat     960
gaactcggca agaattcct cccaatggaa gctcagctct ctcgcctggt tggccaacca    1020
ctgtgggatg tttctcgttc ttccaccggt aacctcgtag agtggtatct cctgcgcaaa    1080
gcgtacgaac gcaacgaagt ggctccgaac aagccatacg aacgagagta tgaacgccgt    1140
ctccgcgagt cttacactgg tggctttgtt aagagccag aaaagggcct ctgggaaagc    1200
ctcgtgtccc tcgattttcg ctctctgtat ccgtctatta tcattaccca caacgtgtct    1260
ccggatactc tcaaccgcga gggctgcaaa gactatgata ttgctccgga agtaggccac    1320
aagttctgca aggacttcct tggctttatt ccgtctctcc tggggcatct gctcgaggaa    1380
cgccaagaga ttaagaccaa aatgaaggag accangatc cgattgaaaa atactgctc    1440
gactatcgcc aaaaagcgat taaactcctc gcaaactctt attacggcta ttatggctat    1500
gcaaaagcac gctggtactg taaggagtgt gctgagtccg ttactgcttg gggtcgcgaa    1560
tacatcgagt tcgtgtggaa ggagctcgaa gaaaagtttg gctttaaagt tctctacatt    1620
gacactgatg gtctctatgc gactattccg ggtggtgagc tgaggaaat taagaaaaag    1680
gctctagaat ttgtgaaata cattaactcg aagctccccg gtctcttgga gctcgaatat    1740
gaaggctttt ataagcgcgg cttcttcgtt accaagaaga gatatgcggt gattgatgaa    1800
gaaggcaaaa ttattactcg tggtctcgag attgtgcgcc gtgattggag cgaaattgcg    1860
aaagaaactc aagctaaagt tctcgaggct attctcaaac acggcaacgt tgaagaagct    1920
gtgaaaattg taaagaaat aatcgaaaag ctcgctaaat atgaaatacc gccagagaag    1980
ctcgcgattt atgagcagat tactcgcccg ctgcatgagt ataaggcgat tggtccgcac    2040
gtggctgttg caaagaaact ggctgctaga ggcgtgaaaa ttaaaccggg tatggtaatt    2100
```

-continued

```
ggctacattg tactccgcgg cgatggtccg attagcaaac gtgcaattct agctgaggaa    2160
ttcgatccga aaaagcacaa gtatgacgca gaatattaca ttgagaacca ggtgctcccg    2220
gcggtactcc gtattctgga gggttttggc taccgtaagg aagacctccg ttggcaaaag    2280
actaaacagg ctggcctcac tgcttggctc aacattaaaa aatccggtac cggcggtggc    2340
ggtgcaaccg taaagttcaa gtacaaaggc gaagaaaaag aggtagacat ctccaagatc    2400
aagaaagtat ggcgtgtggg caagatgatc tccttcacct acgacgaggg cggtggcaag    2460
accggccgtg gtgcggtaag cgaaaaggac gcgccgaagg agctgctgca gatgctggag    2520
aagcagaaaa agtga                                                     2535
```

<210> SEQ ID NO 14
<211> LENGTH: 844
<212> TYPE: PRT
<213> ORGANISM: Artificial Sequence
<220> FEATURE:
<223> OTHER INFORMATION: Description of Artificial Sequence:hybrid
      polymerase Hyb1-Sso7d fusion protein HyS1
<220> FEATURE:
<221> NAME/KEY: MOD_RES
<222> LOCATION: (472)
<223> OTHER INFORMATION: Xaa = unknown amino acid

<400> SEQUENCE: 14

```
Met Ile Leu Asp Ala Asp Tyr Ile Thr Glu Asp Gly Lys Pro Val Ile
  1               5                  10                  15

Arg Leu Phe Lys Lys Glu Asn Gly Glu Phe Lys Ile Glu Tyr Asp Arg
             20                  25                  30

Thr Phe Arg Pro Tyr Ile Tyr Ala Leu Leu Arg Asp Asp Ser Lys Ile
         35                  40                  45

Glu Glu Val Arg Lys Ile Thr Ala Glu Arg His Gly Lys Ile Val Arg
     50                  55                  60

Ile Val Asp Val Glu Lys Val Arg Lys Lys Phe Leu Gly Arg Pro Ile
 65                  70                  75                  80

Lys Val Trp Arg Leu Tyr Phe Glu His Pro Gln Asp Val Pro Thr Ile
                 85                  90                  95

Arg Asp Lys Val Arg Glu His Pro Ala Val Ile Asp Ile Phe Glu Tyr
            100                 105                 110

Asp Ile Ala Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Gly Ser Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Leu Pro Tyr Leu Ala Lys Arg Ala Glu
    210                 215                 220

Lys Leu Gly Ile Lys Leu Thr Leu Gly Arg Asp Gly Cys Glu Ala Lys
225                 230                 235                 240

Met Gln Arg Leu Gly Asp Met Thr Ala Val Glu Val Lys Gly Arg Ile
                245                 250                 255
```

-continued

```
His Phe Asp Leu Tyr Tyr Val Ile Ser Arg Thr Ile Asn Leu Pro Thr
                260                 265                 270

Tyr Thr Leu Glu Ala Val Tyr Glu Ala Ile Phe Gly Lys Pro Lys Glu
            275                 280                 285

Lys Val Tyr Ala Asp Asp Ile Ala Glu Ala Trp Glu Thr Gly Lys Gly
        290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Val Ala
        355                 360                 365

Pro Asn Lys Pro Tyr Glu Arg Glu Tyr Glu Arg Arg Leu Arg Glu Ser
    370                 375                 380

Tyr Thr Gly Gly Phe Val Lys Glu Pro Glu Lys Gly Leu Trp Glu Ser
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Lys Asp Tyr
            420                 425                 430

Asp Ile Ala Pro Glu Val Gly His Lys Phe Cys Lys Asp Phe Leu Gly
        435                 440                 445

Phe Ile Pro Ser Leu Leu Gly His Leu Leu Glu Glu Arg Gln Glu Ile
    450                 455                 460

Lys Thr Lys Met Lys Glu Thr Xaa Asp Pro Ile Glu Lys Ile Leu Leu
465                 470                 475                 480

Asp Tyr Arg Gln Lys Ala Ile Lys Leu Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Pro Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Ile Glu Lys Leu Ala Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
```

-continued

```
                675                 680                 685
Ala Arg Gly Val Lys Ile Lys Pro Gly Met Val Ile Gly Tyr Ile Val
    690                 695                 700

Leu Arg Gly Asp Gly Pro Ile Ser Lys Arg Ala Ile Leu Ala Glu Glu
705                 710                 715                 720

Phe Asp Pro Lys Lys His Lys Tyr Asp Ala Glu Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Trp Gln Lys Thr Lys Gln Ala Gly Leu Thr Ala
        755                 760                 765

Trp Leu Asn Ile Lys Lys Ser Gly Thr Gly Gly Gly Ala Thr Val
    770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys
        835                 840
```

<210> SEQ ID NO 15
<211> LENGTH: 2340
<212> TYPE: DNA
<213> ORGANISM: Artificial Sequence
<220> FEATURE:
<223> OTHER INFORMATION: Description of Artificial Sequence:truncated
      hybrid polymerase Hyb2
<220> FEATURE:
<221> NAME/KEY: modified_base
<222> LOCATION: (1416)
<223> OTHER INFORMATION: n = g, a, c or t

<400> SEQUENCE: 15

```
atgatcctgg atgctgacta catcactgaa gaaggcaaac cggttatccg tatcttcaaa      60
aaagagaacg gcgaatttaa ggttgagtat gatcgcaact ttcgtccata catttacgct     120
ctgctggaag atgattctaa gattgatgaa gttagaaaaa tcactgctga gcgccatggc     180
aagattgttc gtatcgttga tgcggaaaag gtagagaaga aatttctggg cagaccaatc     240
acggtgtgga aactgtattt cgaacatcca caagatgttc cgactattcg cgagaaaatt     300
cgcgaacatt ctgcagttgt tggcatcttc gaatacgata ttccatttgc aaagagttac     360
ctcatcgaca aaggcctgat accaatggag ggcgaggaag aactcaagct cctggcgttc     420
gatatagaaa ccctctatca cgaaggcgaa gagtttgcta aggcccaat tataatgatc      480 agctatgcag atgaagacga agcaaaggtg attacttgga aaaaataga ctctcccatac     540 gttgaggttg tatcttccga gcgcgagatg attaagcgct ttctcagagt tatccgcgag     600
aaggatccgg acgttatcgt tacttataac ggcgactctt ttgacctccc atatctggcg     660
aaacgcgcag aaaaactcgg tattaaactg cctctcggcc gtgatggttc cgagccgaag     720
atgcagcgtc tcggcgatat gaccgctgta gaagttaagg gtcgtatcca tttcgacctg     780
tatcatgtaa ttagccgtac tattaacctc ccgacttaca ctctcgaggc tgtatatgaa     840 gcaattttg gtaagccgaa ggagaaggta tacgccgatg agattgcagg ggcgtgggaa     900
accggtgagg acctcgagcg tgttgcaaaa tactccatgg aagatgcaaa ggcgatttat     960
```

-continued

```
gaactcggca aagaattctt cccaatggaa gttcagctcc ctcgcctggt tggccaacca    1020
ctgtgggatg tttctcgttc ttccaccggt aacctcgtag agtggttgct cctgcgcaaa    1080
gcgtacgaac gcaacgaact ggctccgaac aagccagccg aacaagagta tgaacgccgt    1140
ctccgcgagt cttacactgg tggctttgtt aaagagccag aaaagggcct ctgggaagac    1200
ctcgtgtccc tcgattttcg cgctctgtat ccgtctatta tcattaccca caacgtgtct    1260
ccggatactc tcaaccgcga gggctgcaaa gactatgata ttgctccgga agtaggccac    1320
aagttctgca aggacttcct tggctttatt ccgtctctcc tggggcatct gctcgaggaa    1380
cgccaagaga ttaagaccaa aatgaaggag acccangatc cgattgaaaa aatactgctc    1440
gactatcgcc aaaaagcgat taaactcctc gcaaactctt attacggcta ttatggctat    1500
gcaaaagcac gctggtactg taaggagtgt gctgagtccg ttactgcttg ggtcgcgaa    1560 tacatcgagt tcgtgtggaa ggagctcgaa gaaaagtttg gctttaaagt tctctacatt    1620
gacactgatg gtctctatgc gactattccg ggtggtgagc ctgaggaaat taagaaaaag    1680
gctctagaat ttgtgaaata cattaactcg aagctccccg gtctcttgga gctcgaatat    1740
gaaggctttt ataagcgcgg cttcttcgtt accaagaaga gatatgcggt gattgatgaa    1800
gaaggcaaaa ttattactcg tggtctcgag attgtgcgcc gtgattggag cgaaattgcg    1860
aaagaaactc aagctaaagt tctcgaggct attctcaaac acggcaacgt tgaagaagct    1920
gtgaaaattg taaagaaat aatcgaaaag ctcgctaaat atgaaatacc gccagagaag    1980
ctcgcgattt atgagcagat tactcgcccg ctgcatgagt ataaggcgat tggtccgcac    2040
gtggctgttg caaagaaact ggctgctaga ggcgtgaaaa ttaaaccggg tatggtaatt    2100
ggctacattg tactccgcgg cgatggtccg attagcaacc gtgcaattct agctgaggaa    2160
ttcgatctga gaaagcacaa gtatgacgca gaatattaca ttgagaacca ggtgctcccg    2220
gcggtactcc gtattctgga gggttttggc taccgtaagg aagacctccg ttagcaaaag    2280
actaaacagg ctggactcac tgcttggctc atcattaaaa aatccggtac ccactagtgc    2340
```

<210> SEQ ID NO 16
<211> LENGTH: 757
<212> TYPE: PRT
<213> ORGANISM: Artificial Sequence
<220> FEATURE:
<223> OTHER INFORMATION: Description of Artificial Sequence:truncated
      hybrid polymerase Hyb2
<220> FEATURE:
<221> NAME/KEY: MOD_RES
<222> LOCATION: (472)
<223> OTHER INFORMATION: Xaa = unknown amino acid

<400> SEQUENCE: 16

```
Met Ile Leu Asp Ala Asp Tyr Ile Thr Glu Glu Gly Lys Pro Val Ile
 1               5                  10                  15

Arg Ile Phe Lys Lys Glu Asn Gly Glu Phe Lys Val Glu Tyr Asp Arg
                20                  25                  30

Asn Phe Arg Pro Tyr Ile Tyr Ala Leu Leu Glu Asp Asp Ser Lys Ile
            35                  40                  45

Asp Glu Val Arg Lys Ile Thr Ala Glu Arg His Gly Lys Ile Val Arg
        50                  55                  60

Ile Val Asp Ala Glu Lys Val Glu Lys Lys Phe Leu Gly Arg Pro Ile
 65                  70                  75                  80

Thr Val Trp Lys Leu Tyr Phe Glu His Pro Gln Asp Val Pro Thr Ile
                85                  90                  95
```

-continued

```
Arg Glu Lys Ile Arg Glu His Ser Ala Val Val Gly Ile Phe Glu Tyr
            100                 105                 110
Asp Ile Pro Phe Ala Lys Ser Tyr Leu Ile Asp Lys Gly Leu Ile Pro
            115                 120                 125
Met Glu Gly Glu Glu Leu Lys Leu Leu Ala Phe Asp Ile Glu Thr
        130                 135                 140
Leu Tyr His Glu Gly Glu Glu Phe Ala Lys Gly Pro Ile Ile Met Ile
145                 150                 155                 160
Ser Tyr Ala Asp Glu Asp Glu Ala Lys Val Ile Thr Trp Lys Lys Ile
                165                 170                 175
Asp Leu Pro Tyr Val Glu Val Val Ser Ser Glu Arg Glu Met Ile Lys
            180                 185                 190
Arg Phe Leu Arg Val Ile Arg Glu Lys Asp Pro Asp Val Ile Val Thr
            195                 200                 205
Tyr Asn Gly Asp Ser Phe Asp Leu Pro Tyr Leu Ala Lys Arg Ala Glu
        210                 215                 220
Lys Leu Gly Ile Lys Leu Pro Leu Gly Arg Asp Gly Ser Glu Pro Lys
225                 230                 235                 240
Met Gln Arg Leu Gly Asp Met Thr Ala Val Glu Val Lys Gly Arg Ile
                245                 250                 255
His Phe Asp Leu Tyr His Val Ile Ser Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Gly Ala Trp Glu Thr Gly Glu Asp
    290                 295                 300
Leu Glu Arg Val Ala Lys Tyr Ser Met Glu Asp Ala Lys Ala Ile Tyr
305                 310                 315                 320
Glu Leu Gly Lys Glu Phe Phe Pro Met Glu Val Gln Leu Pro Arg Leu
                325                 330                 335
Val Gly Gln Pro Leu Trp Asp Val Ser Arg Ser Ser Thr Gly Asn Leu
            340                 345                 350
Val Glu Trp Leu Leu Leu Arg Lys Ala Tyr Glu Arg Asn Glu Leu Ala
        355                 360                 365
Pro Asn Lys Pro Ala Glu Gln Glu Tyr Glu Arg Arg Leu Arg Glu Ser
    370                 375                 380
Tyr Thr Gly Gly Phe Val Lys Glu Pro Glu Lys Gly Leu Trp Glu Asp
385                 390                 395                 400
Leu Val Ser Leu Asp Phe Arg Ala Leu Tyr Pro Ser Ile Ile Ile Thr
                405                 410                 415
His Asn Val Ser Pro Asp Thr Leu Asn Arg Glu Gly Cys Lys Asp Tyr
            420                 425                 430
Asp Ile Ala Pro Glu Val Gly His Lys Phe Cys Lys Asp Phe Leu Gly
        435                 440                 445
Phe Ile Pro Ser Leu Leu Gly His Leu Leu Glu Glu Arg Gln Glu Ile
    450                 455                 460
Lys Thr Lys Met Lys Glu Thr Xaa Asp Pro Ile Glu Lys Ile Leu Leu
465                 470                 475                 480
Asp Tyr Arg Gln Lys Ala Ile Lys Leu Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Phe Val Trp Lys Glu
```

-continued

```
                      515                 520                 525
Leu Glu Glu Lys Phe Gly Phe Lys Val Leu Tyr Ile Asp Thr Asp Gly
            530                 535                 540

Leu Tyr Ala Thr Ile Pro Gly Gly Glu Pro Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
        610                 615                 620

Ala Lys Val Leu Glu Ala Ile Leu Lys His Gly Asn Val Glu Glu Ala
625                 630                 635                 640

Val Lys Ile Val Lys Glu Ile Ile Glu Lys Leu Ala Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
    675                 680                 685

Ala Arg Gly Val Lys Ile Lys Pro Gly Met Val Ile Gly Tyr Ile Val
            690                 695                 700

Leu Arg Gly Asp Gly Pro Ile Ser Asn Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg
        755

<210> SEQ ID NO 17
<211> LENGTH: 2340
<212> TYPE: DNA
<213> ORGANISM: Artificial Sequence
<220> FEATURE:
<223> OTHER INFORMATION: Description of Artificial Sequence:truncated
      hybrid polymerase Hyb3
<220> FEATURE:
<221> NAME/KEY: modified_base
<222> LOCATION: (1416)
<223> OTHER INFORMATION: n = g, a, c or t

<400> SEQUENCE: 17
atgatcctgg atgctgacta catcactgaa gaaggcaaac cggttatccg tatcttcaaa      60
aaagagaacg gcgaatttaa ggttgagtat gatcgcaact ttcgtccata catttacgct     120
ctgctggaag atgattctaa gattgatgaa gttagaaaaa tcactgctga gcgccatggc     180
aagattgttc gtatcgttga tgcggaaaag gtagagaaga aatttctggg cagaccaatc     240
acggtgtgga aactgtattt cgaacatcca caagatgttc gactattcg cgagaaatt     300 cgcgaacatt ctgcagttgt tggcatcttc gaatacgata ttccatttgc aaagagttac     360
ctcatcgaca aaggcctgat accaatggag ggcgaggaag aactcaagct cctggcgttc     420
gatatagaaa ccctctatca cgaaggcgaa gagtttgcta aaggcccaat tataatgatc     480
agctatgcag atgaagacga agcaaggtg attacttgga aaaaaatga ctctcccata c     540
```

```
gttgaggttg tatcttccga gcgcgagatg attaagcgct ttctcagagt tatccgcgag    600
aaggatccgg acgttatcgt tacttataac ggcgactctt ttgacctccc atatctggcg    660
aaacgcgcag aaaaactcgg tattaaactg cctctcggcc gtgatggttc cgagccgaag    720
atgcagcgtc tcggcgatat gaccgctgta gaagttaagg gtcgtatcca tttcgacctg    780
tatcatgtaa ttagccgtac tattaacctc ccgacttaca ctctcgaggc tgtatatgaa    840 gcaattttg gtaagccgaa ggagaaggta tacgccgatg agattgcagg ggcgtgggaa     900
accggtgagg acctcgagcg tgttgcaaaa tactccatgg aagatgcaaa ggcgatttat    960
gaactcggca agaattctt cccaatggaa gttcagctcc ctcgcctggt tggccaacca    1020
ctgtgggatt tttctcgttc ttccaccggt aacctcgtag agtggttgct cctgcgcaaa   1080
gcgtacgaac gcaacgaact ggctccgaac aagccagccg aacaagagta tgaacgccgt   1140
ctccgcgagt cttacactgg tggctttgtt aaagagccag aaaagggcct ctgggaagac   1200
ctcgtgtccc tcgattttcg cgctctgtat ccgtctatta tcattaccca caacgtgtct   1260
ccggatactc tcaaccgcga gggctgcaaa gactatgata ttgctccgga agtaggccac   1320
aagttctgca aggacttcct tggctttatt ccgtctctcc tggggcatct gctcgaggaa   1380
cgccaagaga ttaagaccaa aatgaaggag acccangatc cgattgaaaa aatactgctc   1440
gactatcgcc aaaaagcgat taaactcctc gcaaactctt attacggcta ttatggctat   1500
gcaaaagcac gctggtactg taaggagtgt gctgagtccg ttactgcttg gggtcgcgaa   1560
tacatcgagt tcgtgtggaa ggagctcgaa gaaaagtttg gctttaaagt tctctacatt   1620
gacactgatg gtctctatgc gactattccg ggtggtgagc ctgaggaaat taagaaaaag   1680
gctctagaat ttgtgaaata cattaactcg aagctccccg gtctcttgga gctcgaatat   1740
gaaggctttt ataagcgcgg cttcttcgtt accaagaaga gatatgcggt gattgatgaa   1800
gaaggcaaaa ttattactcg tggtctcgag attgtgcgcc gtgattggag cgaaattgcg   1860
aaagaaactc aagctaaagt tctcgaggct attctcaaac acggcaacgt tgaagaagct   1920
gtgaaaattg taaagaaat aatcgaaaag ctcgctaaat atgaaatacc gccagagaag   1980
ctcgcgattt atgagcagat tactcgcccg ctgcatgagt ataaggcgat tggtccgcac   2040
gtggctgttg caaagaaact ggctgctaga ggcgtgaaaa ttaaaccggg tatggtaatt   2100
ggctacattg tactccgcgg cgatggtccg attagcaacc gtgcaattct agctgaggaa   2160
ttcgatctga gaaagcacaa gtatgacgca gaatattaca ttgagaacca ggtgctcccg   2220
gcggtactcc gtattctgga gggttttggc taccgtaagg aagacctccg ttagcaaaag   2280
actaaacagg ctggactcac tgcttggctc atcattaaaa aatccggtac ccactagtgc   2340
```

<210> SEQ ID NO 18
<211> LENGTH: 757
<212> TYPE: PRT
<213> ORGANISM: Artificial Sequence
<220> FEATURE:
<223> OTHER INFORMATION: Description of Artificial Sequence:truncated
      hybrid polymerase Hyb3
<220> FEATURE:
<221> NAME/KEY: MOD_RES
<222> LOCATION: (472)
<223> OTHER INFORMATION: Xaa = unknown amino acid

<400> SEQUENCE: 18

Met Ile Leu Asp Ala Asp Tyr Ile Thr Glu Glu Gly Lys Pro Val Ile
 1               5                  10                  15

```
Arg Ile Phe Lys Lys Glu Asn Gly Glu Phe Lys Val Glu Tyr Asp Arg
             20                  25                  30

Asn Phe Arg Pro Tyr Ile Tyr Ala Leu Leu Glu Asp Ser Lys Ile
         35                  40                  45

Asp Glu Val Arg Lys Ile Thr Ala Glu Arg His Gly Lys Ile Val Arg
     50                  55                  60

Ile Val Asp Ala Glu Lys Val Glu Lys Lys Phe Leu Gly Arg Pro Ile
 65                  70                  75                  80

Thr Val Trp Lys Leu Tyr Phe Glu His Pro Gln Asp Val Pro Thr Ile
                 85                  90                  95

Arg Glu Lys Ile Arg Glu His Ser Ala Val Val Gly Ile Phe Glu Tyr
                100                 105                 110

Asp Ile Pro Phe Ala Lys Ser Tyr Leu Ile Asp Lys Gly Leu Ile Pro
            115                 120                 125

Met Glu Gly Glu Glu Leu Lys Leu Leu Ala Phe Asp Ile Glu Thr
130                 135                 140

Leu Tyr His Glu Gly Glu Glu Phe Ala Lys Gly Pro Ile Ile Met Ile
145                 150                 155                 160

Ser Tyr Ala Asp Glu Asp Glu Ala Lys Val Ile Thr Trp Lys Lys Ile
                165                 170                 175

Asp Leu Pro Tyr Val Glu Val Ser Ser Glu Arg Glu Met Ile Lys
            180                 185                 190

Arg Phe Leu Arg Val Ile Arg Glu Lys Asp Pro Asp Val Ile Val Thr
        195                 200                 205

Tyr Asn Gly Asp Ser Phe Asp Leu Pro Tyr Leu Ala Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Val Lys Gly Arg Ile
                245                 250                 255

His Phe Asp Leu Tyr His Val Ile Ser Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Gly Ala Trp Glu Thr Gly Glu Asp
    290                 295                 300

Leu Glu Arg Val Ala Lys Tyr Ser Met Glu Asp Ala Lys Ala Ile Tyr
305                 310                 315                 320

Glu Leu Gly Lys Glu Phe Phe Pro Met Glu Val Gln Leu Pro Arg Leu
                325                 330                 335

Val Gly Gln Pro Leu Trp Asp Val Ser Arg Ser Ser Thr Gly Asn Leu
            340                 345                 350

Val Glu Trp Leu Leu Leu Arg Lys Ala Tyr Glu Arg Asn Glu Leu Ala
        355                 360                 365

Pro Asn Lys Pro Ala Glu Gln Glu Tyr Glu Arg Arg Leu Arg Glu Ser
    370                 375                 380

Tyr Thr Gly Gly Phe Val Lys Glu Pro Glu Lys Gly Leu Trp Glu Asp
385                 390                 395                 400

Leu Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Lys Asp Tyr
            420                 425                 430

Asp Ile Ala Pro Glu Val Gly His Lys Phe Cys Lys Asp Phe Leu Gly
```

```
              435                 440                 445
Phe Ile Pro Ser Leu Leu Gly His Leu Leu Glu Glu Arg Gln Glu Ile
    450                 455                 460

Lys Thr Lys Met Lys Glu Thr Xaa Asp Pro Ile Glu Lys Ile Leu Leu
465                 470                 475                 480

Asp Tyr Arg Gln Lys Ala Ile Lys Leu Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Pro Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Ile Ile Glu Lys Leu Ala Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Leu Ala
        675                 680                 685

Ala Arg Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg
        755

<210> SEQ ID NO 19
<211> LENGTH: 2535
<212> TYPE: DNA
<213> ORGANISM: Artificial Sequence
<220> FEATURE:
<223> OTHER INFORMATION: Description of Artificial Sequence:hybrid
      polymerase Sso7d fusion protein HyS4
<220> FEATURE:
<221> NAME/KEY: modified_base
<222> LOCATION: (1416)
<223> OTHER INFORMATION: n = g, a, c or t

<400> SEQUENCE: 19
atgatcctgg atgctgacta catcactgaa gaaggcaaac cggttatccg tatcttcaaa    60
```

-continued

```
aaagagaacg gcgaatttaa ggttgagtat gatcgcaact ttcgtccata catttacgct    120
ctgctggaag atgattctaa gattgatgaa gttagaaaaa tcactgctga gcgccatggc    180
aagattgttc gtatcgttga tgcggaaaag gtagagaaga aatttctggg cagaccaatc    240
acggtgtgga aactgtattt cgaacatcca caagatgttc cgactattcg cgagaaaatt    300
cgcgaacatt ctgcagttgt tggcatcttc gaatacgata ttccatttgc aaagagttac    360
ctcatcgaca aaggcctgat accaatggag ggcgaggaag aactcaagct cctggcgttc    420
gatatagaaa ccctctatca cgaaggcgaa gagtttgcta aaggcccaat tataatgatc    480
agctatgcag atgaagacga agcaaggtg attacttgga aaaaaataga tctcccatac     540
gttgaggttg tatcttccga gcgcgagatg attaagcgct ttctcagagt tatccgcgag    600
aaggatccgg acgttatcgt tacttataac ggcgactctt ttgacctccc atatctggcg    660
aaacgcgcag aaaaactcgg tattaaactg cctctcggcc gtgatggttc cgagccgaag    720
atgcagcgtc tcggcgatat gaccgctgta gaagttaagg gtcgtatcca tttcgacctg    780
tatcatgtaa ttagccgtac tattaacctc ccgacttaca ctctcgaggc tgtatatgaa    840 gcaattttg gtaagccgaa ggagaaggta tacgccgatg agattgcagg ggcgtgggaa     900
accggtgagg acctcgagcg tgttgcaaaa tactccatgg aagatgcaaa ggcgatttat    960
gaactcggca agaattctt cccaatggaa gttcagctcc ctcgcctggt tggccaacca    1020
ctgtgggatg tttctcgttc ttccaccggt aacctcgtag agtggttgct cctgcgcaaa   1080
gcgtacgaac gcaacgaact ggctccgaac aagccagccg aacaagagta tgaacgccgt   1140
ctccgcgagt cttacactgg tggctttgtt aaagagccag aaaagggcct ctgggaagac   1200
ctcgtgtccc tcgattttcg cgctctgtat ccgtctatta tcattaccca caacgtgtct   1260
ccggatactc tcaaccgcga gggctgcaaa gactatgata ttgctccgga gtaggccac    1320 aagttctgca aggacttcct tggctttatt ccgtctctcc tggggcatct gctcgaggaa   1380
cgccaagaga ttaagaccaa aatgaaggag acccangatc cgattgaaaa aatactgctc   1440
gactatcgcc aaaaagcgat taaactcctc gcaaactctt attacggcta ttatggctat   1500
gcaaaagcac gctggtactg taaggagtgt gctgagtccg ttactgcttg gggtcgcgaa   1560
tacatcgagt tcgtgtggaa ggagctcgaa gaaaagtttg gctttaaagt tctctacatt   1620
gacactgatg gtctctatgc gactattccg ggtggtgagc tgaggaaat taagaaaaag    1680 gctctagaat ttgtgaaata cattaactcg aagctccccg gtctcttgga gctcgaatat   1740
gaaggctttt ataagcgcgg cttcttcgtt accaagaaga gatatgcggt gattgatgaa   1800
gaaggcaaaa ttattactcg tggtctcgag attgtgcgcc gtgattggag cgaaattgcg   1860
aaagaaactc aagctaaagt tctcgaggct attctcaaac acggcaacgt tgaagaagct   1920
gtgaaaattg taaagaaat aatcgaaaag ctcgctaaat atgaaatacc gccagagaag   1980
ctcgcgattt atgagcagat tactcgcccg ctgcatgagt ataaggcgat tggtccgcac   2040
gtggctgttg caagaaaact ggctgctaga ggcgtgaaaa ttaaaccggg tatggtaatt   2100
ggctacattg tactccgcgg cgatggtccg attagcaaac gtgcaattct agctgaggaa   2160
ttcgatccga aaaagcacaa gtatgacgca gaatattaca ttgagaacca ggtgctcccg   2220
gcggtactcc gtattctgga gggttttggc taccgtaagg aagacctccg ttggcaaaag   2280
actaaacagg ctggcctcac tgcttggctc aacattaaaa aatccggtac cggcggtggc   2340
ggtgcaaccg taagttcaa gtacaaaggc gaagaaaaag aggtagacat ctccaagatc   2400
aagaaagtat ggcgtgtggg caagatgatc tccttcacct acgacgaggg cggtggcaag   2460
```

```
accggccgtg gtgcggtaag cgaaaaggac gcgccgaagg agctgctgca gatgctggag    2520
aagcagaaaa agtga                                                     2535
```

<210> SEQ ID NO 20
<211> LENGTH: 844
<212> TYPE: PRT
<213> ORGANISM: Artificial Sequence
<220> FEATURE:
<223> OTHER INFORMATION: Description of Artificial Sequence:hybrid
    polymerase Sso7d fusion protein HyS4
<220> FEATURE:
<221> NAME/KEY: MOD_RES
<222> LOCATION: (472)
<223> OTHER INFORMATION: Xaa = unknown amino acid

<400> SEQUENCE: 20

```
Met Ile Leu Asp Ala Asp Tyr Ile Thr Glu Glu Gly Lys Pro Val Ile
 1               5                  10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Glu Asp Asp Ser Lys Ile
        35                  40                  45

Asp Glu Val Arg Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
 65                 70                  75                  80

Thr Val Trp Lys Leu Tyr Phe Glu His Pro Gln Asp Val Pro Thr Ile
                85                  90                  95

Arg Glu Lys Ile Arg Glu His Ser Ala Val Val Gly Ile Phe Glu Tyr
            100                 105                 110

Asp Ile Pro Phe Ala Lys Ser Tyr Leu Ile Asp Lys Gly Leu Ile Pro
        115                 120                 125

Met Glu Gly Glu Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Asp Glu Ala Lys Val Ile Thr Trp Lys Lys Ile
                165                 170                 175

Asp Leu Pro Tyr Val Glu Val Ser Ser Glu Arg Glu Met Ile Lys
            180                 185                 190

Arg Phe Leu Arg Val Ile Arg Glu Lys Asp Pro Asp Val Ile Val Thr
        195                 200                 205

Tyr Asn Gly Asp Ser Phe Asp Leu Pro Tyr Leu Ala Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Val Lys Gly Arg Ile
                245                 250                 255

His Phe Asp Leu Tyr His Val Ile Ser Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Gly Ala Trp Glu Thr Gly Glu Asp
    290                 295                 300

Leu Glu Arg Val Ala Lys Tyr Ser Met Glu Asp Ala Lys Ala Ile Tyr
305                 310                 315                 320
```

-continued

```
Glu Leu Gly Lys Glu Phe Phe Pro Met Glu Val Gln Leu Pro Arg Leu
            325                 330                 335
Val Gly Gln Pro Leu Trp Asp Val Ser Arg Ser Thr Gly Asn Leu
        340                 345                 350
Val Glu Trp Leu Leu Leu Arg Lys Ala Tyr Glu Arg Asn Glu Leu Ala
        355                 360                 365
Pro Asn Lys Pro Ala Glu Gln Glu Tyr Glu Arg Arg Leu Arg Glu Ser
        370                 375                 380
Tyr Thr Gly Gly Phe Val Lys Glu Pro Glu Lys Gly Leu Trp Glu Asp
385                 390                 395                 400
Leu Val Ser Leu Asp Phe Arg Ala Leu Tyr Pro Ser Ile Ile Ile Thr
                405                 410                 415
His Asn Val Ser Pro Asp Thr Leu Asn Arg Glu Gly Cys Lys Asp Tyr
                420                 425                 430
Asp Ile Ala Pro Glu Val Gly His Lys Phe Cys Lys Asp Phe Leu Gly
            435                 440                 445
Phe Ile Pro Ser Leu Leu Gly His Leu Leu Glu Glu Arg Gln Glu Ile
        450                 455                 460
Lys Thr Lys Met Lys Glu Thr Xaa Asp Pro Ile Glu Lys Ile Leu Leu
465                 470                 475                 480
Asp Tyr Arg Gln Lys Ala Ile Lys Leu Leu Ala Asn Ser Tyr Tyr Gly
                485                 490                 495
Tyr Tyr Gly Tyr Ala Lys Ala Arg Trp Tyr Cys Lys Glu Cys Ala Glu
                500                 505                 510
Ser Val Thr Ala Trp Gly Arg Glu Tyr Ile Glu Phe Val Trp Lys Glu
        515                 520                 525
Leu Glu Glu Lys Phe Gly Phe Lys Val Leu Tyr Ile Asp Thr Asp Gly
        530                 535                 540
Leu Tyr Ala Thr Ile Pro Gly Gly Glu Pro Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
                580                 585                 590
Lys Arg Tyr Ala Val Ile Asp Glu Glu Gly Lys Ile Ile Thr Arg Gly
        595                 600                 605
Leu Glu Ile Val Arg Arg Asp Trp Ser Glu Ile Ala Lys Glu Thr Gln
        610                 615                 620
Ala Lys Val Leu Glu Ala Ile Leu Lys His Gly Asn Val Glu Glu Ala
625                 630                 635                 640
Val Lys Ile Val Lys Glu Ile Ile Glu Lys Leu Ala Lys Tyr Glu Ile
                645                 650                 655
Pro Pro Glu Lys Leu Ala Ile Tyr Glu Gln Ile Thr Arg Pro Leu His
                660                 665                 670
Glu Tyr Lys Ala Ile Gly Pro His Val Ala Val Ala Lys Lys Leu Ala
        675                 680                 685
Ala Arg Gly Val Lys Ile Lys Pro Gly Met Val Ile Gly Tyr Ile Val
        690                 695                 700
Leu Arg Gly Asp Gly Pro Ile Ser Lys Arg Ala Ile Leu Ala Glu Glu
705                 710                 715                 720
Phe Asp Pro Lys Lys His Lys Tyr Asp Ala Glu Tyr Tyr Ile Glu Asn
                725                 730                 735
```

-continued

```
Gln Val Leu Pro Ala Val Leu Arg Ile Leu Glu Gly Phe Gly Tyr Arg
                740                 745                 750

Lys Glu Asp Leu Arg Trp Gln Lys Thr Lys Gln Ala Gly Leu Thr Ala
            755                 760                 765

Trp Leu Asn Ile Lys Lys Ser Gly Thr Gly Gly Gly Ala Thr Val
        770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys
        835                 840

<210> SEQ ID NO 21
<211> LENGTH: 189
<212> TYPE: DNA
<213> ORGANISM: Artificial Sequence
<220> FEATURE:
<223> OTHER INFORMATION: Description of Artificial Sequence:Sso7d coding
      region

<400> SEQUENCE: 21
accgtaaagt tcaagtacaa aggcgaagaa aagaggtag acatctccaa gatcaagaaa      60
gtatggcgtg tgggcaagat gatctccttc acctacgacg agggcggtgg caagaccggc   120
cgtggtgcgg taagcgaaaa ggacgcgccg aaggagctgc tgcagatgct ggagaagcag   180
aaaaagtga                                                            189

<210> SEQ ID NO 22
<211> LENGTH: 63
<212> TYPE: PRT
<213> ORGANISM: Artificial Sequence
<220> FEATURE:
<223> OTHER INFORMATION: Description of Artificial Sequence:Sso7d
      binding domain

<400> SEQUENCE: 22

Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys Lys
    50                  55                  60

<210> SEQ ID NO 23
<211> LENGTH: 25
<212> TYPE: PRT
<213> ORGANISM: Artificial Sequence
<220> FEATURE:
<223> OTHER INFORMATION: Description of Artificial Sequence:signature
      invariable sequence element in hybrid polymerases
      containing nucleotide binding motif

<400> SEQUENCE: 23

Tyr Gly Tyr Tyr Gly Tyr Ala Lys Ala Arg Trp Tyr Cys Lys Glu Cys
1               5                   10                  15

Ala Glu Ser Val Thr Ala Trp Gly Arg
            20                  25
```

```
                    20                  25

<210> SEQ ID NO 24
<211> LENGTH: 775
<212> TYPE: PRT
<213> ORGANISM: Pyrococcus furiosus
<220> FEATURE:
<223> OTHER INFORMATION: parent Pyrococcus furiosus family B DNA
      polymerase PolI (Pfu)

<400> SEQUENCE: 24

Met Ile Leu Asp Val Asp Tyr Ile Thr Glu Glu Gly Lys Pro Val Ile
  1               5                  10                  15

Arg Leu Phe Lys Lys Glu Asn Gly Lys Phe Lys Ile Glu His Asp Arg
                 20                  25                  30

Thr Phe Arg Pro Tyr Ile Tyr Ala Leu Leu Arg Asp Asp Ser Lys Ile
             35                  40                  45

Glu Glu Val Lys Lys Ile Thr Gly Glu Arg His Gly Lys Ile Val Arg
         50                  55                  60

Ile Val Asp Val Glu Lys Val Glu Lys Lys Phe Leu Gly Lys Pro Ile
 65                  70                  75                  80

Thr Val Trp Lys Leu Tyr Leu Glu His Pro Gln Asp Val Pro Thr Ile
                 85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350
```

-continued

```
Val Glu Trp Phe Leu Leu Arg Lys Ala Tyr Glu Arg Asn Glu Val Ala
            355                 360                 365

Pro Asn Lys Pro Ser Glu Glu Tyr Gln Arg Arg Leu Arg Glu Ser
370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
                420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
            690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
            755                 760                 765

Trp Leu Asn Ile Lys Lys Ser
```

```
                  770                 775

<210> SEQ ID NO 25
<211> LENGTH: 775
<212> TYPE: PRT
<213> ORGANISM: Pyrococcus sp.
<220> FEATURE:
<223> OTHER INFORMATION: parent Pyrococcus sp. strain GD-B PolI
      (Deep Vent) DNA polymerase

<400> SEQUENCE: 25

Met Ile Leu Asp Ala Asp Tyr Ile Thr Glu Asp Gly Lys Pro Ile Ile
  1               5                  10                  15

Arg Ile Phe Lys Lys Glu Asn Gly Glu Phe Lys Val Glu Tyr Asp Arg
             20                  25                  30

Asn Phe Arg Pro Tyr Ile Tyr Ala Leu Leu Lys Asp Asp Ser Gln Ile
         35                  40                  45

Asp Glu Val Arg Lys Ile Thr Ala Glu Arg His Gly Lys Ile Val Arg
     50                  55                  60

Ile Ile Asp Ala Glu Lys Val Arg Lys Phe Leu Gly Arg Pro Ile
 65                  70                  75                  80

Glu Val Trp Arg Leu Tyr Phe Glu His Pro Gln Asp Val Pro Ala Ile
                 85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350
```

-continued

```
Val Glu Trp Tyr Leu Leu Arg Lys Ala Tyr Glu Arg Asn Glu Leu Ala
        355                 360                 365
Pro Asn Lys Pro Asp Glu Arg Glu Tyr Glu Arg Arg Leu Arg Glu Ser
    370                 375                 380
Tyr Ala Gly Gly Tyr Val Lys Glu Pro Glu Lys Gly Leu Trp Glu Gly
385                 390                 395                 400
Leu Val Ser Leu Asp Phe Arg Ser Leu Tyr Pro Ser Ile Ile Ile Thr
                405                 410                 415
His Asn Val Ser Pro Asp Thr Leu Asn Arg Glu Gly Cys Arg Glu Tyr
            420                 425                 430
Asp Val Ala Pro Glu Val Gly His Lys Phe Cys Lys Asp Phe Pro Gly
        435                 440                 445
Phe Ile Pro Ser Leu Leu Lys Arg Leu Leu Asp Glu Arg Gln Glu Ile
    450                 455                 460
Lys Arg Lys Met Lys Ala Ser Lys Asp Pro Ile Glu Lys Lys Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Phe Val Arg Lys Glu
        515                 520                 525
Leu Glu Glu Lys Phe Gly Phe Lys Val Leu Tyr Ile Asp Thr Asp Gly
    530                 535                 540
Leu Tyr Ala Thr Ile Pro Gly Ala Lys Pro Glu Glu Ile Lys Lys Lys
545                 550                 555                 560
Ala Leu Glu Phe Val Asp Tyr Ile Asn Ala Lys Leu Pro Gly Leu Leu
                565                 570                 575
Glu Leu Glu Tyr Glu Gly Phe Tyr Val Arg Gly Phe Phe Val Thr Lys
            580                 585                 590
Lys Lys Tyr Ala Leu Ile Asp Glu Glu Gly Lys Ile Ile Thr Arg Gly
        595                 600                 605
Leu Glu Ile Val Arg Arg Asp Trp Ser Glu Ile Ala Lys Glu Thr Gln
    610                 615                 620
Ala Lys Val Leu Glu Ala Ile Leu Lys His Gly Asn Val Glu Glu Ala
625                 630                 635                 640
Val Lys Ile Val Lys Glu Val Thr Glu Lys Leu Ser Lys Tyr Glu Ile
                645                 650                 655
Pro Pro Glu Lys Leu Val Ile Tyr Glu Gln Ile Thr Arg Pro Leu His
            660                 665                 670
Glu Tyr Lys Ala Ile Gly Pro His Val Ala Val Ala Lys Arg Leu Ala
        675                 680                 685
Ala Arg Gly Val Lys Val Arg Pro Gly Met Val Ile Gly Tyr Ile Val
    690                 695                 700
Leu Arg Gly Asp Gly Pro Ile Ser Lys Arg Ala Ile Leu Ala Glu Glu
705                 710                 715                 720
Phe Asp Leu Arg Lys His Lys Tyr Asp Ala Glu Tyr Tyr Ile Glu Asn
                725                 730                 735
Gln Val Leu Pro Ala Val Leu Arg Ile Leu Glu Ala Phe Gly Tyr Arg
            740                 745                 750
Lys Glu Asp Leu Arg Trp Gln Lys Thr Lys Gln Thr Gly Leu Thr Ala
        755                 760                 765
Trp Leu Asn Ile Lys Lys Lys
```

```
                                    770                 775

<210> SEQ ID NO 26
<211> LENGTH: 775
<212> TYPE: PRT
<213> ORGANISM: Artificial Sequence
<220> FEATURE:
<223> OTHER INFORMATION: Description of Artificial Sequence:designed
      hybrid polymerase
<220> FEATURE:
<221> NAME/KEY: MOD_RES
<222> LOCATION: (1)..(775)
<223> OTHER INFORMATION: Xaa = unknown amino acid

<400> SEQUENCE: 26

Met Ile Leu Asp Xaa Asp Tyr Ile Thr Glu Xaa Gly Lys Pro Xaa Ile
  1               5                  10                  15

Arg Xaa Phe Lys Lys Glu Asn Gly Xaa Phe Lys Xaa Glu Xaa Asp Arg
                 20                  25                  30

Xaa Phe Arg Pro Tyr Ile Tyr Ala Leu Leu Xaa Asp Asp Ser Xaa Ile
             35                  40                  45

Xaa Glu Val Xaa Lys Ile Thr Xaa Glu Arg His Gly Lys Ile Val Arg
     50                  55                  60

Ile Xaa Asp Xaa Glu Lys Val Xaa Lys Lys Phe Leu Gly Xaa Pro Ile
 65                  70                  75                  80

Xaa Val Trp Xaa Leu Tyr Glu His Pro Gln Asp Val Pro Xaa Ile
                 85                  90                  95

Arg Xaa Lys Xaa Arg Glu His Xaa Ala Val Xaa Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Xaa Glu Glu Leu Lys Xaa Leu Ala Phe Asp Ile Glu Thr
130                 135                 140

Leu Tyr His Glu Gly Glu Glu Phe Xaa Lys Gly Pro Ile Ile Met Ile
145                 150                 155                 160

Ser Tyr Ala Asp Glu Xaa Glu Ala Lys Val Ile Thr Trp Lys Xaa Ile
                165                 170                 175

Asp Leu Pro Tyr Val Glu Val Ser Ser Glu Arg Glu Met Ile Lys
            180                 185                 190

Arg Phe Leu Xaa Xaa Ile Arg Glu Lys Asp Pro Asp Xaa Ile Xaa Thr
            195                 200                 205

Tyr Asn Gly Asp Ser Phe Asp Xaa Pro Tyr Leu Xaa Lys Arg Ala Glu
        210                 215                 220

Lys Leu Gly Ile Lys Leu Xaa Xaa Gly Arg Asp Gly Ser Glu Pro Lys
225                 230                 235                 240

Met Gln Arg Xaa Gly Asp Met Thr Ala Val Glu Xaa Lys Gly Arg Ile
                245                 250                 255

His Phe Asp Leu Tyr His Val Ile Xaa Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Xaa Glu Ile Ala Xaa Ala Trp Glu Xaa Gly Xaa Xaa
    290                 295                 300

Leu Glu Arg Val Ala Lys Tyr Ser Met Glu Asp Ala Lys Xaa Thr Tyr
305                 310                 315                 320

Glu Leu Gly Xaa Glu Phe Xaa Pro Met Glu Xaa Gln Leu Ser Arg Leu
                325                 330                 335
```

-continued

```
Val Gly Gln Pro Leu Trp Asp Val Ser Arg Ser Thr Gly Asn Leu
            340                 345                 350

Val Glu Trp Xaa Leu Leu Arg Lys Ala Tyr Glu Arg Asn Glu Xaa Ala
            355                 360                 365

Pro Asn Lys Pro Xaa Glu Xaa Glu Tyr Xaa Arg Arg Leu Arg Glu Ser
370                 375                 380

Tyr Xaa Gly Gly Xaa Val Lys Glu Pro Glu Lys Gly Leu Trp Glu Xaa
385                 390                 395                 400

Xaa Val Xaa Leu Asp Phe Arg Xaa Leu Tyr Pro Ser Ile Ile Ile Thr
                405                 410                 415

His Asn Val Ser Pro Asp Thr Leu Asn Xaa Glu Gly Cys Xaa Xaa Tyr
            420                 425                 430

Asp Xaa Ala Pro Xaa Val Gly His Lys Phe Cys Lys Asp Xaa Pro Gly
            435                 440                 445

Phe Ile Pro Ser Leu Leu Xaa Xaa Leu Leu Xaa Glu Arg Gln Xaa Ile
450                 455                 460

Lys Xaa Lys Met Lys Xaa Xaa Xaa Asp Pro Ile Glu Lys Xaa Xaa Leu
465                 470                 475                 480

Asp Tyr Arg Gln Xaa Ala Ile Lys Xaa Leu Ala Asn Ser Xaa Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Xaa Tyr Ile Glu Xaa Val Xaa Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Xaa Xaa Xaa Glu Gly Ile Lys Lys Lys
545                 550                 555                 560

Ala Leu Glu Phe Val Lys Tyr Ile Asn Xaa Lys Leu Pro Gly Leu Leu
            565                 570                 575

Glu Leu Glu Tyr Glu Gly Phe Tyr Xaa Arg Gly Phe Phe Val Thr Lys
            580                 585                 590

Lys Xaa Tyr Ala Xaa Ile Asp Glu Glu Gly Lys Xaa Ile Thr Arg Gly
            595                 600                 605

Leu Glu Ile Val Arg Arg Asp Trp Ser Glu Ile Ala Lys Glu Thr Gln
            610                 615                 620

Ala Xaa Val Leu Glu Xaa Ile Leu Lys His Gly Xaa Val Glu Glu Ala
625                 630                 635                 640

Val Xaa Ile Val Lys Glu Val Xaa Xaa Lys Leu Xaa Xaa Tyr Glu Ile
            645                 650                 655

Pro Pro Glu Lys Leu Xaa Ile Tyr Glu Gln Ile Thr Arg Pro Leu His
            660                 665                 670

Glu Tyr Lys Ala Ile Gly Pro His Val Ala Val Ala Lys Xaa Leu Ala
            675                 680                 685

Ala Xaa Gly Val Lys Xaa Xaa Pro Gly Met Val Ile Gly Tyr Ile Val
            690                 695                 700

Leu Arg Gly Asp Gly Pro Ile Ser Xaa Arg Ala Ile Leu Ala Glu Glu
705                 710                 715                 720

Xaa Asp Xaa Xaa Lys His Lys Tyr Asp Ala Glu Tyr Tyr Ile Glu Asn
                725                 730                 735

Gln Val Leu Pro Ala Val Leu Arg Ile Leu Glu Xaa Phe Gly Tyr Arg
            740                 745                 750
```

```
Lys Glu Asp Leu Arg Xaa Gln Lys Thr Xaa Gln Xaa Gly Leu Thr Xaa
            755                 760                 765

Trp Leu Asn Ile Lys Lys Ser
    770                 775

<210> SEQ ID NO 27
<211> LENGTH: 783
<212> TYPE: PRT
<213> ORGANISM: Artificial Sequence
<220> FEATURE:
<223> OTHER INFORMATION: Description of Artificial Sequence:designed
      hybrid polymerase from Figure 1
<220> FEATURE:
<221> NAME/KEY: MOD_RES
<222> LOCATION: (1)..(783)
<223> OTHER INFORMATION: Xaa = unknown amino acid

<400> SEQUENCE: 27

Met Ile Leu Asp Xaa Asp Tyr Ile Thr Glu Xaa Gly Lys Pro Xaa Ile
  1               5                  10                  15

Arg Xaa Phe Lys Lys Glu Asn Gly Xaa Phe Lys Xaa Glu Xaa Asp Arg
                 20                  25                  30

Xaa Phe Arg Pro Tyr Ile Tyr Ala Leu Leu Xaa Asp Asp Ser Xaa Ile
             35                  40                  45

Xaa Glu Val Xaa Lys Ile Thr Xaa Glu Arg His Gly Lys Ile Val Arg
         50                  55                  60

Ile Xaa Asp Xaa Glu Lys Val Xaa Lys Lys Phe Leu Gly Xaa Pro Ile
 65                  70                  75                  80

Xaa Val Trp Xaa Leu Tyr Xaa Glu His Pro Gln Asp Val Pro Xaa Ile
                 85                  90                  95

Arg Xaa Lys Xaa Arg Glu His Xaa Ala Val Xaa Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Xaa Glu Glu Leu Lys Xaa Leu Ala Phe Asp Ile Glu Thr
        130                 135                 140

Leu Tyr His Glu Gly Glu Glu Phe Xaa Lys Gly Pro Ile Ile Met Ile
145                 150                 155                 160

Ser Tyr Ala Asp Glu Xaa Glu Ala Lys Val Ile Thr Trp Lys Xaa Ile
                165                 170                 175

Asp Leu Pro Tyr Val Glu Val Val Ser Ser Glu Arg Glu Met Ile Lys
            180                 185                 190

Arg Phe Leu Xaa Xaa Ile Arg Glu Lys Asp Pro Asp Xaa Ile Xaa Thr
        195                 200                 205

Tyr Asn Gly Asp Ser Phe Asp Xaa Pro Tyr Leu Xaa Lys Arg Ala Glu
    210                 215                 220

Lys Leu Gly Ile Lys Leu Xaa Xaa Gly Arg Asp Gly Ser Glu Pro Lys
225                 230                 235                 240

Met Gln Arg Xaa Gly Asp Met Thr Ala Val Glu Xaa Lys Gly Arg Ile
                245                 250                 255

His Phe Asp Leu Tyr His Val Ile Xaa Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Xaa Glu Ile Ala Xaa Ala Trp Glu Xaa Gly Xaa Xaa
    290                 295                 300

Leu Glu Arg Val Ala Lys Tyr Ser Met Glu Asp Ala Lys Xaa Thr Tyr
```

-continued

```
            305                 310                 315                 320
        Glu Leu Gly Xaa Glu Phe Xaa Pro Met Glu Xaa Gln Leu Ser Arg Leu
                        325                 330                 335

Val Gly Gln Pro Leu Trp Asp Val Ser Arg Ser Ser Thr Gly Asn Leu
                        340                 345                 350

Val Glu Trp Xaa Leu Leu Arg Lys Ala Tyr Glu Arg Asn Glu Xaa Ala
                        355                 360                 365

Pro Asn Lys Pro Xaa Glu Xaa Glu Tyr Xaa Arg Arg Leu Arg Glu Ser
                        370                 375                 380

Tyr Xaa Gly Gly Xaa Val Lys Glu Pro Glu Lys Gly Leu Trp Glu Xaa
        385                 390                 395                 400

Xaa Val Xaa Leu Asp Phe Arg Xaa Leu Tyr Pro Ser Ile Ile Ile Thr
                        405                 410                 415

His Asn Val Ser Pro Asp Thr Leu Asn Xaa Glu Gly Cys Xaa Xaa Tyr
                        420                 425                 430

Asp Xaa Ala Pro Xaa Val Gly His Lys Phe Cys Lys Asp Xaa Pro Gly
                        435                 440                 445

Phe Ile Pro Ser Leu Leu Xaa Xaa Leu Leu Xaa Glu Arg Gln Xaa Ile
                        450                 455                 460

Lys Xaa Lys Met Lys Xaa Xaa Xaa Asp Pro Ile Glu Lys Xaa Xaa Leu
        465                 470                 475                 480

Asp Tyr Arg Gln Xaa Ala Ile Lys Xaa Leu Ala Asn Ser Xaa Tyr Gly
                        485                 490                 495

Tyr Tyr Gly Tyr Ala Lys Ala Arg Trp Tyr Cys Lys Glu Cys Ala Glu
                        500                 505                 510

Ser Val Thr Ala Trp Gly Arg Xaa Tyr Ile Glu Xaa Val Xaa Lys Glu
                        515                 520                 525

Leu Glu Glu Lys Phe Gly Phe Lys Val Leu Tyr Ile Asp Thr Asp Gly
                        530                 535                 540

Leu Tyr Ala Thr Ile Pro Gly Xaa Xaa Xaa Glu Ile Lys Lys Lys
        545                 550                 555                 560

Ala Leu Glu Phe Val Lys Tyr Ile Asn Xaa Lys Leu Pro Gly Leu Leu
                        565                 570                 575

Glu Leu Glu Tyr Glu Gly Phe Tyr Xaa Arg Gly Phe Phe Val Thr Lys
                        580                 585                 590

Lys Xaa Tyr Ala Xaa Ile Asp Glu Glu Gly Lys Xaa Ile Thr Arg Gly
                        595                 600                 605

Leu Glu Ile Val Arg Arg Asp Trp Ser Glu Ile Ala Lys Glu Thr Gln
                        610                 615                 620

Ala Xaa Val Leu Glu Xaa Ile Leu Lys His Gly Xaa Val Glu Glu Ala
        625                 630                 635                 640

Val Xaa Ile Val Lys Glu Val Xaa Xaa Lys Leu Xaa Xaa Tyr Glu Ile
                        645                 650                 655

Pro Pro Glu Lys Leu Xaa Ile Tyr Glu Gln Ile Thr Arg Pro Leu His
                        660                 665                 670

Glu Tyr Lys Ala Ile Gly Pro His Val Ala Val Ala Lys Xaa Leu Ala
                        675                 680                 685

Ala Xaa Gly Val Lys Xaa Xaa Pro Gly Met Val Ile Gly Tyr Ile Val
                        690                 695                 700

Leu Arg Gly Asp Gly Pro Ile Ser Xaa Arg Ala Ile Leu Ala Glu Glu
        705                 710                 715                 720

Xaa Asp Xaa Xaa Lys His Lys Tyr Asp Ala Glu Tyr Tyr Ile Glu Asn
                        725                 730                 735
```

-continued

Gln Val Leu Pro Ala Val Leu Arg Ile Leu Glu Xaa Phe Gly Tyr Arg
            740                 745                 750

Lys Glu Asp Leu Arg Xaa Gln Lys Thr Xaa Gln Xaa Gly Leu Thr Xaa
        755                 760                 765

Trp Leu Asn Ile Lys Lys Ser Gly Thr His Asn Cys Asn His Asp
    770                 775                 780

<210> SEQ ID NO 28
<211> LENGTH: 845
<212> TYPE: PRT
<213> ORGANISM: Artificial Sequence
<220> FEATURE:
<223> OTHER INFORMATION: Description of Artificial Sequence:hybrid
      polymerase HyS1 from Figure 5
<220> FEATURE:
<221> NAME/KEY: MOD_RES
<222> LOCATION: (472)
<223> OTHER INFORMATION: Xaa = unknown amino acid

<400> SEQUENCE: 28

Met Ile Leu Asp Ala Asp Tyr Ile Thr Glu Asp Gly Lys Pro Val Ile
  1               5                  10                  15

Arg Leu Phe Lys Lys Glu Asn Gly Glu Phe Lys Ile Glu Tyr Asp Arg
             20                  25                  30

Thr Phe Arg Pro Tyr Ile Tyr Ala Leu Leu Arg Asp Asp Ser Lys Ile
         35                  40                  45

Glu Glu Val Arg Lys Ile Thr Ala Glu Arg His Gly Lys Ile Val Arg
     50                  55                  60

Ile Val Asp Val Glu Lys Val Arg Lys Lys Phe Leu Gly Arg Pro Ile
 65                  70                  75                  80

Lys Val Trp Arg Leu Tyr Phe Glu His Pro Gln Asp Val Pro Thr Ile
                 85                  90                  95

Arg Asp Lys Val Arg Glu His Pro Ala Val Ile Asp Ile Phe Glu Tyr
            100                 105                 110

Asp Ile Ala Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Gly Ser Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Leu Pro Tyr Leu Ala Lys Arg Ala Glu
    210                 215                 220

Lys Leu Gly Ile Lys Leu Thr Leu Gly Arg Asp Gly Cys Glu Ala Lys
225                 230                 235                 240

Met Gln Arg Leu Gly Asp Met Thr Ala Val Glu Val Lys Gly Arg Ile
                245                 250                 255

His Phe Asp Leu Tyr Tyr Val Ile Ser Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

-continued

```
Lys Val Tyr Ala Asp Asp Ile Ala Glu Ala Trp Glu Thr Gly Lys Gly
            290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Val Ala
        355                 360                 365

Pro Asn Lys Pro Tyr Glu Arg Glu Tyr Glu Arg Arg Leu Arg Glu Ser
370                 375                 380

Tyr Thr Gly Gly Phe Val Lys Glu Pro Glu Lys Gly Leu Trp Glu Ser
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Lys Asp Tyr
            420                 425                 430

Asp Ile Ala Pro Glu Val Gly His Lys Phe Cys Lys Asp Phe Leu Gly
        435                 440                 445

Phe Ile Pro Ser Leu Leu Gly His Leu Leu Glu Glu Arg Gln Glu Ile
450                 455                 460

Lys Thr Lys Met Lys Glu Thr Xaa Asp Pro Ile Glu Lys Ile Leu Leu
465                 470                 475                 480

Asp Tyr Arg Gln Lys Ala Ile Lys Leu Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Glu Pro Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
610                 615                 620

Ala Lys Val Leu Glu Ala Ile Leu Lys His Gly Asn Val Glu Glu Ala
625                 630                 635                 640

Val Lys Ile Val Lys Glu Ile Ile Glu Lys Leu Ala Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Arg Gly Val Lys Ile Lys Pro Gly Met Val Ile Gly Tyr Ile Val
690                 695                 700

Leu Arg Gly Asp Gly Pro Ile Ser Lys Arg Ala Ile Leu Ala Glu Glu
```

-continued

```
                705                 710                 715                 720
Phe Asp Pro Lys Lys His Lys Tyr Asp Ala Glu Tyr Tyr Ile Glu Asn
                    725                 730                 735
Gln Val Leu Pro Ala Val Leu Arg Ile Leu Glu Gly Phe Gly Tyr Arg
                740                 745                 750
Lys Glu Asp Leu Arg Trp Gln Lys Thr Lys Gln Ala Gly Leu Thr Ala
                755                 760                 765
Trp Leu Asn Ile Lys Lys Ser Gly Thr Gly Gly Gly Ala Thr Val
                770                 775                 780
Lys Phe Lys Tyr Lys Gly Glu Glu Lys Glu Val Asp Ile Ser Lys Ile
785                 790                 795                 800
Lys Lys Val Trp Arg Val Gly Lys Met Ile Ser Phe Thr Tyr Asp Glu
                805                 810                 815
Gly Gly Gly Lys Thr Gly Arg Gly Ala Val Ser Glu Lys Asp Ala Pro
                820                 825                 830
Lys Glu Leu Leu Gln Met Leu Glu Lys Gln Lys Lys Asn
                835                 840                 845

<210> SEQ ID NO 29
<211> LENGTH: 758
<212> TYPE: PRT
<213> ORGANISM: Artificial Sequence
<220> FEATURE:
<223> OTHER INFORMATION: Description of Artificial Sequence:hybrid
      polymerase Hyb2 from Figure 5
<220> FEATURE:
<221> NAME/KEY: MOD_RES
<222> LOCATION: (472)
<223> OTHER INFORMATION: Xaa = unknown amino acid

<400> SEQUENCE: 29

Met Ile Leu Asp Ala Asp Tyr Ile Thr Glu Glu Gly Lys Pro Val Ile
1               5                   10                  15
Arg Ile Phe Lys Lys Glu Asn Gly Glu Phe Lys Val Glu Tyr Asp Arg
                20                  25                  30
Asn Phe Arg Pro Tyr Ile Tyr Ala Leu Leu Glu Asp Asp Ser Lys Ile
            35                  40                  45
Asp Glu Val Arg Lys Ile Thr Ala Glu Arg His Gly Lys Ile Val Arg
        50                  55                  60
Ile Val Asp Ala Glu Lys Val Glu Lys Lys Phe Leu Gly Arg Pro Ile
65                  70                  75                  80
Thr Val Trp Lys Leu Tyr Phe Glu His Pro Gln Asp Val Pro Thr Ile
                85                  90                  95
Arg Glu Lys Ile Arg Glu His Ser Ala Val Val Gly Ile Phe Glu Tyr
                100                 105                 110
Asp Ile Pro Phe Ala Lys Ser Tyr Leu Ile Asp Lys Gly Leu Ile Pro
            115                 120                 125
Met Glu Gly Glu Glu Leu Lys Leu Leu Ala Phe Asp Ile Glu Thr
        130                 135                 140
Leu Tyr His Glu Gly Glu Glu Phe Ala Lys Gly Pro Ile Ile Met Ile
145                 150                 155                 160
Ser Tyr Ala Asp Glu Asp Glu Ala Lys Val Ile Thr Trp Lys Lys Ile
                165                 170                 175
Asp Leu Pro Tyr Val Glu Val Val Ser Ser Glu Arg Glu Met Ile Lys
            180                 185                 190
Arg Phe Leu Arg Val Ile Arg Glu Lys Asp Pro Asp Val Ile Val Thr
        195                 200                 205
```

-continued

```
Tyr Asn Gly Asp Ser Phe Asp Leu Pro Tyr Leu Ala Lys Arg Ala Glu
    210                 215                 220
Lys Leu Gly Ile Lys Leu Pro Leu Gly Arg Asp Gly Ser Glu Pro Lys
225                 230                 235                 240
Met Gln Arg Leu Gly Asp Met Thr Ala Val Glu Val Lys Gly Arg Ile
                245                 250                 255
His Phe Asp Leu Tyr His Val Ile Ser Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Gly Ala Trp Glu Thr Gly Glu Asp
    290                 295                 300
Leu Glu Arg Val Ala Lys Tyr Ser Met Glu Asp Ala Lys Ala Ile Tyr
305                 310                 315                 320
Glu Leu Gly Lys Glu Phe Phe Pro Met Glu Val Gln Leu Pro Arg Leu
                325                 330                 335
Val Gly Gln Pro Leu Trp Asp Val Ser Arg Ser Thr Gly Asn Leu
            340                 345                 350
Val Glu Trp Leu Leu Leu Arg Lys Ala Tyr Glu Arg Asn Glu Leu Ala
        355                 360                 365
Pro Asn Lys Pro Ala Glu Gln Glu Tyr Glu Arg Arg Leu Arg Glu Ser
    370                 375                 380
Tyr Thr Gly Gly Phe Val Lys Glu Pro Glu Lys Gly Leu Trp Glu Asp
385                 390                 395                 400
Leu Val Ser Leu Asp Phe Arg Ala Leu Tyr Pro Ser Ile Ile Ile Thr
                405                 410                 415
His Asn Val Ser Pro Asp Thr Leu Asn Arg Glu Gly Cys Lys Asp Tyr
            420                 425                 430
Asp Ile Ala Pro Glu Val Gly His Lys Phe Cys Lys Asp Phe Leu Gly
        435                 440                 445
Phe Ile Pro Ser Leu Leu Gly His Leu Leu Glu Glu Arg Gln Glu Ile
    450                 455                 460
Lys Thr Lys Met Lys Glu Thr Xaa Asp Pro Ile Glu Lys Ile Leu Leu
465                 470                 475                 480
Asp Tyr Arg Gln Lys Ala Ile Lys Leu Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Phe Val Trp Lys Glu
        515                 520                 525
Leu Glu Glu Lys Phe Gly Phe Lys Val Leu Tyr Ile Asp Thr Asp Gly
    530                 535                 540
Leu Tyr Ala Thr Ile Pro Gly Gly Glu Pro Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Arg Tyr Ala Val Ile Asp Glu Glu Gly Lys Ile Ile Thr Arg Gly
        595                 600                 605
Leu Glu Ile Val Arg Arg Asp Trp Ser Glu Ile Ala Lys Glu Thr Gln
    610                 615                 620
```

-continued

```
Ala Lys Val Leu Glu Ala Ile Leu Lys His Gly Asn Val Glu Glu Ala
625                 630                 635                 640

Val Lys Ile Val Lys Glu Ile Ile Glu Lys Leu Ala Lys Tyr Glu Ile
            645                 650                 655

Pro Pro Glu Lys Leu Ala Ile Tyr Glu Gln Ile Thr Arg Pro Leu His
        660                 665                 670

Glu Tyr Lys Ala Ile Gly Pro His Val Ala Val Ala Lys Lys Leu Ala
    675                 680                 685

Ala Arg Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Asn
        755

<210> SEQ ID NO 30
<211> LENGTH: 758
<212> TYPE: PRT
<213> ORGANISM: Artificial Sequence
<220> FEATURE:
<223> OTHER INFORMATION: Description of Artificial Sequence:hybrid
      polymerase Hyb3 from Figure 5
<220> FEATURE:
<221> NAME/KEY: MOD_RES
<222> LOCATION: (472)
<223> OTHER INFORMATION: Xaa = unknown amino acid

<400> SEQUENCE: 30

Met Ile Leu Asp Ala Asp Tyr Ile Thr Glu Glu Gly Lys Pro Val Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Glu Asp Asp Ser Lys Ile
        35                  40                  45

Asp Glu Val Arg Lys Ile Thr Ala Glu Arg His Gly Lys Ile Val Arg
    50                  55                  60

Ile Val Asp Ala Glu Lys Val Glu Lys Lys Phe Leu Gly Arg Pro Ile
65                  70                  75                  80

Thr Val Trp Lys Leu Tyr Phe Glu His Pro Gln Asp Val Pro Thr Ile
                85                  90                  95

Arg Glu Lys Ile Arg Glu His Ser Ala Val Val Gly Ile Phe Glu Tyr
            100                 105                 110

Asp Ile Pro Phe Ala Lys Ser Tyr Leu Ile Asp Lys Gly Leu Ile Pro
        115                 120                 125

Met Glu Gly Glu Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Asp Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Arg Val Ile Arg Glu Lys Asp Pro Asp Val Ile Val Thr
```

-continued

```
            195                 200                 205
Tyr Asn Gly Asp Ser Phe Asp Leu Pro Tyr Leu Ala Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Val Lys Gly Arg Ile
                245                 250                 255

His Phe Asp Leu Tyr His Val Ile Ser Arg Thr Ile Asn Leu Pro Thr
                260                 265                 270

Tyr Thr Leu Glu Ala Val Tyr Glu Ala Ile Phe Gly Lys Pro Lys Glu
            275                 280                 285

Lys Val Tyr Ala Asp Glu Ile Ala Gly Ala Trp Glu Thr Gly Glu Asp
    290                 295                 300

Leu Glu Arg Val Ala Lys Tyr Ser Met Glu Asp Ala Lys Ala Ile Tyr
305                 310                 315                 320

Glu Leu Gly Lys Glu Phe Phe Pro Met Glu Val Gln Leu Pro Arg Leu
                325                 330                 335

Val Gly Gln Pro Leu Trp Asp Val Ser Arg Ser Ser Thr Gly Asn Leu
                340                 345                 350

Val Glu Trp Leu Leu Leu Arg Lys Ala Tyr Glu Arg Asn Glu Leu Ala
            355                 360                 365

Pro Asn Lys Pro Ala Glu Gln Glu Tyr Glu Arg Arg Leu Arg Glu Ser
    370                 375                 380

Tyr Thr Gly Gly Phe Val Lys Glu Pro Glu Lys Gly Leu Trp Glu Asp
385                 390                 395                 400

Leu Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Lys Asp Tyr
                420                 425                 430

Asp Ile Ala Pro Glu Val Gly His Lys Phe Cys Lys Asp Phe Leu Gly
            435                 440                 445

Phe Ile Pro Ser Leu Leu Gly His Leu Leu Glu Glu Arg Gln Glu Ile
    450                 455                 460

Lys Thr Lys Met Lys Glu Thr Xaa Asp Pro Ile Glu Lys Ile Leu Leu
465                 470                 475                 480

Asp Tyr Arg Gln Lys Ala Ile Lys Leu Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
    515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Glu Pro Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Ile Ile Thr Arg Gly
    595                 600                 605

Leu Glu Ile Val Arg Arg Asp Trp Ser Glu Ile Ala Lys Glu Thr Gln
610                 615                 620
```

```
Ala Lys Val Leu Glu Ala Ile Leu Lys His Gly Asn Val Glu Glu Ala
625                 630                 635                 640

Val Lys Ile Val Lys Glu Ile Ile Glu Lys Leu Ala Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Arg Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Asn
        755

<210> SEQ ID NO 31
<211> LENGTH: 845
<212> TYPE: PRT
<213> ORGANISM: Artificial Sequence
<220> FEATURE:
<223> OTHER INFORMATION: Description of Artificial Sequence:hybrid
      polymerase HyS4 from Figure 5
<220> FEATURE:
<221> NAME/KEY: MOD_RES
<222> LOCATION: (472)
<223> OTHER INFORMATION: Xaa = unknown amino acid

<400> SEQUENCE: 31

Met Ile Leu Asp Ala Asp Tyr Ile Thr Glu Glu Gly Lys Pro Val Ile
  1               5                  10                  15

Arg Ile Phe Lys Lys Glu Asn Gly Glu Phe Lys Val Glu Tyr Asp Arg
                20                  25                  30

Asn Phe Arg Pro Tyr Ile Tyr Ala Leu Leu Glu Asp Asp Ser Lys Ile
            35                  40                  45

Asp Glu Val Arg Lys Ile Thr Ala Glu Arg His Gly Lys Ile Val Arg
        50                  55                  60

Ile Val Asp Ala Glu Lys Val Glu Lys Lys Phe Leu Gly Arg Pro Ile
65                  70                  75                  80

Thr Val Trp Lys Leu Tyr Phe Glu His Pro Gln Asp Val Pro Thr Ile
                85                  90                  95

Arg Glu Lys Ile Arg Glu His Ser Ala Val Val Gly Ile Phe Glu Tyr
               100                 105                 110

Asp Ile Pro Phe Ala Lys Ser Tyr Leu Ile Asp Lys Gly Leu Ile Pro
           115                 120                 125

Met Glu Gly Glu Glu Glu Leu Lys Leu Leu Ala Phe Asp Ile Glu Thr
       130                 135                 140

Leu Tyr His Glu Gly Glu Glu Phe Ala Lys Gly Pro Ile Ile Met Ile
145                 150                 155                 160

Ser Tyr Ala Asp Glu Asp Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190
```

```
Arg Phe Leu Arg Val Ile Arg Glu Lys Asp Pro Asp Val Ile Val Thr
            195                 200                 205

Tyr Asn Gly Asp Ser Phe Asp Leu Pro Tyr Leu Ala Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Val Lys Gly Arg Ile
                245                 250                 255

His Phe Asp Leu Tyr His Val Ile Ser Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Gly Ala Trp Glu Thr Gly Glu Asp
290                 295                 300

Leu Glu Arg Val Ala Lys Tyr Ser Met Glu Asp Ala Lys Ala Ile Tyr
305                 310                 315                 320

Glu Leu Gly Lys Glu Phe Phe Pro Met Glu Val Gln Leu Pro Arg Leu
                325                 330                 335

Val Gly Gln Pro Leu Trp Asp Val Ser Arg Ser Thr Gly Asn Leu
            340                 345                 350

Val Glu Trp Leu Leu Leu Arg Lys Ala Tyr Glu Arg Asn Glu Leu Ala
        355                 360                 365

Pro Asn Lys Pro Ala Glu Gln Glu Tyr Glu Arg Arg Leu Arg Glu Ser
    370                 375                 380

Tyr Thr Gly Gly Phe Val Lys Glu Pro Glu Lys Gly Leu Trp Glu Asp
385                 390                 395                 400

Leu Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Lys Asp Tyr
            420                 425                 430

Asp Ile Ala Pro Glu Val Gly His Lys Phe Cys Lys Asp Phe Leu Gly
        435                 440                 445

Phe Ile Pro Ser Leu Leu Gly His Leu Leu Glu Glu Arg Gln Glu Ile
    450                 455                 460

Lys Thr Lys Met Lys Glu Thr Xaa Asp Pro Ile Glu Lys Ile Leu Leu
465                 470                 475                 480

Asp Tyr Arg Gln Lys Ala Ile Lys Leu Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Pro Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
```

```
                 610                 615                 620
Ala Lys Val Leu Glu Ala Ile Leu Lys His Gly Asn Val Glu Glu Ala
625                 630                 635                 640

Val Lys Ile Val Lys Glu Ile Ile Glu Lys Leu Ala Lys Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
                675                 680                 685

Ala Arg Gly Val Lys Ile Lys Pro Gly Met Val Ile Gly Tyr Ile Val
690                 695                 700

Leu Arg Gly Asp Gly Pro Ile Ser Lys Arg Ala Ile Leu Ala Glu Glu
705                 710                 715                 720

Phe Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
                740                 745                 750

Lys Glu Asp Leu Arg Trp Gln Lys Thr Lys Gln Ala Gly Leu Thr Ala
                755                 760                 765

Trp Leu Asn Ile Lys Lys Ser Gly Thr Gly Gly Gly Ala Thr Val
770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
                820                 825                 830

Lys Glu Leu Leu Gln Met Leu Glu Lys Gln Lys Lys Asn
                835                 840                 845

<210> SEQ ID NO 32
<211> LENGTH: 845
<212> TYPE: PRT
<213> ORGANISM: Artificial Sequence
<220> FEATURE:
<223> OTHER INFORMATION: Description of Artificial Sequence:hybrid
      polymerase PhS1 from Figure 5

<400> SEQUENCE: 32

Met Ile Leu Asp Ala Asp Tyr Ile Thr Glu Glu Gly Lys Pro Val Ile
1               5                   10                  15

Arg Leu Phe Lys Lys Glu Asn Gly Glu Phe Lys Ile Glu His Asp Arg
                20                  25                  30

Thr Phe Arg Pro Tyr Ile Tyr Ala Leu Leu Lys Asp Asp Ser Lys Ile
            35                  40                  45

Glu Glu Val Lys Lys Ile Thr Ala Glu Arg His Gly Lys Ile Val Arg
        50                  55                  60

Ile Val Asp Ala Glu Lys Val Glu Lys Lys Phe Leu Gly Arg Pro Ile
65              70                  75                  80

Thr Val Trp Arg Leu Tyr Phe Glu His Pro Gln Asp Val Pro Thr Ile
                85                  90                  95

Arg Glu Lys Ile Arg Glu His Ser Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125
```

-continued

```
Met Glu Gly Asp Glu Glu Leu Lys Leu Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Ala Lys Val Ile Thr Trp Lys Lys Ile
                165                 170                 175

Asp Leu Pro Tyr Val Glu Val Ser Ser Glu Arg Glu Met Ile Lys
            180                 185                 190

Arg Phe Leu Lys Ile Ile Arg Glu Lys Asp Pro Asp Ile Ile Ile Thr
            195                 200                 205

Tyr Asn Gly Asp Ser Phe Asp Leu Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
    275                 280                 285

Lys Val Tyr Ala Asp Glu Ile Ala Lys Ala Trp Glu Thr Gly Glu Gly
    290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Phe Val Lys Glu Pro Glu Lys Gly Leu Trp Glu Asn
385                 390                 395                 400

Ile Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Arg Asn Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Lys Ile
    450                 455                 460

Lys Thr Lys Met Lys Ala Ser Gln Asp Pro Ile Glu Lys Ile Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Lys Ser Glu Glu Ile Lys Lys Lys
```

-continued

```
              545                 550                 555                 560
Ala Leu Glu Phe Val Asp Tyr Ile Asn Ala Lys Leu Pro Gly Leu Leu
                565                 570                 575

Glu Leu Glu Tyr Glu Gly Phe Tyr Lys Arg Gly Phe Phe Val Thr Lys
                580                 585                 590

Lys Lys Tyr Ala Leu Ile Asp Glu Glu Gly Lys Ile Ile Thr Arg Gly
                595                 600                 605

Leu Glu Ile Val Arg Arg Asp Trp Ser Glu Ile Ala Lys Glu Thr Gln
                610                 615                 620

Ala Arg Val Leu Glu Ala Ile Leu Lys His Gly Asn Val Glu Glu Ala
625                 630                 635                 640

Val Arg Ile Val Lys Glu Val Thr Gln Lys Leu Ser Lys Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Arg Leu Ala
                675                 680                 685

Ala Lys Gly Val Lys Ile Lys Pro Gly Met Val Ile Gly Tyr Ile Val
                690                 695                 700

Leu Arg Gly Asp Gly Pro Ile Ser Asn Arg Ala Ile Leu Ala Glu Glu
705                 710                 715                 720

Tyr Asp Pro Arg Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
                740                 745                 750

Lys Glu Asp Leu Arg Trp Gln Lys Thr Lys Gln Thr Gly Leu Thr Ser
                755                 760                 765

Trp Leu Asn Ile Lys Lys Ser Gly Thr Gly Gly Gly Ala Thr Val
                770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
                820                 825                 830

Lys Glu Leu Leu Gln Met Leu Glu Lys Gln Lys Lys Asn
                835                 840                 845
```

<210> SEQ ID NO 33
<211> LENGTH: 845
<212> TYPE: PRT
<213> ORGANISM: Artificial Sequence
<220> FEATURE:
<223> OTHER INFORMATION: Description of Artificial Sequence:hybrid polymerase PhS2 from Figure 5

<400> SEQUENCE: 33

```
Met Ile Leu Asp Val Asp Tyr Ile Thr Glu Glu Gly Lys Pro Val Ile
1               5                   10                  15

Arg Leu Phe Lys Lys Glu Asn Gly Glu Phe Lys Val Glu Tyr Asp Arg
                20                  25                  30

Thr Phe Arg Pro Tyr Ile Tyr Ala Leu Leu Lys Asp Asp Ser Lys Ile
                35                  40                  45

Asp Glu Val Arg Lys Ile Thr Gly Glu Arg His Gly Lys Ile Val Arg
        50                  55                  60
```

-continued

```
Ile Ile Asp Ala Glu Lys Val Arg Lys Phe Leu Gly Lys Pro Ile
 65                  70                  75                  80

Glu Val Trp Lys Leu Tyr Phe Glu His Pro Gln Asp Val Pro Thr Ile
                 85                  90                  95

Arg Glu Lys Ile Arg Glu His Ser Ala Val Val Asp Ile Phe Glu Tyr
                100                 105                 110

Asp Ile Pro Phe Ala Lys Arg Tyr Leu Ile Asp Lys Gly Leu Ile Pro
                115                 120                 125

Met Glu Gly Glu Glu Leu Lys Ile Leu Ala Phe Asp Ile Glu Thr
                130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Lys Ile
                165                 170                 175

Asp Leu Pro Tyr Val Glu Val Val Ser Ser Glu Arg Glu Met Ile Lys
                180                 185                 190

Arg Phe Leu Lys Val Ile Arg Glu Lys Asp Pro Asp Ile Ile Val Thr
                195                 200                 205

Tyr Asn Gly Asp Ser Phe Asp Phe Pro Tyr Leu Ala Lys Arg Ala Glu
                210                 215                 220

Lys Leu Gly Ile Lys Leu Pro Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
                275                 280                 285

Lys Val Tyr Ala His Glu Ile Ala Glu Ala Trp Glu Ser Gly Glu Gly
                290                 295                 300

Leu Glu Arg Val Ala Lys Tyr Ser Met Glu Asp Ala Lys Ala Thr Tyr
305                 310                 315                 320

Glu Leu Gly Lys Glu Phe Phe Pro Met Glu Ile Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Ser Glu Arg Glu Tyr Glu Arg Arg Leu Arg Glu Ser
                370                 375                 380

Tyr Thr Gly Gly Tyr Val Lys Glu Pro Glu Lys Gly Leu Trp Glu Asn
385                 390                 395                 400

Ile Val Tyr Leu Asp Phe Arg Ser Leu Tyr Pro Ser Ile Ile Thr
                405                 410                 415

His Asn Val Ser Pro Asp Thr Leu Asn Leu Glu Gly Cys Lys Glu Tyr
                420                 425                 430

Asp Val Ala Pro Glu Val Gly His Lys Phe Cys Lys Asp Ile Pro Gly
                435                 440                 445

Phe Ile Pro Ser Leu Leu Gly His Leu Leu Glu Glu Arg Gln Lys Ile
                450                 455                 460

Lys Arg Lys Met Lys Ala Ser Lys Asp Pro Ile Glu Lys Ile Leu Leu
465                 470                 475                 480

Asp Tyr Arg Gln Arg Ala Ile Lys Leu Leu Ala Asn Ser Phe Tyr Gly
```

```
                      485                 490                 495
Tyr Tyr Gly Tyr Ala Lys Ala Arg Trp Tyr Cys Lys Glu Cys Ala Glu
                500                 505                 510

Ser Val Thr Ala Trp Gly Arg Glu Tyr Ile Glu Leu Val Arg Lys Glu
            515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Lys Ser Glu Glu Ile Lys Lys Lys
545                 550                 555                 560

Ala Leu Glu Phe Val Asp Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
        610                 615                 620

Ala Lys Val Leu Glu Thr Ile Leu Lys His Gly Asn Val Glu Glu Ala
625                 630                 635                 640

Val Arg Ile Val Lys Glu Val Thr Gln Lys Leu Ala Lys Tyr Glu Ile
                645                 650                 655

Pro Pro Glu Lys Leu Ala Ile Tyr Glu Gln Ile Thr Pro Pro Leu His
            660                 665                 670

Glu Tyr Lys Ala Ile Gly Pro His Val Ala Val Ala Lys Arg Leu Ala
        675                 680                 685

Ala Arg Gly Val Lys Ile Lys Pro Gly Met Val Ile Gly Tyr Ile Val
        690                 695                 700

Leu Arg Gly Asp Gly Pro Ile Ser Asn Arg Ala Ile Leu Ala Glu Glu
705                 710                 715                 720

Tyr Asp Leu Lys Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Tyr Gln Lys Thr Lys Gln Val Asp Leu Thr Ala
        755                 760                 765

Cys Leu Asn Ile Lys Lys Ser Gly Thr Gly Gly Gly Ala Thr Val
770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys Asn
        835                 840                 845

<210> SEQ ID NO 34
<211> LENGTH: 145
<212> TYPE: PRT
<213> ORGANISM: Artificial Sequence
<220> FEATURE:
<223> OTHER INFORMATION: Description of Artificial Sequence:hybrid
      polymerase PhS3 from Figure 5

<400> SEQUENCE: 34
```

```
Met Ile Leu Asp Ala Asp Tyr Ile Thr Glu Glu Gly Lys Pro Ile Ile
 1               5                  10                  15

Arg Leu Phe Lys Lys Glu Asn Gly Lys Phe Lys Val Glu Tyr Asp Arg
                20                  25                  30

Thr Phe Arg Pro Tyr Ile Tyr Ala Leu Leu Lys Asp Asp Ser Lys Ile
            35                  40                  45

Asp Glu Val Arg Lys Ile Thr Gly Glu Arg His Gly Lys Ile Val Arg
        50                  55                  60

Ile Val Asp Ala Glu Lys Val Glu Lys Lys Phe Leu Gly Lys Pro Ile
65                  70                  75                  80

Glu Val Trp Lys Leu Tyr Leu Glu His Pro Gln Asp Val Pro Thr Ile
                85                  90                  95

Arg Glu Lys Ile Arg Glu His Ser Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Val Arg Tyr Arg Asn Pro Leu Ser Arg Arg Arg Arg Val
        130                 135                 140

Trp
145

<210> SEQ ID NO 35
<211> LENGTH: 844
<212> TYPE: PRT
<213> ORGANISM: Artificial Sequence
<220> FEATURE:
<223> OTHER INFORMATION: Description of Artificial Sequence:hybrid
      polymerase PhS4 from Figure 5

<400> SEQUENCE: 35

Met Ile Leu Asp Ala Asp Tyr Ile Thr Glu Glu Gly Lys Pro Val Ile
 1               5                  10                  15

Arg Leu Phe Lys Lys Glu Asn Gly Glu Phe Lys Val Glu Tyr Asp Arg
                20                  25                  30

Asn Phe Arg Pro Tyr Ile Tyr Ala Leu Leu Arg Asp Asp Ser Gln Ile
            35                  40                  45

Asp Glu Val Arg Lys Ile Thr Gly Glu Arg His Gly Lys Ile Val Arg
        50                  55                  60

Ile Val Asp Ala Glu Lys Val Glu Lys Lys Phe Leu Gly Arg Pro Ile
65                  70                  75                  80

Glu Val Trp Lys Leu Tyr Leu His Pro Gln Asp Val Pro Ala Ile
                85                  90                  95

Arg Glu Lys Val Arg Glu His Ser Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Glu Glu Leu Lys Leu Leu Ala Phe Asp Ile Glu Thr
        130                 135                 140

Leu Tyr His Glu Gly Glu Glu Phe Ala Lys Gly Pro Ile Ile Met Ile
145                 150                 155                 160

Ser Tyr Ala Asp Glu Asn Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Arg Val Ile Arg Glu Lys Asp Pro Asp Val Ile Val Thr
        195                 200                 205
```

-continued

Tyr Asn Gly Asp Ser Phe Asp Leu Pro Tyr Leu Val Lys Arg Ala Glu
    210                 215                 220

Lys Leu Gly Ile Lys Leu Pro Ile Gly Arg Asp Gly Ser Glu Pro Lys
225                 230                 235                 240

Met Gln Arg Ile Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Lys Ala Trp Glu Ser Gly Glu Gly
    290                 295                 300

Leu Glu Arg Val Ala Lys Tyr Ser Met Glu Asp Ala Lys Val Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Glu Arg Arg Leu Arg Glu Ser
    370                 375                 380

Tyr Ala Gly Gly Tyr Val Lys Glu Pro Glu Lys Gly Leu Trp Glu Asn
385                 390                 395                 400

Ile Val Ser Leu Asp Phe Arg Ser Leu Tyr Pro Ser Ile Ile Thr
                405                 410                 415

His Asn Val Ser Pro Asp Thr Leu Asn Arg Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Lys His Leu Leu Asp Glu Arg Gln Lys Ile
    450                 455                 460

Lys Arg Lys Met Lys Glu Ser Gln Asp Pro Ile Glu Lys Lys Met Leu
465                 470                 475                 480

Asp Tyr Arg Gln Arg Ala Ile Lys Leu Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Gly Leu
    530                 535                 540

Tyr Ala Thr Ile Pro Gly Ala Lys Ser Glu Glu Ile Lys Lys Lys Ala
545                 550                 555                 560

Leu Glu Phe Val Lys Tyr Ile Asn Ser Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Arg Tyr Ala Leu Ile Asp Glu Glu Gly Lys Ile Ile Thr Arg Gly Leu
        595                 600                 605

Glu Ile Val Arg Arg Asp Trp Ser Glu Ile Ala Lys Glu Thr Gln Ala
    610                 615                 620

```
Arg Val Leu Glu Thr Ile Leu Lys His Gly Asn Val Glu Glu Ala Val
625                 630                 635                 640

Arg Ile Val Lys Glu Val Thr Lys Lys Leu Ser Asn Tyr Glu Ile Pro
            645                 650                 655

Pro Glu Lys Leu Ala Ile Tyr Glu Gln Ile Thr Arg Pro Leu His Glu
        660                 665                 670

Tyr Lys Ala Ile Gly Pro His Val Ala Val Ala Lys Arg Leu Ala Ala
    675                 680                 685

Lys Gly Val Lys Ile Arg Pro Gly Met Val Ile Gly Tyr Ile Val Leu
690                 695                 700

Arg Gly Asp Gly Pro Ile Ser Asn Arg Ala Ile Leu Ala Glu Glu Tyr
705                 710                 715                 720

Asp Pro Lys Lys His Lys Tyr Asp Ala Glu Tyr Tyr Ile Glu Asn Gln
            725                 730                 735

Val Leu Pro Ala Val Leu Arg Ile Leu Glu Ala Phe Gly Tyr Arg Lys
        740                 745                 750

Glu Asp Leu Arg Trp Gln Lys Thr Lys Gln Val Gly Leu Thr Ala Trp
    755                 760                 765

Leu Asn Ile Lys Lys Ser Gly Thr Gly Gly Gly Ala Thr Val Lys
770                 775                 780

Phe Lys Tyr Lys Gly Glu Glu Lys Glu Val Asp Ile Ser Lys Ile Lys
785                 790                 795                 800

Lys Val Trp Arg Val Gly Lys Met Ile Ser Phe Thr Tyr Asp Glu Gly
            805                 810                 815

Gly Gly Lys Thr Gly Arg Gly Ala Val Ser Glu Lys Asp Ala Pro Lys
        820                 825                 830

Glu Leu Leu Gln Met Leu Glu Lys Gln Lys Asn
    835                 840

<210> SEQ ID NO 36
<211> LENGTH: 845
<212> TYPE: PRT
<213> ORGANISM: Artificial Sequence
<220> FEATURE:
<223> OTHER INFORMATION: Description of Artificial Sequence:hybrid
      polymerase PhS5 from Figure 5

<400> SEQUENCE: 36

Met Ile Leu Asp Ala Asp Tyr Ile Thr Glu Asp Gly Lys Pro Ile Ile
1               5                   10                  15

Arg Leu Phe Lys Lys Glu Asn Gly Glu Phe Lys Val Glu Tyr Asp Arg
            20                  25                  30

Asn Phe Arg Pro Tyr Ile Tyr Ala Leu Leu Arg Asp Asp Ser Gln Ile
        35                  40                  45

Asp Glu Val Lys Lys Ile Thr Ala Glu Arg His Gly Lys Ile Val Arg
    50                  55                  60

Ile Ile Asp Ala Glu Lys Val Glu Lys Lys Phe Leu Gly Arg Pro Ile
65                  70                  75                  80

Thr Val Trp Arg Leu Tyr Phe Glu His Pro Gln Asp Val Pro Ala Ile
            85                  90                  95

Arg Asp Lys Val Arg Glu His Pro Ala Val Val Asp Ile Phe Glu Tyr
        100                 105                 110

Asp Ile Pro Phe Ala Lys Arg Tyr Leu Ile Asp Lys Gly Leu Ile Pro
    115                 120                 125

Met Glu Gly Glu Glu Glu Leu Lys Leu Leu Ala Phe Asp Ile Glu Thr
130                 135                 140
```

```
Leu Tyr His Glu Gly Glu Phe Gly Lys Gly Pro Ile Ile Met Ile
145                 150                 155                 160

Ser Tyr Ala Asp Glu Asn Glu Ala Lys Val Ile Thr Trp Lys Lys Ile
            165                 170                 175

Asp Leu Pro Tyr Val Glu Val Val Ser Ser Arg Glu Met Ile Lys
        180                 185                 190

Arg Phe Leu Arg Val Ile Arg Glu Lys Asp Pro Asp Ile Ile Thr
            195                 200                 205

Tyr Asn Gly Asp Ser Phe Asp Phe Pro Tyr Leu Ala Lys Arg Ala Glu
        210                 215                 220

Lys Leu Gly Ile Lys Leu Pro Leu Gly Arg Asp Gly Ser Glu Pro Lys
225                 230                 235                 240

Met Gln Arg Ile Gly Asp Met Thr Ala Val Glu Ile Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Glu Ala Trp Glu Ser Gly Lys Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Val Ala
        355                 360                 365

Pro Asn Lys Pro Asp Glu Glu Glu Tyr Glu Arg Arg Leu Arg Glu Ser
    370                 375                 380

Tyr Thr Gly Gly Tyr Val Lys Glu Pro Glu Lys Gly Leu Trp Glu Asn
385                 390                 395                 400

Leu Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Lys Glu Tyr
            420                 425                 430

Asp Ile Ala Pro Gln Val Gly His Lys Phe Cys Lys Asp Phe Pro Gly
        435                 440                 445

Phe Ile Pro Ser Leu Leu Lys His Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Lys Pro Glu Glu Ile Lys Lys Lys
545                 550                 555                 560
```

```
Ala Leu Glu Phe Val Lys Tyr Ile Asn Ser Lys Leu Pro Gly Leu Leu
                565                 570                 575

Glu Leu Glu Tyr Glu Gly Phe Tyr Val Arg Gly Phe Val Thr Lys
            580                 585                 590     Lys

Lys Arg Tyr Ala Val Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
            610                 615                 620

Ala Arg Val Leu Glu Ala Ile Leu Lys His Gly Asn Val Glu Glu Ala
625                 630                 635                 640

Val Lys Ile Val Lys Glu Val Thr Gln Lys Leu Ala Lys Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Arg Leu Ala
            675                 680                 685

Ala Arg Gly Val Lys Val Arg Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Leu Lys Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Val Gly Leu Thr Ser
            755                 760                 765

Trp Leu Asn Ile Lys Lys Ser Gly Thr Gly Gly Gly Ala Thr Val
            770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
            820                 825                 830

Lys Glu Leu Leu Gln Met Leu Asp Lys Gln Lys Lys Asn
            835                 840                 845

<210> SEQ ID NO 37
<211> LENGTH: 472
<212> TYPE: PRT
<213> ORGANISM: Artificial Sequence
<220> FEATURE:
<223> OTHER INFORMATION: Description of Artificial Sequence:hybrid
      polymerase PhS6 from Figure 5

<400> SEQUENCE: 37

Met Ile Leu Asp Ala Asp Tyr Ile Thr Glu Asp Gly Lys Pro Ile Ile
1               5                   10                  15

Arg Leu Phe Lys Lys Glu Asn Gly Glu Phe Lys Val Glu Tyr Asp Arg
            20                  25                  30

Asn Phe Arg Pro Tyr Ile Tyr Ala Leu Leu Arg Asp Asp Ser Gln Ile
        35                  40                  45

Asp Glu Val Lys Lys Ile Thr Ala Glu Arg His Gly Lys Ile Val Arg
    50                  55                  60

Ile Ile Asp Ala Glu Lys Val Glu Lys Lys Phe Leu Gly Arg Pro Ile
65                  70                  75                  80
```

-continued

```
Thr Val Trp Arg Leu Tyr Phe Glu His Pro Gln Asp Val Pro Ala Ile
                85                  90                  95

Arg Asp Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Leu Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Lys Ile
                165                 170                 175

Asp Leu Pro Tyr Val Glu Val Val Ser Ser Arg Glu Met Ile Lys
            180                 185                 190

Arg Phe Leu Arg Val Ile Arg Glu Lys Asp Pro Asp Ile Ile Ile Thr
    195                 200                 205

Tyr Asn Gly Asp Ser Phe Asp Phe Pro Tyr Leu Ala Lys Arg Ala Glu
210                 215                 220

Lys Leu Gly Ile Lys Leu Pro Leu Gly Arg Asp Gly Ser Glu Pro Lys
225                 230                 235                 240

Met Gln Arg Ile Gly Asp Met Thr Ala Val Glu Ile Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Glu Ala Trp Glu Ser Gly Lys Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Val Ala
        355                 360                 365

Pro Asn Lys Pro Asp Glu Glu Tyr Glu Arg Arg Leu Arg Glu Ser
    370                 375                 380

Tyr Thr Gly Gly Tyr Val Lys Glu Pro Glu Lys Gly Leu Trp Glu Asn
385                 390                 395                 400

Leu Val Ser Leu Asp Phe Arg Ala Leu Tyr Pro Ser Ile Ile Ile Thr
                405                 410                 415

His Asn Val Ser Pro Asp Thr Leu Asn Arg Glu Gly Cys Lys Glu Tyr
            420                 425                 430

Asp Val Ala Pro Gln Val Gly His Lys Phe Cys Lys Asp Phe Pro Gly
        435                 440                 445

Phe Ile Pro Ser Leu Leu Lys Arg Leu Leu Glu Glu Arg Gln Lys Ile
    450                 455                 460

Lys Arg Lys Met Lys Ala Thr Asn
465                 470
```

<210> SEQ ID NO 38
<211> LENGTH: 60

```
<212> TYPE: PRT
<213> ORGANISM: Artificial Sequence
<220> FEATURE:
<223> OTHER INFORMATION: Description of Artificial Sequence:region
      containing invariable sequence element from
      parental Pfu polymerase containing nucleotide
      binding motif

<400> SEQUENCE: 38

Asp Tyr Arg Gln Lys Ala Ile Lys Leu Leu Ala Asn Ser Phe Tyr Gly
 1               5                  10                  15

Tyr Tyr Gly Tyr Ala Lys Ala Arg Trp Tyr Cys Lys Glu Cys Ala Glu
            20                  25                  30

Ser Val Thr Ala Trp Gly Arg Lys Tyr Ile Glu Leu Val Trp Lys Glu
        35                  40                  45

Leu Glu Glu Lys Phe Gly Phe Lys Val Leu Tyr Ile
        50                  55                  60

<210> SEQ ID NO 39
<211> LENGTH: 60
<212> TYPE: PRT
<213> ORGANISM: Artificial Sequence
<220> FEATURE:
<223> OTHER INFORMATION: Description of Artificial Sequence:region
      containing invariable sequence element from
      parental Deep Vent polymerase containing
      nucleotide binding motif

<400> SEQUENCE: 39

Asp Tyr Arg Gln Arg Ala Ile Lys Ile Leu Ala Asn Ser Tyr Tyr Gly
 1               5                  10                  15

Tyr Tyr Gly Tyr Ala Lys Ala Arg Trp Tyr Cys Lys Glu Cys Ala Glu
            20                  25                  30

Ser Val Thr Ala Trp Gly Arg Glu Tyr Ile Glu Phe Val Arg Lys Glu
        35                  40                  45

Leu Glu Glu Lys Phe Gly Phe Lys Val Leu Tyr Ile
        50                  55                  60

<210> SEQ ID NO 40
<211> LENGTH: 60
<212> TYPE: PRT
<213> ORGANISM: Artificial Sequence
<220> FEATURE:
<223> OTHER INFORMATION: Description of Artificial Sequence:region
      containing invariable sequence element from
      dedigned hybrid polymerase containing nucleotide
      binding motif
<220> FEATURE:
<221> NAME/KEY: MOD_RES
<222> LOCATION: (1)..(60)
<223> OTHER INFORMATION: Xaa = unknown amino acid

<400> SEQUENCE: 40

Asp Tyr Arg Gln Xaa Ala Ile Lys Xaa Leu Ala Asn Ser Xaa Tyr Gly
 1               5                  10                  15

Tyr Tyr Gly Tyr Ala Lys Ala Arg Trp Tyr Cys Lys Glu Cys Ala Glu
            20                  25                  30

Ser Val Thr Ala Trp Gly Arg Xaa Tyr Ile Glu Xaa Val Xaa Lys Glu
        35                  40                  45

Leu Glu Glu Lys Phe Gly Phe Lys Val Leu Tyr Ile
        50                  55                  60

<210> SEQ ID NO 41
<211> LENGTH: 60
```

```
<212> TYPE: PRT
<213> ORGANISM: Artificial Sequence
<220> FEATURE:
<223> OTHER INFORMATION: Description of Artificial Sequence:region
      containing invariable sequence elements from HyS1,
      Hyb2, Hyb3 and HyS4 hybrid polymerase containing
      nucleotide binding motif

<400> SEQUENCE: 41

Asp Tyr Arg Gln Lys Ala Ile Lys Leu Leu Ala Asn Ser Tyr Tyr Gly
 1               5                  10                  15

Tyr Tyr Gly Tyr Ala Lys Ala Arg Trp Tyr Cys Lys Glu Cys Ala Glu
            20                  25                  30

Ser Val Thr Ala Trp Gly Arg Glu Tyr Ile Glu Phe Val Trp Lys Glu
        35                  40                  45

Leu Glu Glu Lys Phe Gly Phe Lys Val Leu Tyr Ile
    50                  55                  60

<210> SEQ ID NO 42
<211> LENGTH: 60
<212> TYPE: PRT
<213> ORGANISM: Artificial Sequence
<220> FEATURE:
<223> OTHER INFORMATION: Description of Artificial Sequence:region
      containing invariable sequence element from PhS1
      hybrid polymerase containing nucleotide binding
      motif

<400> SEQUENCE: 42

Asp Tyr Arg Gln Arg Ala Ile Lys Ile Leu Ala Asn Ser Tyr Tyr Gly
 1               5                  10                  15

Tyr Tyr Gly Tyr Ala Lys Ala Arg Trp Tyr Cys Lys Glu Cys Ala Glu
            20                  25                  30

Ser Val Thr Ala Trp Gly Arg Glu Tyr Ile Glu Phe Val Trp Lys Glu
        35                  40                  45

Leu Glu Glu Lys Phe Gly Phe Lys Val Leu Tyr Ile
    50                  55                  60

<210> SEQ ID NO 43
<211> LENGTH: 60
<212> TYPE: PRT
<213> ORGANISM: Artificial Sequence
<220> FEATURE:
<223> OTHER INFORMATION: Description of Artificial Sequence:region
      containing invariable sequence element from PhS2
      hybrid polymerase containing nucleotide binding
      motif

<400> SEQUENCE: 43

Asp Tyr Arg Gln Arg Ala Ile Lys Leu Leu Ala Asn Ser Phe Tyr Gly
 1               5                  10                  15

Tyr Tyr Gly Tyr Ala Lys Ala Arg Trp Tyr Cys Lys Glu Cys Ala Glu
            20                  25                  30

Ser Val Thr Ala Trp Gly Arg Glu Tyr Ile Glu Leu Val Arg Lys Glu
        35                  40                  45

Leu Glu Glu Lys Phe Gly Phe Lys Val Leu Tyr Ile
    50                  55                  60

<210> SEQ ID NO 44
<211> LENGTH: 60
<212> TYPE: PRT
<213> ORGANISM: Artificial Sequence
<220> FEATURE:
<223> OTHER INFORMATION: Description of Artificial Sequence:region
```

-continued containing invariable sequence element from PhS4
hybrid polymerase containing nucleotide binding
motif

<400> SEQUENCE: 44

```
Asp Tyr Arg Gln Arg Ala Ile Lys Leu Leu Ala Asn Ser Tyr Tyr Gly
 1               5                  10                  15

Tyr Tyr Gly Tyr Ala Lys Ala Arg Trp Tyr Cys Lys Glu Cys Ala Glu
            20                  25                  30

Ser Val Thr Ala Trp Gly Arg Glu Tyr Ile Glu Phe Val Arg Lys Glu
        35                  40                  45

Leu Glu Glu Lys Phe Gly Phe Lys Val Leu Tyr Ile
    50                  55                  60
```

<210> SEQ ID NO 45
<211> LENGTH: 60
<212> TYPE: PRT
<213> ORGANISM: Artificial Sequence
<220> FEATURE:
<223> OTHER INFORMATION: Description of Artificial Sequence:region
      containing invariable sequence element from PhS5
      hybrid polymerase containing nucleotide binding
      motif

<400> SEQUENCE: 45

```
Asp Tyr Arg Gln Arg Ala Ile Lys Leu Leu Ala Asn Ser Phe Tyr Gly
 1               5                  10                  15

Tyr Tyr Gly Tyr Ala Lys Ala Arg Trp Tyr Cys Lys Glu Cys Ala Glu
            20                  25                  30

Ser Val Thr Ala Trp Gly Arg Glu Tyr Ile Glu Leu Val Trp Lys Glu
        35                  40                  45

Leu Glu Glu Lys Phe Gly Phe Lys Val Leu Tyr Ile
    50                  55                  60
```

<210> SEQ ID NO 46
<211> LENGTH: 60
<212> TYPE: PRT
<213> ORGANISM: Artificial Sequence
<220> FEATURE:
<223> OTHER INFORMATION: Description of Artificial Sequence:region
      containing invariable sequence element from PhS7
      hybrid polymerase containing nucleotide binding
      motif

<400> SEQUENCE: 46

```
Asp Tyr Arg Gln Lys Ala Ile Lys Ile Leu Ala Asn Ser Phe Tyr Gly
 1               5                  10                  15

Tyr Tyr Gly Tyr Ala Lys Ala Arg Trp Tyr Cys Lys Glu Cys Ala Glu
            20                  25                  30

Ser Val Thr Ala Trp Gly Arg Lys Tyr Ile Glu Phe Val Arg Lys Glu
        35                  40                  45

Leu Glu Glu Lys Phe Gly Phe Lys Val Leu Tyr Ile
    50                  55                  60
```

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence:6-His
      polyhistidine epitope tag, metal chelate affinity
      ligand

<400> SEQUENCE: 47

```
His His His His His His
  1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence:
      nti-DYKDDDDK epitope tag

<400> SEQUENCE: 48

Asp Tyr Lys Asp Asp Asp Asp Lys
  1               5

<210> SEQ ID NO 49
<211> LENGTH: 45
<212> TYPE: DNA
<213> ORGANISM: Artificial Sequence
<220> FEATURE:
<223> OTHER INFORMATION: Description of Artificial Sequence:primer to
      measure exonuclease activity
<220> FEATURE:
<221> NAME/KEY: modified_base
<222> LOCATION: (1)
<223> OTHER INFORMATION: n = t modified by 6-carboxy-fluorescein (FAM)
<220> FEATURE:
<221> NAME/KEY: modified_base
<222> LOCATION: (45)
<223> OTHER INFORMATION: n = t amino-linked to quencher
      4-(4-dimethylaminophenylazo)benzoyl group (dabcyl,
      DAB)

<400> SEQUENCE: 49 nttttttgagg tgtgtcctac acagcggagt gtaggacaca cctcn                45
```